US012799190B2

(12) United States Patent
Neil et al.

(10) Patent No.: US 12,799,190 B2
(45) Date of Patent: Nov. 17, 2026

(54) METHOD OF TREATING CONDITIONS ASSOCIATED WITH ELEVATED INTERLEUKIN-18 (IL-18) BY ADMINISTERING AN ANTI-IL-18 ANTIBODY

(71) Applicant: Avalo Therapeutics, Inc., Rockville, MD (US)

(72) Inventors: Garry A. Neil, Havertown, PA (US); Inbal Zafir-Lavie, Misgav (IL); Lori Roadcap, Wayne, PA (US)

(73) Assignee: Avalo Therapeutics, Inc., Rockville, MD (US)

( * ) Notice: Subject to any disclaimer, the term of this patent is extended or adjusted under 35 U.S.C. 154(b) by 896 days.

(21) Appl. No.: 17/928,427

(22) PCT Filed: May 31, 2021

(86) PCT No.: PCT/US2021/035065

§ 371 (c)(1),
(2) Date: Nov. 29, 2022

(87) PCT Pub. No.: WO2021/247454

PCT Pub. Date: Dec. 9, 2021

(65) Prior Publication Data

US 2023/0203150 A1 Jun. 29, 2023

Related U.S. Application Data

(60) Provisional application No. 63/032,929, filed on Jun. 1, 2020.

(51) Int. Cl.
*C07K 16/24* (2006.01)
*A61K 39/00* (2006.01)
*A61P 29/00* (2006.01)
*A61P 31/14* (2006.01)
*A61P 37/06* (2006.01)

(52) U.S. Cl.
CPC ............ *C07K 16/244* (2013.01); *A61P 29/00* (2018.01); *A61P 31/14* (2018.01); *A61P 37/06* (2018.01); *A61K 2039/505* (2013.01); *C07K 2317/565* (2013.01); *C07K 2317/76* (2013.01)

(58) Field of Classification Search
CPC ............ C07K 16/244; C07K 2317/565; C07K 2317/76; C07K 14/54; A61P 29/00; A61P 31/14; A61P 37/06; A61P 37/00; A61P 11/00; A61K 2039/505
See application file for complete search history.

(56) References Cited

U.S. PATENT DOCUMENTS 6,706,487 B1 3/2004 Abdel-Meguid et al.
8,133,978 B2 3/2012 Ellis et al.
8,187,836 B2 5/2012 Hsieh
9,255,144 B2 2/2016 Dobson et al.
9,376,489 B2 6/2016 Bardroff et al.
10,858,426 B2 12/2020 Pfeifer et al.
10,882,905 B2 1/2021 Del Val et al.
11,111,293 B2 9/2021 Bardroff et al.
2005/0100965 A1 5/2005 Ghayur et al.
2005/0147610 A1 7/2005 Ghayur et al.
2006/0155349 A1 7/2006 Kemeny et al.
2010/0291088 A1 11/2010 Ghayur et al.
2013/0177498 A1 7/2013 Goldenberg et al.
2014/0004128 A1 1/2014 Dobson et al.
2016/0215048 A1 7/2016 Pfeifer et al.
2018/0127494 A1 5/2018 Del Val et al.
2018/0194861 A1 7/2018 Dong et al.
2019/0077858 A1 3/2019 Shimizu et al.
2019/0085068 A1 3/2019 Bardroff et al.
2019/0249232 A1 8/2019 Desai
2020/0377586 A1 12/2020 Del Val et al.
2020/0392222 A1 12/2020 Pfeifer et al.
2020/0399362 A1 12/2020 Ridker
2021/0188968 A1 6/2021 Del Val et al.

FOREIGN PATENT DOCUMENTS

EP 0974600 A2 1/2000
EP 1621616 A1 2/2006
EP 1423138 B1 12/2014
EP 2931749 B1 4/2019
EP 2924117 B1 8/2019
EP 2970865 B1 9/2020
WO 0158956 A2 8/2001
WO 2012085015 A1 6/2012
WO 2019196522 A1 10/2019
WO 2019213686 A1 11/2019
WO 2021234381 A1 11/2021

OTHER PUBLICATIONS

ClinicalTrials.gov ID NCT01035645 (Jun. 12, 2017). Retrieved from the internet Aug. 20, 2025. (https://clinicaltrials.gov/study/NCT01035645?intr=GSK1070806&rank=7).*
Al-Samkari, Hanny et al., "Hemophagocytic Lymphohistiocytosis", Annual Review of Pathology: Mechanisms of Disease, 2018, 13: 27-49.
Girard, Charlotte et al., "Elevated serum levels of free interleukin-18 in adult-onset Still's disease", Rheumatology 2016; 55: 2237-2247.
Guo, Xi-zhi J. et al., "New fronts emerge in the influenza cytokine storm", Semin Immunopathol. 2017; 39(5): 541-550.

(Continued)

*Primary Examiner* — Robert S Landsman
(74) *Attorney, Agent, or Firm* — McNeill PLLC

(57) ABSTRACT

The present disclosure relates to methods of treating and/or detecting respiratory and inflammatory conditions associated with IL-18 by administering an anti-IL-18 antibody, optionally wherein the antibody comprises the six CDRs of SEQ ID NOS: 122, 123, 124, 126, 127, and 128, wherein 122-124 comprise the heavy chain CDRs and 126-128 comprise the light chain CDRs, to subjects having elevated IL-18 levels. Conditions include acute respiratory distress syndrome (ARDS) and hemophagocytic lymphohistiocytosis (HLH)/Macrophage activation syndrome (MAS), optionally wherein the ARDS and HLH/MAS are associated with viral infection, including coronavirus infection.

11 Claims, 4 Drawing Sheets

Specification includes a Sequence Listing.

(56) References Cited

OTHER PUBLICATIONS

Manjili, Rose H. et al., "COVID-19 as an Acute Inflammatory Disease", The Journal of Immunology 2020; 205:12-19.
Mohlenkamp, Stefan et al., "Ventilation of COVID-19 patients in intensive care units", Herz 2020, 45:329-331.
PCT International Search Report and Written Opinion from PCT/US2021/035065 mailed Oct. 4, 2021, 12 pages.
Nakanishi, Kenji, "Unique Action of Interleukin-18 on T Cells and Other Immune Cells", Frontiers in Immunology, Apr. 2018, vol. 9, Article 763, 7 pages.
Novick, Daniela et al., "Interleukin-18 Binding Protein: a Novel Modulator of the Th1 Cytokine Response", Immunity, vol. 10, 127-136, Jan. 1999.
Oganesyan, Vaheh et al., "Structural characterization of a human Fc fragment engineered for lack of effector functions", Acta Cryst. (2008) D64, 700-704.
Parikh, Chirag R. et al., "Urine IL-18 Is an Early Diagnostic Marker for Acute Kidney Injury and Predicts Mortality in the Intensive Care Unit", J Am Soc Nephrol 16: 3046-3052, 2005.
Park, Matthew D., "Macrophages: a Trojan hose in COVID-19?", Nature Reviews, Immunology, vol. 20, Jun. 2020, p. 351.
Park, Matthew D., "SARS-CoV-2 cross reactivity in healthy donors", Nature Reviews, 2020, vol. 20, 408.
Pearson, William R. et al., "Improved tools for biological sequence comparison", Proc. Natl. Acad. Sci., vol. 85, pp. 2444-2448, Apr. 1988.
Peiris, JSM et al., "Re-emergence of fatal human influenza A subtype H5N1 disease", Lancet, vol. 363, 2004, 617-619.
Pinkerton, James W. et al., "Inflammasomes in the lung", Molecular Immunology, vol. 86, Jun. 2017, 44-55.
Ren, Li-Li et al., "Identification of a novel coronavirus causing severe pneumonia in human: a descriptive study", Chinese Medical Journal, 2020; 133(9) 1015-1024.
Sandoval-Montes, C. & Santos-Argumedo, L. "CD38 is expressed selectively during the activation of a subset of mature T cells with reduced proliferation but improved potential to produce cytokines" Journal of leukocyte biology 77, 513-521 (2005).
Sharma, Deepika et al., "The cell biology of inflammasomes: Mechanisms of inflammasome activation and regulation", The Journal of Cell Biology, 2016, vol. 213, No. 6, 617-629.
Shimizu, Masaki et al., Interleukin-18 for predicting the development of macrophage activation syndrome in systemic juvenile idiopathic arthritis, Clinical Immunology, vol. 160, Issue 2, Oct. 2015, pp. 277-281.
Siddiqi, Hasan K. et al., "COVID-19 illness in native and immunosuppressed states: a clinical-therapeutic staging proposal", The Journal of Heart and Lung Transplantation, vol. 39, No. 5, May 2020, 405-407.
Siu, Kam-Leung et al., "Severe acute respiratory syndrome coronavirus ORF3a protein activates the NLRP3 inflammasome by promoting TRAF3-dependent ubiquitination of ASC", The FASEB Journal, vol. 33, Aug. 2019, 8865-8877.
Smith, T.F. et al., "Identification of Common Molecular Subsequences", J. Mol. Biol. (1981) 147, 195-197.
Szyper-Kravitz, Martine MD, "The hemophagocytic Syndome/Macrophage Activation Syndrome: a Final Common Pathway of a Cytokine Storm", Israel Medical Association journal: IMAJ 11, (2009), 633-634.
Takada, Hidetoshi et al., "Interleukin-18 in Hemophagocytic Lymphohistiocytosis", Leukemia & Lymphoma, vol. 42, 2001, 21-28.
Tate, Michelle D. et al., "Reassessing the role of the NLRP3 inflammasome during pathogenic influenza A virus infection via temporal inhibition", Scientific Reports, 6:27912: DOI 10.1038/srep27912, 2016.
Triantafilou, Kathy et al., "Ion flux in the lung: virus-inducted inflammasome activation", Trends in Microbiology, Oct. 2014, vol. 22, No. 10, 580-588.
Wang, Dawei et al., "Clinical Characteristics of 138 Hospitalized Patients with 2019 Novel Coronavirus-Infected Pneumonia in Wuhan, China", JAMA 2020, 323(11): 1061-1069.
World Health Organization (WHO), Coronavirus disease (COVID-19) pandemic, 2019, retrieved from https://www.who.int/emergencies/diseases/novel-coronavirus-2019 on Jan. 18, 2023.
Wu, Fan et al., "A new coronavirus associated with human respiratory disease in China", Nature 2020, vol. 579, 265-269.
Xiao, F. et al. "Evidence for Gastrointestinal Infection of SARS-CoV-2" Gastroenterology, 158(6):1831-1833 (2020).
Xu et al., "Transcriptome Sequencing Identifies Novel Immune Response Genes Highly Related to the Severity of Human Adenovirus Type 55 Infection" Front Microbiol vol. 6, Art. 130 (2019).
Xu, Zhe et al., "Pathological findings of COVID-19 associated with acute respiratory distress syndrome", Lancet Respir Med 2020; 8:420-22.
Yasin, Shima et al., "IL-18 as therapeutic target in a patient with resistant systemic juvenile idiopathic arthritis and recurrent macrophage activation syndrome", Rheumatology 2020; 59:442-445.
Zalinger, Zachary B. et al., "Role of the inflammasome-related cytokines IL-1 and IL-18 during infection with murine coronavirus", J. Neuroviol. (2017) 23:845-854.
Zhang, Li-Ming et al., "Interleukin-18 binding protein attenuates lipopolysaccharide-induced acute lung injury in mice via suppression NF-kB and activation Nrf2 pathway", Biochemical and Biophysical Research Communications, vol. 505, Issue 3, 2018, 837-842.
Zhang, Li-Ming et al., "Neutralization of IL-18 by IL-18 binding protein ameliorates bleomycin-induced pulmonary fibrosis via inhibition of epithelial-mesenchymal transition", Biochemical and Biophysical Research Communications, vol. 508, Issue 2, 2019, 660-666.
Altschul, Stephen F. et al., "Basic Local Alignment Search Tool", J. Mol. Biol. (1990) 215, 403-410.
Bauernfeind, Franz et al., "Inflammasomes: current understanding and open questions", Cellular and Molecular Life Sciences (2011) 68:765-783.
Buatois, Vanessa et al., "Use of a mouse model to identify a blood biomarker for IFNy activity in pediatric secondary hemophagocytic lymphohistiocytosis", Translational Research, Feb. 2017, 37-52.
Canna, Scott W. et al., "Life-threatening NLRC4-associated hyperinflammation successfully treated with IL-18 inhibition", J Allergy Clin Immunol, May 2017, vol. 139, No. 5, 1698-1701.
Chan, JF, et al., "A familial cluster of pneumonia associated with the 2019 novel coronavirus indicating person-to-person transmission: a study of a family cluster" Lancet, 395(10223):514-523 (2020).
Channappanavar, R. et al. "Dysregulated Type I Interferon and Inflammatory Monocyte-Macrophage Responses Cause Lethal Pneumonia in SARS-CoV-Infected Mice" Cell Host & Microbe 19, 181-193 (2016).
Channappanavar, Rudragouda et al., "Pathogenic human coronavirus infections: causes and consequences of cytokine storm and immunopathology", Semin Immunopathol 2017, 39:529-539.
Chen, I-Yin et al., "Severe Acute Respiratory Syndrome Coronavirus Viroporin 3a Activates the NLRP3 Inflammasome", Frontiers in Microbiology, Jan. 2019, vol. 10, Article 50, 9 pages.
Chen, Jianwen et al., "Bacterial Heavy-Metal and Antibiotic Resistance Genes in a Copper Tailing Dam Area in Northern China", Frontiers in Microbiology, 2019, vol. 10, Article 1916, 12 pages.
Chen, Nanshan et al., "Epidemiological and clinical characteristics of 99 cases of 2019 novel coronavirus pneumonia in Wuhan, China: a descriptive study", Lancet, vol. 395, 2020, 507-513.
Chen, Yu et al., "Active or latent tuberculosis increases susceptibility to COVID-19 and disease severityr", medRxiv, 2020, 15 pages.
Clinical Trials, History of Changes for Study: NCT01322594; a Study to Evaluate the Safety of MEDI2338 in Subjects With Chronic Obstructive Pulmonary Disease, Mar. 23, 2011, retrieved from the internet at https://www.clinicaltrials.gov/ct2/history/NCT01322594?A=1&B=1&C=merged#StudyPageTop on Dec. 28, 2022.
Clinical Trials, History of Changes for Study: NCT01322594; a Study to Evaluate the Safety of MEDI2338 in Subjects With

(56) References Cited

OTHER PUBLICATIONS

Chronic Obstructive Pulmonary Disease, Oct. 9, 2013, retrieved from the internet at https://www.clinicaltrials.gov/ct2/history/NCT01322594?A=6&B=6&C=merged#StudyPageTop on Dec. 28, 2022.
Cunha, Cheston B. et al., "Middle East respiratory syndrome (MERS), a new zoonotic viral pneumonia", Virulence 5:6, 650-654; Aug. 15, 2014.
Dall'Acqua, William F. et al., "Increasing the Affinity of a Human IgG1 for the Neonatal Fc Receptor: Biological Consequences", The Journal of Immunology, 2002; 169:5171-5180.
Dall'Acqua, William F. et al., Properties of Human IgG1s Engineered for Enhanced Binding to the Neonatal Fc Receptor (FcRn), The Journal of Biological Chemistry, vol. 281, No. 33, pp. 23514-23524, Aug. 2006.
Dima, Efrossini et al., "Implication of Interleukin (IL)-18 in the pathogenesis of chronic obstructive pulmonary disease (COPD)", Cytokine, vol. 74, Issue 2, Aug. 2015, 313-317.
Dinarello, Charles A. et al., "Interleukin-18 and IL-18 binding protein", Frontiers in Immunology, Oct. 2013, vol. 4, Article 289, 10 pages.
Dinarello, Charles A., "Overview of the IL-1 family in innate inflammation and acquired immunity", Immunol Rev. Jan. 2018; 281(1):8-27.
Dolinay, Tamas et al., "Inflammasome-regulated Cytokines Are Critical Mediators of Acute Lung Injury", American Journal of Respiratory and Critical Care Medicine, vol. 185, 2012, 1225-1234.
Dong, Guangsu et al., "Serum interleukin-18: a novel prognostic indicator for acute respiratory distress syndrome", Medicine, 2019 98:21, 5 pages.
Dos Santos, Gimena et al., "The inflammasome in lung diseases", Am J. Physiol Lung Cell Mol Physiol 303: L627-L633, 2012.
Dosch, Susan F. et al., "SARS coronavirus spike protein-induced innate immune response occurs via activation of the NF-kB pathway in human monocyte macrophages in vitro", Virus Research 142 (2009) 19-27.
Fehr, A. R., et al., "Middle East Respiratory Syndrome: Emergence of a Pathogenic Human Coronavirus" Annual review of medicine 68, 387-399 (2017).
Feng, Zeqing et al., "The Novel Severe Acute Respiratory Syndrome Coronavirus 2 (SARS-CoV-2) Directly Decimates Human Spleens and Lymph Nodes", medRxiv, 2020, https://doi.org/10.1101/2020.03.27.20045427.
Fernandes-Alnemri, T. et al., The pyroptosome: a supramolecular assembly of ASC dimers mediating inflammatory cell death via caspase-1 activation, Cell Death and Differentiation (2007) 14, 1590-1604.
Ghayur, Tariq. et al., "Caspase-1 processes IFN-y-inducing factor and regulates LPS-induced IFN-y production", Nature 386 (1997) 619-623.
Graham, Rachel L. et al., "A decade after SARS: strategies for controlling emerging coronaviruses", Nature 2013, vol. 11, 836-848.
Gralinski, L. E. & Baric, R. S. "Molecular pathology of emerging coronavirus infections" The Journal of pathology 235, 185-195 (2015).
Gu, Jiang et al., "Multiple organ infection and the pathogenesis of SARS", The Journal of Experimental Medicine, 2005, vol. 202, No. 3, pp. 415-424.
Guo, Jing et al., "The Serum Profile of Hypercytokinemia Factors Identified in H7N9-Infected Patients can Predict Fatal Outcomes", Scientific Reports 5, 10942, doi:10.1038/srep10942 (2015).
Huang, Chaolin et al., "Clinical features of patients infected with 2019 novel coronavirus in Wuhan, China", Lancet 2020, 395: 497-506.
Huang, Kao-Jean et al., "An interferon-y-Related Cytokine Storm in SARS Patients", Journal of Medical Virology 75: 185-194 (2005).
Jordan, Jacqueline A. et al., "Role of IL-18 in Acute Lung Inflammation", The Journal of Immunology, 2001, 167 (12): 7060-7068.
Jordan, Michael B. et al., "An animal model of hemophagocytic lymphohistiocytosis (HLH): CD8+ T cells and interferon gamma are essential for the disorder", Blood, Aug. 2004, vol. 104, No. 3, 735-743.
Katz, Josh et al., "Could Coronavirus Cause as Many Deaths as Cancer in the U.S.? Putting Estimates in Context", New York Times, Mar. 16, 2020, retrieved from https://www.nytimes.com/interactive/2020/03/16/upshot/coronavirus-best-worst-death-toll-scenario.html on Jan. 18, 2023.
Kawai, Taro et al., "The role of pattern-recognition receptors in innate immunity: update on Toll-like receptors", Nature Immunology, May 2010, vol. 11, No. 5, 373-384.
Law, Helen K.W. et al., "Chemokine up-regulation in SARS-coronavirus-infected, monocyte-derived human dendritic cells", Blood, 2005, vol. 106, No. 7, pp. 2366-2374.
Lieben, Liesbet, "Direct contact between mature osteoblasts and osteoclasts", Nature Reviews Rheumatology (2018), 1 page.
Maeno, Nobuaki et al., "Increased Interleukin-18 Expression in Bone Marrow of a Patient with Systemic Juvenile Idiopathic Arthritis and Unrecognized Macrophage-Activation Syndrome", Arthritis & Rheumatism, vol. 50, No. 6, Jun. 2004, pp. 1935-1938.
Makabe, Hideyuki et al., "Interleukin-18 levels reflect the long-term prognosis of acute lung injury and acute respiratory distress syndrome", Journal of Anesthesia 26, 658-663 (2012).
Martinon, Fabio et al., "The Inflammasome: a Molecular Platform Triggering Activation of Inflammatory Caspases and Processing of proIL-β", Molecular Cell, vol. 10, 417-426, Aug. 2002.
Mazodier, Karin et al., "Severe imbalance of IL-18/IL-18BP in patients with secondary hemophagocytic syndrome", Blood, Nov. 2005, vol. 106, No. 10, 3483-3489.
Mcauley, Julie L. et al., "Activation of the NLRP3 Inflammasome by IAV Virulence Protein PB1-F2 Contributes to Severe Pathophysiology and Disease", PLOS, May 2013,vol. 9, Issue 5, E1003392.
Mcgonagle, Dennis et al., "The Role of Cytokines including Interleukin-6 in COVID-19 induced Pneumonia and Macrophage Activation Syndrome-Like Disease", Autoimmunity Reviews (2020); 19(6): 102537.
Mehta, P., et al. "Therapeutic blockade of granulocyte macrophage colony-stimulating factor in COVID-19-associated hyperinflammation: challenges and opportunities" The Lancet, 8(8): 822-830 (2020).
Mehta, Puja et al., "COVID-19: consider cytokine storm syndromes and immunosuppression", Lancet, vol. 395, Mar. 28, 2020.
Mistry, Prafull et al., "Safety, tolerability, pharmacokinetics, and pharmacodynamics of single-sode antiinterleukin-18 mAb GSK1070806 in healthy and obese subjects", Int. Journal of Clinical Pharmacology and Therapeutics, vol. 52, Oct. 2014, 867-879.
Moore, John B. et al., "Cytokine release syndrome in severe COVID-19", Science 2020, vol. 368, issue 6490, 473-474.
Nakanishi, Kenji et al., "Interleukin-18 Regulates Both Th1 and Th2 Responses", Annual Review of Immunology, vol. 19: 423-474 (2001).

* cited by examiner

METHOD OF TREATING CONDITIONS ASSOCIATED WITH ELEVATED INTERLEUKIN-18 (IL-18) BY ADMINISTERING AN ANTI-IL-18 ANTIBODY

CROSS-REFERENCE TO RELATED APPLICATIONS

This application is a national phase entry pursuant to 35 U.S.C. § 371 of International Application No. PCT/US2021/035065, filed May 31, 2021, which claims the benefit of priority to U.S. Provisional Application No. 63/032,929, filed Jun. 1, 2020, the contents of each of which are incorporated herein by reference in their entirety for all purposes.

The instant application contains a Sequence Listing which has been submitted electronically in ASCII format and is hereby incorporated by reference in its entirety. Said ASCII copy, created on May 26, 2021, is named 01118-0048-00PCT ST25.txt and is 107,000 bytes in size.

FIELD OF THE INVENTION

The present disclosure relates to methods of diagnosing and treating subjects with conditions associated with elevated IL-18 levels, including subjects with immune dysregulation that may lead to multisystem organ failure, or subjects with acute lung injury (ALI) or acute respiratory distress syndrome (ARDS), including those associated with coronavirus infection, including COVID-19, by administering an anti-interleukin 18 (IL-18) neutralizing antibody.

BACKGROUND OF THE INVENTION

In December 2019, the spread of 2019 novel coronavirus 2019-nCoV (SARS-CoV2) has emerged as a global emergency, causing both high morbidity and mortality. SARS-CoV2 originated in Wuhan China (Wu, F. et al. *Nature* 579, 265-269 (2020)) but has rapidly spread worldwide and has been designated a global pandemic by the World Health Organization. The virus is highly infectious, and it is estimated that up to 60% of the world's population may eventually become infected by SARS-CoV2. In the US alone this would represent more than 180 million individuals.

COVID-19 is a disease caused by SARS-CoV2. The initial presentation of COVID-19 infection includes fever with or without respiratory symptoms including cough, shortness of breath, and pneumonia. In most subjects the illness is mild and self-limited, however 15% to 20% experience severe respiratory illness, requiring hospitalization and oxygen therapy (Huang, C. et al. *Lancet* 395, 497-506 (2020)). Many of these subjects require intensive care and ventilation owing to emergence of acute respiratory distress syndrome (ARDS) (id.; Graham, R. L., Donaldson, E. F. & Baric, R. S. *Nature reviews. Microbiology* 11, 836-848 (2013)), which is a well-described and potentially fatal complication of other viral respiratory syndromes (i.e., SARS, MERS, and H1N1). Other complications of COVID-19 include arrhythmia, shock, acute kidney injury, acute cardiac injury, liver dysfunction, and secondary infection. (Huang C, et al., *Lancet* (2020); Wang, D. et al., *JAMA* (2020)).

Accumulating evidence suggests that the main cause for mortality is unleashed immune response causing cytokine storm, acute lung injury, and Acute Respiratory Distress Syndrome (ARDS) resulting in fatal respiratory failure.

Even in subjects who recover there may be long-lasting and debilitating sequelae. There is an urgent need for cytokine-neutralizing therapeutic agents, which will control COVID-19 associated hyper-inflammation and ARDS.

In COVID-19 and other human corona respiratory virus (hCoV) infections, ARDS appears to result from a dysregulated hyperinflammatory response manifested by the release of excessive pro-inflammatory cytokines and chemokines, coined "cytokine storm." (Channappanavar, R. & Perlman, S. *Seminars in immunopathology* 39, 529-539, (2017); Mehta, P. *The Lancet* (2020)). Cytokines and chemokines have long been thought to play an important role in immunity and immunopathology during virus infections. A rapid and well-coordinated innate immune response is the first line of defense against viral infections, but dysregulated and excessive immune responses may cause immunopathology. (Fehr, A. R., Channappanavar, R. & Perlman, S. *Annual review of medicine* 68, 387-399 (2017); Channappanavar, R. et al. *Cell host & microbe* 19, 181-193 (2016)). Although there is no direct evidence for the involvement of pro-inflammatory cytokines and chemokines in lung pathology during SARS and MERS, correlative evidence from subjects with severe disease suggests a role for hyper-inflammatory responses in hCoV pathogenesis. (Channappanavar, *Seminars in immunopathology* 39, 529-539 (2017); Mehta (2020); Sandoval-Montes, C. & Santos-Argumedo, L. *Journal of leukocyte biology* 77, 513-521 (2005); Xu et al., *Microbiol* 6(10):130 (2019)).

The cytokine storm in COVID-19 infection is thought to result from initial rapid virus replication which may be more likely in immunocompromised subjects. A notable feature of pathogenic human coronaviruses such as SARS-CoV and MERS-CoV is that both viruses replicate to high titers very early after infection both in vitro and in vivo (Gralinski, L. E. & Baric, R. S. *The Journal of pathology* 235, 185-195 (2015)). This high replication could lead to enhanced cytopathic effects and production of higher levels of pro-inflammatory cytokines and chemokines by infected epithelial cells. (Xiao, F. et al. *Gastroenterology* (2020)). These cytokines and chemokines in turn orchestrate massive infiltration of inflammatory cells into the lungs. (Gralinski, L. E. & Baric, R. S. *The Journal of pathology* 235, 185-195 (2015)). Studies from hCoV infections in humans and experimental animals demonstrated a strong correlation between high SARS-CoV and MERS-CoV titers and disease severity. Infection also appears to increase secretion of cytokines (e.g., IL4 and IL10) which in turn can increase T cell activation. (Sandoval-Montes (2005); Xu, Z. et al. *The Lancet*. Respiratory medicine (2020)). Thus, the cytokine storm that drives tissue injury and vascular permeability in the lungs is likely mediated, in part by T cell activation with increased expression of cytokines.

In addition, reports indicate that pulmonary (lung) fibrosis, which is known to be a result of ARDS, is a known COVID-19 infection complication. (Huang, C. et al. *Lancet* 395, 497-506 (2020)).

Both human and animal studies demonstrate accumulation of inflammatory monocyte-macrophages and neutrophils in the lungs following hCoV infection. These cells are the predominant source of cytokines and chemokines associated with hCoV lethal disease observed both in humans and animal models. (Channappanavar, *Seminars in immunopathology* (2017)).

While a primary focus of treatment of COVID-19 is the development of appropriate antiviral and vaccination approaches, currently no established therapy exists for treatment of ARDS associated with COVID-19. Agents targeting cytokine storm have included cytokine-directed therapies, including IL-1β and IL-6 antagonists; however, there is no established single therapy for the treatment and/or prevention of ALI associated with cytokine storm. The development of a safe and effective therapy for COVID-19-associated acute lung injury (ALI) and ARDS could significantly reduce the mortality and post infectious morbidity of this global pandemic and alleviate the severe strain placed on healthcare systems.

Further, the initial clinical sign of COVID-19 that allowed case detection was pneumonia (Chan, J F, et al., *Lancet* (2020)). Complications of COVID-19 pneumonia include acute respiratory distress syndrome (ARDS), arrhythmia, shock, acute kidney injury, acute cardiac injury, liver dysfunction, and secondary infection (Huang C, et al., *Lancet* (2020); Wang, D. et al., JAMA (2020)). The main cause of mortality in COVID-19 appears to be dysregulated hyperimmune response causing cytokine storm, acute lung injury and ARDS. Fifteen to 20% of COVID-19 patients experience severe respiratory illness, requiring hospitalization and oxygen therapy (Huang C, et al., *Lancet* (2020)). There are currently no treatments to prevent progression of COVID-19 pneumonia to ARDS in patients with COVID-19.

COVID-19 Patients Demonstrate Cytokine Storm and Secondary HLH Features

SARS-CoV-2 shares high genetic similarity with other human corona respiratory viruses (hCoV); 79% identity to SARS-CoV and 51.8% identity to MERS-CoV have been reported. (Ren, L. L. et al. *Chinese medical journal* (2020). In both SARS-CoV and MERS-CoV there is evidence of dysregulated hyperinflammatory response manifested by the release of excessive pro-inflammatory cytokines and chemokines, coined "cytokine storm." This is in addition to reported abnormal T-cell count and unbalanced macrophage response causing ARDS and in some patients lead to death. (Channappanavar, R. & Perlman, S. *Seminars in immunopathology* 39, 529-539 (2017); Mehta, P. *The Lancet* (2020)). Cytokines and chemokines have long been recognized to play a role in immunity and immunopathology during virus infections. A rapid and well-coordinated innate immune response is the first line of defense against viral infections, but dysregulated and excessive immune responses may cause immunopathology. (Fehr, A. R., Channappanavar, R. & Perlman, S. *Annual review of medicine* 68, 387-399 (2017); Channappanavar, R. et al. *Cell host & microbe* 19, 181-193 (2016)). Correlative evidence from patients with SARS, MERS and SARS-CoV-2 infection suggests a role for hyper-inflammatory responses in hCoV pathogenesis. (Mehta, P. The Lancet (2020); Fehr, A. R., Channappanavar, R. & Perlman, S. *Annual review of medicine* 68, 387-399 (2017); Sandoval-Montes, C. & Santos-Argumedo, L. *Journal of leukocyte biology* 77, 513-521 (2005)).

An additional hyperinflammatory disorder associated with COVID-19 is secondary hemophagocytic lymphohistiocytosis (sHLH). (Mehta, P. et al. *Lancet* (2020); McGonagle, D., et al. *Autoimmunity reviews* (2020)). sHLH is a clinical syndrome leading to severe inflammatory response, which is induced by a cytokine storm and is characterized by proliferation of macrophages causing lymphadenopathy. Secondary HLH may also be known as macrophage activation syndrome (MAS). The immune response, which is simultaneously uncontrolled and impaired, eventually causes multiorgan failure. (Szyper-Kravitz, M. *The Israel Medical Association journal: IMAJ* 11, 633-634 (2009)). COVID-19 patients demonstrate high serum CRP levels and hyperferritinaemia, which are key features in sHLH diagnosis.

SARS-CoV-2 Infects and Activates Macrophages

SARS-Cov, is highly similar to the COVID-19 virus (SARS-Cov-2) and binds the same receptor: ACE2. It has been shown that SARS infects and activates macrophages (Dosch, S. F., et al. *Virus Research* 142, 19-27 (2009); Law, H. K. W. et al. *Blood* 106, 2366-2374 (2005); Gu, J. et al. *J Exp Med* 202, 415-424 (2005)) and induces secretion of pro-inflammatory cytokines such as IL-6.

Emerging evidence suggests that SARS-CoV-2, which bind and enter the cell via ACE2 receptor in the lung and intestinal tract, also infects CD68+CD169+ macrophages (Park, M. D. *Nature reviews. Immunology* (2020); Chen, Y. et al. medRxiv (2020)). SARS-CoV-2 infected macrophages, upon activation, are a major source of pro-inflammatory cytokines such as IL-6 (Moore, B. J. B. et al. Science (2020)), and may be a source for IL-18 as well.

NLRP3 Inflammasome is Activated in COVID-19 Infection, and Releases Active IL-18

One of the first responses to SARS-CoV-2 and similar coronaviruses (SARS-CoV) is innate immune response, which is activated by pattern recognition receptors (PRRs, aka Toll-like receptors), that recognize pathogen associated molecular patterns (PAMPs). (Kawai, T. & Akira, S. *Nature immunology* 11, 373-384 (2010)). The Nod-like receptor family, pyrin domain-containing 3 (NLRP3) is a member of the Toll-like receptor family of nucleotide-binding oligomerization domain (NOD), leucine-rich repeat (LRR)-containing proteins (NLR). (Sharma, D. & Kanneganti, T. D. *The Journal of cell biology* 213, 617-629, doi:10.1083/jcb.201602089 (2016)). NLRP3 receptor is known to be activated by viral infections such as SARS-CoV2 (COVID-19) (Bauernfeind, F. et al. *Cellular and molecular life sciences: CMLS* 68, 765-783 (2011); Chen, I. Y., et al. *Frontiers in microbiology* 10, 50 (2019)), which results in recruitment of proteins to NLPR3 to generate the intracellular inflammasome complex, consequently activating intracellular cysteine protease coined caspase-1 (Fernandes-Alnemri, T. et al. *Cell death and differentiation* 14, 1590-1604 (2007). Active caspase-1 cleaves pro-Interleukine-1β (IL-1β) and pro-IL-18 into their mature active forms. (Martinon, F., et al. *Molecular Cell* 10, 417-426 (2002); Ghayur, T. et al. *Nature* 386, 619-623 (1997)). In mouse experiments, inhibition of NLRP3 in the early phase of Influenza A virus infection increased mortality, whereas suppression of NLRP3 at the peak of infection allowed for a protective effect. (Tate, M. et al. *Sci Rep* 6, 27912 (2016)).

IL-18 is a key driver of innate and adaptive inflammation. IL-18 is a proinflammatory cytokine, first described as IFN-γ-inducing factor. IL-18 belongs to the IL-1 family of cytokines. Similar to IL-1β, IL-18 is produced as a pro-peptide which is active only upon cleavage by caspase-1 after inflammasome activation. Pro-IL-18 is present in healthy cells and constitutively expressed by monocytes and epithelial cells. Macrophages and dendritic cells are the primary source of active IL-18 (Dinarello, C. A. *Immunological reviews* 281, 8-27 (2018)), but additional cells can also secrete IL-18. IL-18 participates in the Th1 paradigm. The importance of IL-18 as an immunoregulatory cytokine is derived from its prominent biological property of inducing IFNγ from NK cells (Dinarello, C. A., *Frontiers in immunology* 4, 289 (2013)). Together with IL-12 or IL-15, IL-18 is capable of inducing IFNγ secretion from T cells, NK cells, NKT cells, B cells, DC and macrophages to produce high IFN-γ (Nakanishi, K. Frontiers in immunology 9, 763 (2018)). IL-18 can also stimulate Th2 allergic response when IL-12 is not present. In the presence of IL-3, IL-18 induces mast cells and basophils which result in secretion of IL-4 and IL-13. Therefore, IL-18 is a cytokine that stimulates a variety of cells and has pleiotropic function depending on the cytokine milieu, and can stimulate both adaptive and innate immune response (Nakanishi, K., *Annual review of immunology* 19, 423-474 (2001)).

IL-18 binding protein (IL-18BP) is a soluble protein specifically binding IL-18 and inhibiting its activity. (Novick, D. et al. *Immunity* 10, 127-136 (1999)). The affinity of IL-18BP to IL-18 is estimated to be 400 pM, similar to the affinity of IL-18 to its receptor (IL-18Rα/IL-18Rβ). IL-18BP has proved to neutralize IL-18 activity in many pathological mouse models, and has been used as an IL-18 neutralizing agent in human clinical trials (NCT02398435).

IL-18 has a major role is several autoinflammatory disorders such as systemic lupus erythematosus (SLE), rheumatoid arthritis, type 1 diabetes, Crohn's disease, psoriasis, graft-versus-host disease. (Dinarello, C. A. *Immunological reviews* 281, 8-27 (2018)). Hemophagocytic lymphohistiocytosis (HLH)/macrophage activation syndrome (MAS) (Takada, H., et al. *Leukemia & Lymphoma* 42, 21-28 (2001); Lieben, L. *Nature reviews. Rheumatology* (2018)) and chronic obstructive pulmonary disease (COPD). (Dima, E. et al. *Cytokine* 74, 313-317 (2015)), IL-18 is Secreted in ARDS and its Levels Correlate with Severity NLRP3 inflammasome has shown to be protective in models of lung infection. However, over-activation of NLRP3 can support chronic inflammation of the lung, which results in ALI (Pinkerton, J. W. et al. *Molecular immunology* 86, 44-55 (2017)), which may eventually lead to ARDS. High IL-18 levels have been detected in ARDS patients' serum (Dong, G. et al. Medicine 98 (2019); Dolinay, T. et al. *American journal of respiratory and critical care medicine* 185, 1225-1234 (2012)) and urine (Parikh, C. R., et al. *Journal of the American Society of Nephrology: JASN* 16, 3046-3052 (2005)), and correlate with disease severity (Makabe, H. et al. *Journal of anesthesia* 26, 658-663, (2012); Dolinay, T. et al. *Am J Respir Crit Care Med* 185, 1225-1234 (2012)). Avian Influenza H5N1 and H7N9 contain proteins which generate an IFN-γ-biased cytokine storm by inhibiting IFN-α production and extensively activating NLRP3 inflammasome, which results in an excess of IL-18 and high IFN-γ levels. This IFN-γ cytokine profile characterizes ARDS pathogenesis (Guo, J. et al. *Scientific reports* 5, 10942 (2015); Peiris, J. S. et al. *Lancet* 363, 617-619 (2004)) and specifically, coronavirus associated ARDS (Huang, K. J. et al. *Journal of medical virology* 75, 185-194 (2005)). NLRP3 inhibition has demonstrated temporal protective effect in an Influenza A mouse model (Tate, M. D. et al. *Scientific reports* 6, 27912-27912 (2016)). In this study, NLRP3 early stage inhibition exacerbated the disease, which agrees with NLRP3 role in viral infection. NLRP3 inhibition in a later stage, where the disease reaches a peak, demonstrated amelioration in lung inflammation, indicating the importance of timing in treatment. In addition, research suggests IL-18 as a biomarker for acute lung injury. (Dolinay, T. et al. *Am J Respir Crit Care Med* 185, 1225-1234 (2012). Therefore, there is no doubt that IL-18 plays a key role in pulmonary autoinflammation which leads to acute lung injury and ARDS.

Blocking IL-18 Demonstrates Protective Effect in ALI

An IL-18 blocking agent has demonstrated amelioration in a mouse model for pulmonary fibrosis (Zhang, L. M. et al. *Biochemical and biophysical research communications* 508, 660-666 (2019)). In addition, it has been demonstrated in a rat model for acute lung injury (ALI) that anti-IL-18 neutralizing antibody ameliorates ALI (FIG. 2 of Jordan, J. A. et al. *Journal of immunology* 167, 7060-7068 (2001)). Moreover, IL-18BP has demonstrated protection against Acute Lung Injury (ALI) in a mouse model of LPS-induced ALI. (Zhang, L. M. et al. *Biochemical and Biophysical Research Communications* 505, 837-842 (2018)).

IL-18 in Hemophagocytic Lymphohistiocytosis (HLH)/Macrophage Activation Syndrome (MAS)

Secondary HLH or MAS may result from a complication of infection, lymphoma or a rheumatic disease. In humans and in cognate animal models, sHLH is associated with high proinflammatory cytokines of Th1 profile coined "cytokine storm." IFN-γ is thought to play a key role in sHLH associated cytokine storm, since IFN-γ inhibition demonstrates a protective effect in animal studies. (Jordan, M. B., et al. *Blood* 104, 735-743 (2004); Buatois, V. et al. *Translational Research* 180, 37-52 (2017)). IL-18's role in HLH is established. High levels of IL-18 were found in patients with primary and secondary HLH. (Mazodier, K. et al. *Blood* 106, 3483-3489 (2005); Maeno, N. et al. *Arthritis and Rheumatism* 50, 1935-1938 (2004); Shimizu, M. et al. *Clinical Immunology* 160, 277-281 (2015)). In one study, a theoretical free IL-18 (IL-18 not bound to IL-18BP) was calculated. As depicted in FIG. 3 of Mazodier, K. et al. *Blood* 106, 3483-3489 (2005), total IL-18 levels (free and IL-18BP bound) as well as free IL-18 levels were both high in HLH patients. The most convincing report of IL-18 neutralization for the treatment of HLH comes from a clinical trial in which IL-18BP was administered to an infant with HLH/MAS due to a mutation in an inflammasome (NLRC4), which demonstrated sustained response. (Canna, S. W. et al. *J Allergy Clin Immunol* 139, 1698-1701 (2017)). Overall, IL-18 plays an important role in driving sHLH by supporting IFN-γ cytokine storm, and its inhibition ameliorates sHLH in mouse models and most importantly, in humans.

IL-18 and Viral Infections

IL-18, capable of being Th1 inflammation driver, plays a role in viral immunity. In a mouse model of coronavirus infection, it has been shown that IL-18 has a protective role during viral infection (Zalinger, Z. B., et al. *Journal of Neurovirology* 23, 845-854 (2017)). It is well known that NLRP3 inflammasome can be overactivated in several respiratory diseases caused by viruses. (dos Santos, G., et al. *Am J Physiol-Lung C* 303, L627-633 (2012); Triantafilou, K. & Triantafilou, M. *Trends in Microbiology* 22, 580-588 (2014); McAuley, J. L. et al. *PLoS Pathog* 9 (2013)). Overactivation of NLRP3 inflammasome has shown to result in hyper activation of the immune system, which may have fatal consequences. Importantly, SARS-CoV patients demonstrate high levels of IL-18 serum levels compared to normal controls and IL-18 levels were higher in death group compared to survival group (Huang, K. J. et al. *Journal of Medical Virology* 75, 185-194 (2005)). Overall, understanding IL-18's role in driving IFN-γ cytokine storm in COVID-19 patients may be beneficial for patients with high serum IL-18 levels.

SUMMARY OF THE INVENTION

The present disclosure includes, for example, any one or a combination of the following embodiments:

Embodiment 1. A method of treating a condition associated with elevated IL-18, comprising administering to a subject in need thereof an effective amount of an anti-IL-18 antibody, optionally wherein the anti-IL-18 antibody comprises:

(a) a HCDR1 having an amino acid sequence of SEQ ID NO: 122;

(b) a HCDR2 having an amino acid sequence of SEQ ID NO: 123;

(c) a HCDR3 having an amino acid sequence of SEQ ID NO: 124;

(d) a LCDR1 having an amino acid sequence of SEQ ID NO: 126;

(e) a LCDR2 having an amino acid sequence of SEQ ID NO: 127; and (f) a LCDR3 having an amino acid sequence of SEQ ID NO: 128 and, wherein the condition associated with elevated IL-18 comprises any one or more of:

a. inflammation, optionally wherein the inflammation is hyperinflammation;

b. immune dysregulation that leads to multisystem organ failure;

c. acute lung injury (ALI), optionally wherein the ALI is associated with a bacterial or viral infection, including coronavirus infection;

d. acute respiratory distress syndrome (ARDS), optionally wherein the ARDS is associated with a bacterial or viral infection, including coronavirus infection;

e. hemophagocytic lymphohistiocytosis (HLH), optionally where the HLH is associated with a bacterial or viral infection, including coronavirus infection;

f. macrophage activation syndrome (MAS), optionally where the MAS is associated with a bacterial or viral infection, including coronavirus infection;

g. cytokine storm that drives tissue injury and vascular permeability;

h. post-infection pulmonary fibrosis;

i. syndromes caused by NLPR3 overactivation/dysregulation due to viral infection; and j. pneumonia, optionally wherein the pneumonia is associated with a bacterial or viral infection, including coronavirus infection, thereby treating the condition.

Embodiment 2. The method of embodiment 1, wherein the method further comprises the following steps prior to administering the anti-IL-18 antibody:

(a) contacting a biological sample isolated from the subject with an anti-IL-18 antibody;

(b) incubating the biological sample to allow an anti-IL-18 antibody to bind to IL-18; and (c) detecting the presence of complexes formed between an anti-IL-18 antibody and IL-18 in the biological sample.

Embodiment 3. The method of embodiment 2, wherein the detection of IL-18 indicates that treatment of the condition associated with elevated IL-18 with an anti-IL-18 antibody will be effective.

Embodiment 4. A method of treating COVID-19 infection comprising administering an anti-IL-18 antibody to a subject in need thereof.

Embodiment 5. A method of treating severe COVID-19 pneumonia comprising administering an anti-IL-18 antibody to a subject in need thereof.

Embodiment 6. A method of treating acute inflammatory disease, optionally associated with COVID-19, comprising administering an anti-IL-18 antibody to a subject in need thereof.

Embodiment 7. A method of treating respiratory failure associated with COVID-19 comprising administering an anti-IL-18 antibody to a subject in need thereof.

Embodiment 8. A method of treating cytokine storm comprising administering an anti-IL-18 antibody to a subject in need thereof.

Embodiment 9. A method of treating Acute Respiratory Distress Syndrome (ARDS), optionally associated with COVID-19, comprising administering an anti-IL-18 antibody to a subject in need thereof.

Embodiment 10. A method of treating hemophagocytic lymphohistiocytosis (HLH), optionally associated with COVID-19, comprising administering an anti-IL-18 antibody to a subject in need thereof.

Embodiment 11. A method of treating macrophage activation syndrome (MAS), optionally associated with COVID-19, comprising administering an anti-IL-18 antibody to a subject in need thereof.

Embodiment 12. A method of preventing progression to ARDS in a subject, comprising administering an anti-IL-18 antibody to the subject not yet having ARDS and having a condition associated with elevated IL-18.

Embodiment 13. A method of preventing the need for ventilation/intubation of a subject, comprising administering an anti-IL-18 antibody to the subject not yet intubated/ventilated and having a condition associated with elevated IL-18.

Embodiment 14. The method of any one of embodiments 4-13, wherein the anti-IL-18 antibody comprises:

(a) a HCDR1 having an amino acid sequence of SEQ ID NO: 122;

(b) a HCDR2 having an amino acid sequence of SEQ ID NO: 123;

(c) a HCDR3 having an amino acid sequence of SEQ ID NO: 124;

(d) a LCDR1 having an amino acid sequence of SEQ ID NO: 126;

(e) a LCDR2 having an amino acid sequence of SEQ ID NO: 127; and (f) a LCDR3 having an amino acid sequence of SEQ ID NO: 128.

Embodiment 15. The method of any one of the preceding embodiments, wherein the anti-IL-18 antibody comprises a VH domain having an amino acid sequence that is at least 90% identical to the full sequence of SEQ ID NO: 121.

Embodiment 16. The method of any one of the preceding embodiments, wherein the anti-IL-18 antibody comprises a VH domain having an amino acid sequence that is identical to the full sequence of SEQ ID NO: 121.

Embodiment 17. The method of any one of the preceding embodiments, wherein the anti-IL-18 antibody comprises a VL domain having an amino acid sequence that is at least 90% identical to the full sequence of SEQ ID NO: 125.

Embodiment 18. The method of any one of the preceding embodiments, wherein the anti-IL-18 antibody comprises a VL domain having an amino acid sequence that is identical to the full sequence of SEQ ID NO: 125.

Embodiment 19. The method of any one of the preceding embodiments, wherein the anti-IL-18 antibody comprises an antibody VH domain and an antibody VL domain, wherein the amino acid sequence of the antibody VH domain and the antibody VL domain are at least 90% identical to the full sequence of SEQ ID NOS: 121 and 125.

Embodiment 20. The method of any one of embodiments 1-3 or 15-19, wherein the condition associated with elevated IL-18 is secondary hemophagocytic lymphohistiocytosis (sHLH).

Embodiment 21. The method of any one of embodiments 1-3 or 15-19, wherein the condition associated with elevated IL-18 is a COVID-19 infection.

Embodiment 22. The method of embodiment 20, wherein the hemophagocytic lymphohistiocytosis (HLH) is secondary hemophagocytic lymphohistiocytosis (sHLH).

Embodiment 23. The method of any of the preceding embodiments, wherein the anti-IL-18 antibody administered to the subject suppresses T cell activation.

Embodiment 24. The method of any of the preceding embodiments, wherein the anti-IL-18 antibody administered to the subject suppresses increased expression of cytokines.

Embodiment 25. The method of embodiment 24, wherein the anti-IL-18 antibody administered to the subject suppresses increased expression of IFN-γ.

Embodiment 26. The method of any of the preceding embodiments, wherein the anti-IL-18 antibody administered to the subject reduces the subject's risk of mortality or morbidity.

Embodiment 27. The method of any one of the preceding embodiments, wherein the subject is human.

Embodiment 28. The method of any one of embodiments 1-3 or 15-19, wherein the subject has a respiratory disease, optionally caused by a coronavirus infection.

Embodiment 29. The method of any one of embodiments 1-3 or 15-19, wherein the subject has pneumonia.

Embodiment 30. The method of any one of embodiments 1-3 or 15-19, wherein the subject has acute lung injury (ALI).

Embodiment 31. The method of any one of embodiments 1-3 or 15-19, wherein the subject has acute respiratory distress syndrome (ARDS).

Embodiment 32. The method of any one of embodiments 1-3 or 15-19, wherein the subject has a mild coronavirus infection.

Embodiment 33. The method of any one of embodiments 1-3 or 15-19, wherein the subject has a moderate coronavirus infection.

Embodiment 34. The method of any one of embodiments 1-3 or 15-19, wherein the subject has a severe coronavirus infection.

Embodiment 35. The method of any one of embodiments 1-3 or 15-19, wherein the subject is at the Early Infection (Stage I) of a coronavirus infection.

Embodiment 36. The method of any one of embodiments 1-3 or 15-19, wherein the subject is at the Pulmonary Phase (Stage II) of a coronavirus infection.

Embodiment 37. The method of any one of embodiments 1-3 or 15-19, wherein the subject is at the Hyperinflammation Phase (Stage III) of a coronavirus infection.

Embodiment 38. The method of any one of the preceding embodiments, wherein the subject is a pediatric subject.

Embodiment 39. The method of any one of the preceding embodiments, wherein the subject is an adult.

Embodiment 40. A kit for use in a method of any one of the preceding embodiments comprising an anti-IL-18 antibody and reagents for carrying out the method.

DETAILED DESCRIPTION OF THE INVENTION

Figure 1:
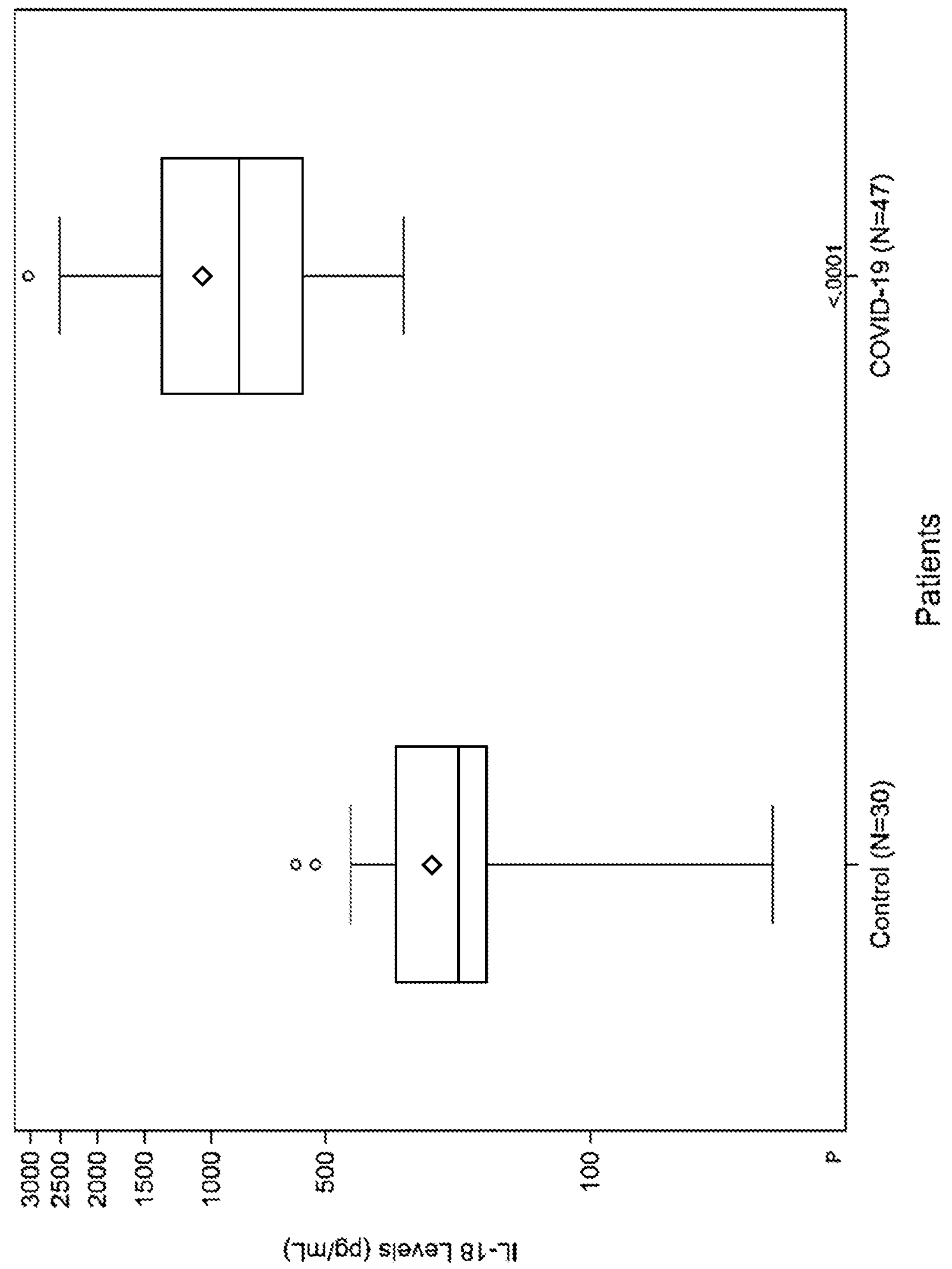
FIG. 1. Serum total IL-18 levels in hospitalized COVID-19 patients versus healthy controls. P-value was <0.0001 using the Kruskal-Wallis test (non-parametric one-way ANOVA), indicating higher IL-18 levels for COVID-19 patients versus controls.

The following definitions are provided to facilitate an understanding of the invention. They are not intended to limit the invention in any way.

Definitions

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an "isolated," or "biologically pure" molecule is a compound that has been removed from its natural milieu. As such, the terms "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

"Cytokine storm" herein refers to a dysregulated hyperinflammatory response manifested by the release of excessive (beyond normal levels) of pro-inflammatory cytokines and/or chemokines.

"Increased expression of cytokines" herein refers to expression of cytokines beyond normal levels.

"Increased expression of IFN-γ" as used herein refers to expression of IFN-γ beyond normal levels.

A "coronavirus," "corona respiratory virus," or "CoV" are used interchangeably herein to refer to a virus belonging to the family Coronaviridae. Coronaviruses are enveloped, positive-sense RNA viruses of approximately 31 Kb, making these viruses the largest known RNA viruses. Coronaviruses infect a variety of host species, including humans and several other vertebrates. These viruses predominantly cause respiratory and intestinal tract infections and induce a wide range of clinical manifestations. In general, coronaviruses can be classified into low pathogenic CoVs (including human CoVs (hCoVs)) and highly pathogenic CoVs, such as severe acute respiratory syndrome CoV (SARS-CoV) and Middle East respiratory syndrome CoV (MERS-CoV). Low pathogenic hCoV infect upper airways and cause seasonal mild to moderate cold-like respiratory illnesses in healthy individuals. In contrast, the highly pathogenic hCoVs (pathogenic hCoV) infect the lower respiratory tract and cause severe pneumonia, which sometimes leads to fatal acute lung injury (ALI) and acute respiratory distress syndrome (ARDS), resulting in high morbidity and mortality. COVID-19 is caused by infection with SARS-CoV2, which is a type of coronavirus. A coronavirus infection as used herein includes any of the above, if associated with coronavirus. “COVID-19 infection” used herein may also refer to a condition or disease caused by SARS-CoV2.

An “acute lung injury” or “ALI” herein refers to an acute lung disease with bilateral pulmonary infiltrate in a chest radiograph consistent with the presence of edema and no clinical evidence of left atrial hypertension; or (if measured) a pulmonary wedge pressure of 18 mmHg or less. Additionally, the ratio of arterial oxygen to the fraction of inspired oxygen (PaO2/FiO2) must be 300 mmHg or less, regardless of the level of positive end-expiratory pressure (PEEP).

“Acute respiratory distress syndrome” or “ARDS” herein refers to the most severe form of ALI, defined by a ratio of arterial oxygen to fraction of inspired oxygen of 200 mmHg or less. The term ARDS is often informally used interchangeably with ALI, but by strict criteria, ARDS should be reserved for the most severe form of the disease.

“Pulmonary fibrosis” herein refers to an interstitial lung disease that causes scarring of the lungs. The interstitial tissues are cells that make up the space between blood vessels and other structures inside the lungs. Pulmonary fibrosis with no known cause is called idiopathic pulmonary fibrosis.

“Hemophagocytic lymphohistiocytosis” or “HLH” is a potentially life-threatening clinical syndrome characterized by an unchecked and persistent activation of cytotoxic T lymphocytes and natural killer cells. Failure to control the immune response leads to increased secretion of inflammatory cytokines and macrophage activation, causing systemic inflammatory symptoms and signs. HLH is often classified as primary or familial (occurring in the presence of an underlying genetic predisposition) or as secondary or reactive (occurring in the absence of an underlying predisposing defect, typically in the setting of an infectious, malignant, or autoimmune trigger). “Secondary HLH” or “sHLH” is induced by a cytokine storm and is characterized by proliferation of macrophages causing lymphadenopathy. sHLH is also known as “macrophage activation syndrome” or “MAS.”

“IL-18” or “Interleukin-18” or “interferon-gamma inducing factor” or “IFN-γ-inducing factor” refers to a proinflammatory cytokine encoded by the IL18 gene that belongs to the IL-1 family of cytokines. Similar to IL-1β, it is synthesized as an inactive precursor called pro-IL-18 that is activated by cleavage by caspase-1. Pro-IL-18 is present in healthy cells and constitutively expressed by monocytes and epithelial cells. IL-18 has roles in stimulating both adaptive and innate immune response.

“Elevated IL-18” as used herein refers to a level of total IL-18 detected in a subject that is higher than a normal control. It is generally understood that “total” IL-18 is free IL-18 (IL-18 not bound to IL-18BP) plus IL-18 that is bound to IL-18BP. The normal control can be determined by those of skill in the art as applicable to the particular situation. In some instances, the normal control is an industry standard agreed upon by those of skill as being a level or range of levels that is typical of an individual without a IL-18-associated condition. In some instances, the normal control is a reference level of IL-18 from the same individual taken at a time point, and whether the subject has elevated IL-18 is determined based on a sample from that same individual taken at a different, typically later, time point.

The term “antibody” herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. As used herein, the term refers to a molecule comprising at least complementarity-determining region (CDR) 1, CDR2, and CDR3 of a heavy chain and at least CDR1, CDR2, and CDR3 of a light chain, wherein the molecule is capable of binding to antigen. As described herein, a “set of CDRs” comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a “set of CDRs” includes HCDRs and LCDRs. The term antibody includes, but is not limited to, fragments that are capable of binding antigen, such as Fv, single-chain Fv (scFv), Fab, Fab', and (Fab')2. The term antibody also includes, but is not limited to, chimeric antibodies, humanized antibodies, human antibodies, and antibodies of various species such as mouse, cynomolgus monkey, etc.

The term “heavy chain” refers to a polypeptide comprising at least a heavy chain variable region, with or without a leader sequence. In some embodiments, a heavy chain comprises at least a portion of a heavy chain constant region. The term “full-length heavy chain” refers to a polypeptide comprising a heavy chain variable region and a heavy chain constant region, with or without a leader sequence.

The term “heavy chain variable region” refers to a region comprising a heavy chain complementarity determining region (CDR) 1, framework region (FR) 2, CDR2, FR3, and CDR3 of the heavy chain. In some embodiments, a heavy chain variable region also comprises at least a portion of an FR1 and/or at least a portion of an FR4. In some embodiments, a heavy chain CDR1 corresponds to Kabat residues 31 to 35; a heavy chain CDR2 corresponds to Kabat residues 50 to 65; and a heavy chain CDR3 corresponds to Kabat residues 95 to 102. See, e.g., Kabat Sequences of Proteins of Immunological Interest (1987 and 1991, NIH, Bethesda, Md.).

The term “light chain” refers to a polypeptide comprising at least a light chain variable region, with or without a leader sequence. In some embodiments, a light chain comprises at least a portion of a light chain constant region. The term “full-length light chain” refers to a polypeptide comprising a light chain variable region and a light chain constant region, with or without a leader sequence. The term “light chain variable region” refers to a region comprising a light chain CDR1, FR2, HVR2, FR3, and HVR3. In some embodiments, a light chain variable region also comprises an FR1 and/or an FR4. In some embodiments, a light chain CDR1 corresponds to Kabat residues 24 to 34; a light chain CDR2 corresponds to Kabat residues 50 to 56; and a light chain CDR3 corresponds to Kabat residues 89 to 97. See, e.g., Kabat Sequences of Proteins of Immunological Interest (1987 and 1991, NIH, Bethesda, Md.).

A “chimeric antibody” refers to an antibody in which a portion of the heavy and/or light chain is derived from a particular source or species, while the remainder of the heavy and/or light chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species.

A "humanized antibody" refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is an Fab, an scFv, a (Fab')2, etc.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

The term "leader sequence" refers to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

The terms "inhibition" or "inhibit" refer to a decrease or cessation of any event (such as protein ligand binding) or to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. It is not necessary that the inhibition or reduction be complete. For example, in certain embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, or greater.

"Sample" or "subject sample" or "biological sample" generally refers to a sample which may be tested for a particular molecule. Samples may include but are not limited to cells, body fluids, including blood, serum, plasma, urine, saliva, stool, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the SNP containing nucleic acids described herein or their encoded proteins. Agents are evaluated for potential biological activity by inclusion in screening assays described hereinbelow.

A "subject" can be mammalian. In any of the embodiments involving a subject, the subject can be human. In any of the embodiments involving a subject, the subject can be a cow, pig, monkey, sheep, dog, cat, fish, or poultry.

A "pediatric" subject herein is a human of less than 18 years of age, whereas an "adult" subject is 18 years or older.

"Treatment" or "treat" refers to both therapeutic treatment and prophylactic or preventative measures. Those in need of treatment include those already with the disorder as well as those prone to have the disorder or those in which the disorder is to be prevented. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "effective amount" or "therapeutically effective amount" refers to an amount of a drug effective for treatment of a disease or disorder in a subject, such as to partially or fully relieve one or more symptoms. In some embodiments, an effective amount refers to an amount effective, at dosages and for periods of time necessary, to achieve the desired therapeutic or prophylactic result.

Identification of Biomarker IL-18

IL-18 is an important regulatory cytokine, which serves as a critical factor in orchestrating a cytokine storm and pulmonary failure associated with pathogen-mediated infection, including viral and bacterial infections including coronavirus (e.g., COVID-19).

In some embodiments, the anti-IL-18 antibody is an antibody neutralizing IL-18. In some embodiments, methods for detecting IL-18 in a subject's biological sample (e.g., serum or urine) are provided, wherein the results provide a basis for understanding whether an anti-IL-18 therapy may be provided and will be effective. In some embodiments, detection of IL-18 above a normal control indicates that an anti-IL-18 therapy may be provided and effective.

In some embodiments, the condition associated with elevated IL-18 with which the subject may be diagnosed is a coronavirus infection. In some embodiments, the coronavirus infection is a moderate or a severe coronavirus infection. In some embodiments, conditions associated with elevated IL-18 include any one or more of inflammation, optionally wherein the inflammation is hyperinflammation, immune dysregulation that leads to multisystem organ failure, acute lung injury (ALI), optionally wherein the ALI is associated with a bacterial or viral infection, including coronavirus infection, acute respiratory distress syndrome (ARDS), optionally wherein the ARDS is associated with a bacterial or viral infection, including coronavirus infection, hemophagocytic lymphohistiocytosis (HLH), optionally where the HLH is associated with a bacterial or viral infection, including coronavirus infection, macrophage activation syndrome (MAS), optionally where the MAS is associated with a bacterial or viral infection, including coronavirus infection, cytokine storm that drives tissue injury and vascular permeability, post-infection pulmonary fibrosis, and pneumonia, optionally wherein the pneumonia is associated with a bacterial or viral infection, including coronavirus infection. In some embodiments, the condition associated with elevated IL-18 is mild, moderate, or severe coronavirus infection, optionally wherein the coronavirus infection is a COVID-19 infection. In some embodiments, the COVID-19 infection is associated with ALI or ARDS in the subject. In some embodiments, the COVID-19 infection is associated with cytokine storm that drives tissue injury and vascular permeability in the lungs and post-infection pulmonary fibrosis. In some embodiments, the coronavirus infection is MERS-CoV, SARS-CoV, or SARS-CoV2/ COVID-19.

In some embodiments, methods for diagnosing a condition associated with elevated IL-18 in a subject are provided, wherein the level of IL-18 in a biological sample is detected. If the levels are above a normal control, then the subject is diagnosed as having a condition associated with elevated IL-18. In some embodiments, the condition associated with elevated IL-18 to be detected is cytokine storm. In some embodiments, the condition associated with elevated IL-18 to be detected is a virus infection. In some embodiments, the condition associated with elevated IL-18 is a coronavirus infection. In some embodiments, the condition associated with elevated IL-18 to be detected is a moderate or a severe coronavirus infection. In some embodiments, the condition associated with elevated IL-18 to be detected is a mild, moderate, or severe COVID-19 infection. In some embodiments, the COVID-19 infection is associated with ALI or ARDS in the subject. In some embodiments, the coronavirus infection is MERS-CoV or SARS-CoV.

In some embodiments, methods for detecting IL-18 in a biological sample from a subject may be conducted with a biological sample comprising blood, urine, serum, plasma, feces, or gastric lavage bodily fluid samples, or cell samples such as white blood cells or mononuclear cells.

In some embodiments, the method of detecting IL-18 in subject is performed by: contacting the biological sample with at least one anti-IL-18 antibody; incubating the biological sample to allow the anti-IL-18 antibody to bind to IL-18; and determining the presence of complexes formed between the anti-IL-18 antibody and IL-18 in the biological sample.

This method can further comprise the step of diagnosing the subject as having a condition associated with elevated IL-18 and/or administering an anti-IL-18 antibody.

Various methods known in the art for detecting specific antibody-antigen binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA), competition assay (e.g., Lateral Flow Immunoassay (LFIA)), and sandwich method.

An indicator moiety, or label group, can be attached to the subject antibodies and is selected to meet the needs of various uses of the method which are often dictated by the availability of assay equipment and compatible immunoassay procedures. Appropriate labels include, without limitation, radionuclides (for example 1251, 131I, 35S, 3H, or 32P), enzymes (for example, alkaline phosphatase, horseradish peroxidase, luciferase, or β-galactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif.).

General techniques to be used in performing the various immunoassays noted above are known to those of ordinary skill in the art.

ELISA assays are generally known to the skilled artisan and can be designed to determine serum IL-18 levels. In one exemplary embodiment, blood is collected, and the serum is isolated. If no kit is available, an ELISA can be developed using plates that are pre-coated with capture antibody specific for the IL-18 one is measuring. The plate is next incubated at room temperature for a period of time before washing. Enzyme-anti-IL-18 antibody conjugate is added and incubated. Unbound antibody conjugate is removed, and the plate washed before the addition of the chromogenic substrate solution that reacts with the enzyme. The plate is read on an appropriate plate reader at an absorbance specific for the enzyme and substrate used.

The competition method compares the competitive binding of an antigen in a sample and a known amount of a labeled antigen to the monoclonal antibody of the present invention. To carry out an immunological assay based on the competition method, a sample containing an unknown amount of the target antigen is added to a solid substrate to which the monoclonal antibody of the present invention is coated physically or chemically by known means, and the reaction is allowed to proceed. Simultaneously, a predetermined amount of the pre-labeled target antigen is added and the reaction is allowed to proceed. After incubation, the solid substrate is washed and the activity of the labeling agent bound to the solid substrate is measured.

In the sandwich method, the target antigen in a sample is sandwiched between the immobilized monoclonal antibody and the labeled monoclonal antibody, then a labeling substrate such as an enzyme is added, substrate color changes are detected, and thereby detecting the presence of the antigen. To carry out an immunological assay based on the sandwich method, for instance, a sample containing an unknown amount of the target antigen is added to a solid substrate to which the monoclonal antibody of the present invention is coated physically or chemically by known means, and the reaction is allowed to proceed. Thereafter, the labeled monoclonal antibody of the invention is added and the reaction is allowed to proceed. After incubation, the solid substrate is washed and the activity of the labeling agent bound to the solid substrate is measured.

In some embodiments, a first antibody is used for a diagnostic and a second antibody is used as a therapeutic. In some embodiments, the first and second antibodies are different. In some embodiments, the first and second antibodies can both bind to the antigen at the same time, by binding to separate epitopes.

Methods of Treating with Anti-IL-18 Antibody

The present invention provides a method of treating subjects having elevated IL-18, including subjects having a condition associated with elevated IL-18 with an anti-IL-18 antibody. In some embodiments, the anti-IL-18 antibody is an antibody neutralizing IL-18. In some embodiments, the condition associated with elevated IL-18 is a coronavirus infection. The treatment can be done with or without a diagnostic test for detecting elevated IL-18 in a subject's sample.

In some embodiments, a biological sample from the subject is first tested for the presence and level of IL-18 in a threshold step before the subject is treated. In such embodiments, the method of treating comprises contacting a biological sample from a subject with at least one first anti-IL-18 antibody, incubating the biological sample to allow the anti-IL-18 antibody to bind to IL-18, determining the presence of complexes formed between the anti-IL-18 antibody and IL-18 in the biological sample, and finally, based on the positive results of the detecting step and a finding of elevated IL-18, administering to the subject an effective amount of a second anti-IL-18 antibody, wherein the first and the second antibody differ.

In some embodiments, the subject is treated without a threshold testing step. In such cases, it may have been predetermined that the subject could benefit from an anti-IL-18 therapy or the anti-IL-18 antibody is being administered for prevention. In such embodiments, the method of treating comprises administering to a subject having a condition associated with elevated IL-18 an effective amount of an anti-IL-18 antibody.

In some embodiments of the method of treating, the condition associated with elevated IL-18 is a coronavirus infection. In some embodiments, the coronavirus infection is a COVID-19 infection. In some embodiments, the subject has a respiratory disease, optionally caused by a virus, bacteria or fungus. In some embodiments, the subject has a respiratory disease caused by coronavirus infection. In some embodiments, the subject has a respiratory disease caused by COVID-19. In some embodiments, the subject has pneumonia. In some embodiments, the subject has acute lung injury (ALI). In some embodiments, the subject has acute respiratory distress syndrome (ARDS). In some embodiments, the subject has hemophagocytic lymphohistiocytosis (HLH), which optionally is secondary hemophagocytic lymphohistiocytosis (sHLH). In some embodiments, the subject has macrophage activation syndrome (MAS). In some embodiments, pneumonia is associated with coronavirus infection. In some embodiments, ALI or ARDS is associated with coronavirus infection. In some embodiments, HLH or MAS is associated with coronavirus infection. In some embodiments, pneumonia is associated with COVID-19. In some embodiments, the subject has acute lung injury (ALI) associated with COVID-19. In some embodiments, the subject has acute respiratory distress syndrome (ARDS) associated with COVID-19. In some embodiments, the subject has hemophagocytic lymphohistiocytosis (HLH) associated with COVID-19. In some embodiments, the subject has macrophage activation syndrome (MAS) associated with COVID-19. In some embodiments, the subject has a mild coronavirus infection. In some embodiments, the subject has a moderate coronavirus infection. In some embodiments, the subject has a severe coronavirus infection. In some embodiments, a method of treating a severe COVID-19 infection, optional a COVID-19 pneumonia, is provided comprising administering an anti-IL-18 antibody to a subject in need thereof. In some embodiments, a method of treating an acute inflammatory disease, optionally associated with COVID-19, optionally a COVID-19 pneumonia, is provided comprising administering an anti-IL-18 antibody to a subject in need thereof. In some embodiments, a method of treating a respiratory failure, optionally associated with COVID-19, optionally a COVID-19 pneumonia, is provided comprising administering an anti-IL-18 antibody to a subject in need thereof. In some embodiments, a method of treating cytokine storm comprising administering an anti-IL-18 antibody to a subject in need thereof is provided. In some embodiments, the cytokine storm is the result of a coronavirus, e.g., COVID-19 infection. In some embodiments, a method of treating a dysregulated hyperimmune response (sometimes referred to as "cytokine storm") comprising administering an anti-IL-18 antibody to a subject in need thereof is provided. In some embodiments, a method of treating Acute Respiratory Distress Syndrome (ARDS) comprising administering an anti-IL-18 antibody to a subject in need thereof is provided. In some embodiments, a method of treating hemophagocytic lymphohistiocytosis (including secondary hemophagocytic lymphohistiocytosis (sHLH)) comprising administering an anti-IL-18 antibody to a subject in need thereof is provided. In some embodiments, a method of treating macrophage activation syndrome (MAS) comprising administering an anti-IL-18 antibody to a subject in need thereof is provided. In some embodiments, a method of treating syndromes caused by NLRP3 overactivation/dysregulation due to viral infection comprising administering an anti-IL-18 antibody to a subject in need thereof is provided.

In some embodiments, the administration of the anti-IL-18 antibody suppresses T cell activation. In some embodiments, the administration of the anti-IL-18 antibody suppresses increased expression of cytokines (e.g., a cytokine storm). IFN-γ is thought to play a key role in sHLH associated cytokine storm, since IFN-γ inhibition demonstrates a protective effect in animal studies. In some embodiments, the administration of the anti-IL-18 antibody suppresses increased expression of IFN-γ. In some embodiments, the administration of the anti-IL-18 antibody suppresses increased expression of cytokines (e.g., a cytokine storm) that is caused by a viral and/or bacterial infection, e.g., from a coronavirus infection. In some embodiments the administration of the anti-IL-18 antibody prevents or treats cytokine storm caused by a virus and/or bacterial infection, such as by a coronavirus infection. In some embodiments, the cytokine storm can drive tissue injury and vascular permeability in the lungs. Cytokine storm can lead to ARDS and ALI associated with coronavirus (e.g., COVID-19) infection. In some embodiments, the administration of the anti-IL-18 antibody prevents or treats post-infection pulmonary fibrosis, optionally associated with coronavirus infection. In some embodiments, the administration of the anti-IL-18 antibody reduces the subject's risk of mortality or morbidity. In some embodiments, the administration of the anti-IL-18 antibody prevents progression to ARDS in a subject with pneumonia associated with a coronavirus infection (e.g., COVID-19 infection). In some embodiments, the administration of the anti-IL-18 antibody prevents progression of ALI associated with a coronavirus infection, including (e.g., COVID-19 infection) to ARDS. In some embodiments, the administration of the anti-IL-18 antibody prevents or treats ARDS. In some embodiments, the administration of the anti-IL-18 antibody prevents the need for ventilation/intubation of the subject.

The methods of treating in the present invention may be carried out through conventional administration routes, including without limitation, the oral, buccal, sublingual, ocular, topical, parenteral, rectal, intracisternal, intravaginal, intraperitoneal, intravesical, local (e.g., powder, ointment, or drop), or nasal routes. The term "parenteral" includes subcutaneous, intravenous, intramuscular, or infusion. In certain embodiments, it may be appropriate to administer the agent in a continuous infusion or as a subcutaneous injection every day, every two or several days, or once a week, or every several weeks, or once a month, or once every several months, or at a time interval within a range defined by any two of the aforementioned intervals.

In some embodiments, the anti-IL-18 antibody is administered to a subject already receiving another therapy. In the case of a subject with COVID-19, the other therapy may be any therapy approved or being tested to treat or ameliorate a symptom of COVID-19. Such therapies include, but are not limited to, remdesivir, corticosteroids, and hydroxychloroquine. In some embodiments, the other therapy continues (on its normal course) during treatment with the anti-IL-18 antibody. In some embodiments, the other therapy is discontinued during treatment with the anti-IL-18 antibody. In some embodiments, the subject has COVID-19 and is receiving a high dose of corticosteroid and an anti-IL-18 antibody. In some embodiments, subject receiving the combination high dose corticosteroid and anti-IL-18 antibody have better outcomes than those not receiving the combination.

Stages of COVID-19 Disease Progression

The stages of COVID-19 Disease Progression are shown in FIG. 1 of Siddiqi, H. K., et al. COVID-19 illness in native and immunosuppressed states: A clinical-therapeutic staging proposal, *J Heart Lung Transplant* 39(5), 405-407 (2020), incorporated herein in its entirety. The disease can broadly be divided into three stages: Early Infection, Pulmonary Phase, and Hyperinflammation Phase. Stage I is the viral response phase, Stage III is the host inflammatory response phase, and Stage II is a combination of the two. As patients progress from Early Infection (Stage I) to the Pulmonary Phase (Stage II) at which pulmonary symptoms appear, the host inflammatory response emerges. It is at this point where, in some patients, dysregulation of the inflammatory response occurs. This dysregulation of the inflammatory response may be accompanied by elevated IL-18 levels in biological fluids, such as serum. This stage, the Pulmonary Phase, is the optimal stage at which to administer an anti-IL-18 antibody to correct this dysregulation and avert cytokine storm and progression to ARDS, which occurs in the Hyperinflammation Phase (Stage III).

Patients in Stage I of COVID-19 are considered to have mild disease. Patients in Stage II of COVID-19 are considered to have mild to moderate disease. Patients in Stage III of COVID-19 are considered to have severe disease.

In some embodiments, the anti-IL-18 antibody is administered to a subject with mild coronavirus infection (e.g., COVID-19). In some embodiments, the anti-IL-18 antibody is administered during the early infection stage of a coronavirus. In some embodiments, the anti-IL-18 antibody is administered during Stage I of a coronavirus infection. In some embodiments, the anti-IL-18 antibody is administered while the subject in need thereof has mild constitutional symptoms, a fever >99.6° F., dry cough, diarrhea, or headache. In some embodiments, the subject in need thereof has lymphopenia, increased prothrombin time, increased D-dimer and LDH (mild). In some embodiments, the administration of the anti-IL-18 antibody treats Stage I of a coronavirus infection. In some embodiments, the administration of the anti-IL-18 antibody prevents progression of the coronavirus infection to Stage II.

In some embodiments, the anti-IL-18 antibody of the method is administered to a subject with moderate coronavirus infection (e.g., COVID-19). In some embodiments, the anti-IL-18 antibody is administered during the Pulmonary Phase of a coronavirus infection. In some embodiments, the anti-IL-18 antibody is administered during Stage II of a coronavirus infection. In some embodiments of the invention, the anti-IL-18 antibody is administered during Stage HA or Stage IIB of a coronavirus infection. In some embodiments, the anti-IL-18 antibody is administered while the subject in need thereof is exhibiting shortness of breath or hypoxia. In some embodiments, the anti-IL-18 antibody is administered while the subject in need thereof meets the clinical criteria for ALI. In some embodiments, the subject in need thereof has abnormal chest imaging, transaminitis, or low-normal procalcitonin. In some embodiments, the patient is not ventilated/intubated. In some embodiments, the administration of the anti-IL-18 antibody treats Stage II of a coronavirus infection. In some embodiments, the administration of the anti-IL-18 antibody prevents progression of the coronavirus infection to Stage III.

In some embodiments, the anti-IL-18 antibody is administered to a subject with severe coronavirus infection (e.g., COVID-19). In some embodiments, the anti-IL-18 antibody is administered during the Hyperinflammation Phase of a coronavirus infection. In some embodiments, the anti-IL-18 antibody is administered during Stage III of a coronavirus infection. In some embodiments, the anti-IL-18 antibody is administered while the subject in need thereof has ARDS, systemic inflammatory response syndrome (SIRS)/Shock, or Cardiac Failure. SIRS is a complex immune response to insult characterized by widespread inflammation within the body. Both infectious and non-infectious causes of SIRS have been identified. In some embodiments, the patient is ventilated/intubated. In some embodiments, the administration of the anti-IL-18 antibody treats Stage III of a coronavirus infection.

Anti-IL-18 Antibodies

In some embodiments, an anti-IL-18 antibody is utilized for both the detection/diagnostic and therapeutic purposes described herein. In one embodiment, the anti-IL-18 antibody used for detection or diagnostic purposes is different from the antibody used for therapeutic purposes (even in the same subject).

The anti-IL-18 antibody useful for therapeutic purposes may comprise the CDR sequences or heavy and light chain variable regions of the antibodies disclosed in WO 2012/085015, which is incorporated herein by reference in its entirety. The antibodies of WO 2012/085015 referred to herein include Antibody 1, Antibody 1_GL, Antibody 2, Antibody 3, Antibody 4, Antibody 5, Antibody 6, Antibody 6_GL, Antibody 7, Antibody 7_GL, Antibody 8_GL, Antibody 9, Antibody 10, Antibody 11, Antibody 11_GL, and Antibody 12_GL. Antibody 12_GL is a fully human IgGiK monoclonal antibody (mAb) binding and neutralizing IL-18. Antibody 12_GL inhibits the formation of IL-18/Ra/R0 active complex in-vitro and in-vivo.

Antibody 12_GL demonstrates high affinity of 63 pM, which is 6 fold higher compared to IL-18's native inhibitor (IL-18 binding protein), and reduced Fc binding, to enable efficient anti-inflammatory role. As a fully human antibody, Antibody 12_GL is expected to demonstrate reduced anti-drug antibodies (ADA).

Antibody 12_GL demonstrates IL-18 neutralization and bioactivity by reducing IL-18's effects in various in vitro models with IC50 of sub nanomolar, and has proven efficient in COPD model (NHBE cells infected with Human Rhinovirus (HRV) by inhibiting IFN-γ release from PBMCs exposed to infected NHBE media). Antibody 12_GL has undergone 13 weeks IV toxicity studies complete with no toxicity up to 100 mg/Kg/week.

The anti-IL-18 antibody useful for therapeutic purposes may alternatively comprise the CDR sequences of other anti-IL-18 antibodies known in the art (see for example U.S. Pat. No. 6,706,487, WO 2001/058956, EP 1621616, US 2005/0147610; EP 0 974 600; and WO 0158956).

The anti-IL-18 antibody may alternatively comprise the CDR sequences or heavy and light chain variable regions of any of the antibodies disclosed in U.S. Pat. No. 8,133,978 B2, which is incorporated herein by reference in its entirety. The antibodies of U.S. Pat. No. 8,133,978 B2 referred to herein include the humanized anti-IL-18 antibodies referred to in claims 1 through 7 of U.S. Pat. No. 8,133,978 B2. In some embodiments, the anti-IL-18 antibody is GSK1070806, which is a humanized IgG1/kappa antibody that binds to human IL-18 with a high affinity (Kd=30.3 pM) and neutralizes its function. See, e.g., Reid, P. et al, Int J Clin Pharmacol Ther. 2014 October; 52(10):867-79. doi: 10.5414/CP202087.

In some embodiments, the anti-IL-18 antibody of the invention inhibits the binding of IL-18 to one or both of the IL-18 receptor (IL-18R, which comprises IL-18Rα/IL-18Rβ) and IL-18BP and thereby reduces IL-18 activity. In some embodiments, the anti-IL-18 antibody may bind to an epitope on the IL-18 molecule which wholly or partially overlaps the IL-18BP binding site.

For example, the anti-IL-18 antibody may specifically bind to an epitope of IL-18 which comprises one or more of residues Tyr1, Gly3, Leu5, Glu6, Lys8, Met51, Lys53, Asp54, Ser55, Gln56, Pro57, Arg58, Gly59, Met60, Arg104, Ser105 and Pro107 of human IL-18 or the corresponding residues from IL-18 of other species, for example a primate such as Rhesus macaque. The anti-IL-18 antibody may bind to an IL-18 epitope which comprises 1, 2, 3, 4, 5, 6, 7, 8, 9, 10, 11, 12, 13, 14, 15, 16 or all 17 residues selected from the group consisting of Tyr1, Gly3, Leu5, Glu6, Lys8, Met51, Lys53, Asp54, Ser55, Gln56, Pro57, Arg58, Gly59, Met60, Arg104, Ser105, and Pro107 of human IL-18.

In some embodiments, an anti-IL-18 antibody useful in the methods described herein may comprise one or more CDRs as described herein, e.g. a CDR3, and optionally also a CDR1 and CDR2 to form a set of CDRs. In some embodiments, the CDR or set of CDRs is a CDR or set of CDRs of any of Antibody 1, Antibody 1_GL, Antibody 2, Antibody 3, Antibody 4, Antibody 5, Antibody 6, Antibody 6_GL, Antibody 7, Antibody 7_GL, Antibody 8_GL, Antibody 9, Antibody 10, Antibody 11, Antibody 11_GL, and Antibody 12_GL, or may be a variant thereof as described herein.

In some embodiments:

HCDR1 may be about 7 amino acids long, comprising or consisting of Kabat residues 31-35b;

HCDR2 may be about 16 amino acids long, comprising or consisting of Kabat residues 50-65;

HCDR3 may be about 15 amino acids long, comprising or consisting of Kabat residues 95-102;

LCDR1 may be about 11 amino acids long, comprising or consisting of Kabat residues 24-34;

LCDR2 may be about 7 amino acids long, comprising or consisting of Kabat residues 50-56; and/or LCDR3 may be about 9 amino acids long, comprising or consisting of Kabat residues 89-97.

In some embodiments, the anti-IL-18 antibody comprises a HCDR1, HCDR2 and/or HCDR3 and/or an LCDR1, LCDR2 and/or LCDR3 as provided in Table 3 (the CDRs belonging to an individual antibody). The anti-IL-18 antibody may comprise a VH as described in any one of the antibodies in the Table 3. Optionally, it may also comprise a VL of any one of these antibodies. The VL may be from the same or a different antibody as the VH. A VH domain comprising a set of HCDRs of any of the antibodies listed in the Table 3, and/or a VL domain comprising a set of LCDRs of any of the antibodies listed in the Table 3, are also provided herein.

In some embodiments, the anti-IL-18 antibody comprises:

(a) a HCDR1 having an amino acid sequence identical to or comprising the amino acids of SEQ ID NO: 122;

(b) a HCDR2 having an amino acid sequence identical to or comprising the amino acids of SEQ ID NO: 123;

(c) a HCDR3 having an amino acid sequence identical to or comprising the amino acids of SEQ ID NO: 124;

(d) a LCDR1 having an amino acid sequence identical to or comprising the amino acids of SEQ ID NO: 126;

(e) a LCDR2 having an amino acid sequence identical to or comprising the amino acids of SEQ ID NO: 127; and (f) a LCDR3 having an amino acid sequence identical to or comprising the amino acids of SEQ ID NO: 128.

In some embodiments, the anti-IL-18 antibody comprises:

(a) a HCDR1 having an amino acid sequence identical to or comprising 1, 2, or 3 amino acid residue substitutions relative to SEQ ID NO: 122;

(b) a HCDR2 having an amino acid sequence identical to or comprising 1, 2, 3 or 4 amino acid residue substitutions relative to SEQ ID NO: 123;

(c) a HCDR3 having an amino acid sequence identical to or comprising 1, 2, 3, 4 or 5 amino acid residue substitutions relative to SEQ ID NO: 124;

(d) a LCDR1 having an amino acid sequence identical to or comprising 1, 2, 3 or 4 amino acid residue substitutions relative to SEQ ID NO: 126;

(e) a LCDR2 having an amino acid sequence identical to or comprising 1, 2, 3 or 4 amino acid residue substitutions relative to SEQ ID NO: 127; and (f) a LCDR3 having an amino acid sequence identical to or comprising 1, 2, 3, 4, 5, 6, 7, 8, or 9 amino acid residue substitutions relative to SEQ ID NO: 128.

In some embodiments, an anti-IL-18 antibody comprises a heavy chain and/or light chain of a parent antibody. In some embodiments, the anti-IL-18 antibody comprises any of the antibodies listed in the Table 3 with one or more substitutions within the CDRs. In some embodiments, the anti-IL-18 antibody comprises any of the antibodies listed in the Table 3 with one or more substitutions within the VH and/or VL. For example, an antibody molecule of the invention may comprise any one of Antibody 1, Antibody 1_GL, Antibody 2, Antibody 3, Antibody 4, Antibody 5, Antibody 6, Antibody 6_GL, Antibody 7, Antibody 7_GL, Antibody 8_GL, Antibody 9, Antibody 10, Antibody 11, Antibody 11_GL, and Antibody 12_GL, with 17, 16 or 15 or fewer substitutions, e.g. 14, 13, 12, 11, 10, 9, 8, 7, 6, 5, 4, 3, 2 or 1 substitutions within the VH and/or VL. Substitutions may potentially be made at any residue, including within the set of CDRs.

Typically, a VH domain is paired with a VL domain to provide an antibody antigen-binding site, although as discussed above a VH or VL domain alone may be used to bind antigen. For example, the Antibody 12_GL VH domain (SEQ ID NO: 121) may be paired with the Antibody 12_GL VL domain (SEQ ID NO:125), so that an antibody antigen-binding site is formed comprising both the Antibody 12_GL VH and VL domains. Analogous embodiments are provided for the VH and VL domains of the other antibodies disclosed herein.

In other embodiments, the Antibody 12_GL VH is paired with a VL domain other than that of Antibody 12_GL VL.

Light-chain promiscuity is well established in the art. Again, analogous embodiments are provided by the invention for the other VH and VL domains disclosed herein. Thus, the VH of the parent Antibody 1 or of any of the optimised clones Antibody 1_GL, Antibody 2, Antibody 3, Antibody 4, Antibody 5, Antibody 6, Antibody 6_GL, Antibody 7, Antibody 7_GL, Antibody 8_GL, Antibody 9, Antibody 10, Antibody 11, Antibody 11_GL, and Antibody 12_GL may be paired with a VL domain from a different antibody e.g. the VH and VL domains may be from different antibodies selected from Antibody 1, Antibody 1_GL, Antibody 2, Antibody 3, Antibody 4, Antibody 5, Antibody 6, Antibody 6_GL, Antibody 7, Antibody 7_GL, Antibody 8_GL, Antibody 9, Antibody 10, Antibody 11, Antibody 11_GL, and Antibody 12_GL.

In some embodiments, an anti-IL-18 antibody comprise a VH domain and a VL domain wherein;

(i) the VH domain amino acid sequence is shown in SEQ ID NO: 121 and the VL domain amino acid sequence is shown in SEQ ID NO: 125, (ii) the VH domain amino acid sequence has 1, 2, 3, 4, 5, 6, 7, 8, 9, 10, 11, 12, 13, 14 or 15 amino acid substitutions as compared to SEQ ID NO: 121 and the VL domain amino acid sequence has 1, 2, 3, 4, 5, 6, 7, 8, 9, 10, 11, 12 or 13 amino acid substitutions as compared to SEQ ID NO: 125; or (iii) the VH domain amino acid sequence has at least 80%, at least 85%, at least 90% or at least 95% sequence identity with SEQ ID NO: 121 and the VL domain amino acid sequence has at least 80%, at least 85%, at least 90% or at least 95% sequence identity with SEQ ID NO: 125.

In some embodiments, the anti-IL-18 antibody comprises a VH domain having an amino acid sequence which is at least 90% identical to the full sequence of SEQ ID NO: 121. In some embodiments, the anti-IL-18 antibody comprises a VH domain having an amino acid sequence which is identical to the full sequence of SEQ ID NO: 121. In some embodiments, the anti-IL-18 antibody comprises a VL domain having an amino acid sequence which is at least 90% identical to the full sequence of SEQ ID NO: 125. In some embodiments, the anti-IL-18 antibody comprises a VL domain having an amino acid sequence which is identical to the full sequence of SEQ ID NO: 125. In some embodiments, the anti-IL-18 antibody comprises an antibody VH domain and an antibody VL domain, wherein the amino acid sequence of the antibody VH domain and the antibody VL domain are at least 90% identical to the full sequence of SEQ ID NOS: 121 and 125.

In some embodiments, the anti-IL-18 antibody comprises a heavy chain and light chain comprising the following complementarity determining regions (CDRs):

(a) a HCDR1 comprising the amino acids of SEQ ID NO: 129;

(b) a HCDR2 comprising the amino acids of SEQ ID NO: 130;

(c) a HCDR3 comprising the amino acids of SEQ ID NO: 131;

(d) a LCDR1 comprising the amino acids of SEQ ID NO: 132;

(e) a LCDR2 comprising the amino acids of SEQ ID NO: 133; and (f) a LCDR3 comprising the amino acids of SEQ ID NO: 134.

In some embodiments, the anti-IL-18 antibody of the invention comprises: a heavy chain and light chain comprising the following complementarity determining regions (CDRs):

(a) a HCDR1 having an amino acid sequence identical to or comprising 1, 2, or 3 amino acid residue substitutions relative to SEQ ID NO: 129;

(b) a HCDR2 having an amino acid sequence identical to or comprising 1, 2, 3 or 4 amino acid residue substitutions relative to SEQ ID NO: 130;

(c) a HCDR3 having an amino acid sequence identical to or comprising 1, 2, 3, 4 or 5 amino acid residue substitutions relative to SEQ ID NO: 131;

(d) a LCDR1 having an amino acid sequence identical to or comprising 1, 2, 3 or 4 amino acid residue substitutions relative to SEQ ID NO: 132;

(e) a LCDR2 having an amino acid sequence identical to or comprising 1, 2, 3 or 4 amino acid residue substitutions relative to SEQ ID NO: 133; and (f) a LCDR3 having an amino acid sequence identical to or comprising 1, 2, 3, or 4 amino acid residue substitutions relative to SEQ ID NO: 134.

In some embodiments, the IL-18 antibody comprises a heavy chain having an amino acid sequence identical to or comprising 1 to 12 amino acid residue substitutions relative to a heavy chain selected from the group consisting of: SEQ ID NO: 137, SEQ ID NO: 145, and SEQ ID NO: 149; and a light chain having an amino acid sequence identical to or comprising 1 to 12 amino acid residue substitutions relative to a light chain selected from the group consisting of: SEQ ID NO: 141 and SEQ ID NO: 157. In some embodiments, the anti-IL-18 antibody further comprises substituting the residue at position 71 of the light chain with the corresponding residue found in a donor antibody from which the CDRs are derived. In some embodiments, the anti-IL-18 antibody comprises a tyrosine at position 71 of the light chain. In some embodiments, the anti-IL-18 antibody comprises a phenylalanine at position 71 of the light chain.

In one embodiment, the anti-IL-18 antibody comprises a heavy chain of SEQ ID NO: 137 and a light chain of SEQ ID NO: 141. In one embodiment, the anti-IL-18 antibody comprises a heavy chain of SEQ ID NO: 145 and a light chain of SEQ ID NO: 141. In one embodiment, the anti-IL-18 antibody comprises a heavy chain of SEQ ID NO: 149 and a light chain of SEQ ID NO: 141. In one embodiment, the anti-IL-18 antibody comprises a heavy chain of SEQ ID NO: 137 and a light chain of SEQ ID NO: 157. In one embodiment, the anti-IL-18 antibody comprises a heavy chain of SEQ ID NO: 145 and a light chain of SEQ ID NO: 157. In one embodiment, the anti-IL-18 antibody comprises a heavy chain of SEQ ID NO: 149 and a light chain of SEQ ID NO: 157. In one embodiment, the anti-IL-18 antibody comprises a heavy chain of SEQ ID NO: 137 and a light chain of SEQ ID NO: 153. In one embodiment, the anti-IL-18 antibody the anti-IL-18 antibody comprises a heavy chain of SEQ ID NO: 145 and a light chain of SEQ ID NO: 153. In one embodiment, the anti-IL-18 antibody the anti-IL-18 antibody comprises a heavy chain of SEQ ID NO: 149 and a light chain of SEQ ID NO: 153.

In some embodiments, the anti-IL-18 antibody may lack antibody constant regions, for example a scFv.

In other embodiments, anti-IL-18 antibody may comprise an antibody constant region. The anti-IL-18 antibody may be a whole antibody such as an IgG, i.e. an IgG1, IgG2, or IgG4, or may be an antibody fragment or derivative as described below. Antibody molecules can also have other formats, e.g. IgG1 with YTE (Dall'Acqua et al. (2002) *J.*

*Immunology,* 169: 5171-5180; Dall'Acqua et al. (2006) *J Biol. Chem.* 281(33):23514-24) and/or TM mutations (Oganesyan et al. (2008) *Acta Cryst D*64:700-4) in Fc region.

Another aspect of the invention provides an anti-IL-18 antibody comprising an antibody antigen binding site or antibody molecule as described herein which competes for binding to IL-18 with any antibody molecule which:

(i) binds IL-18 and (ii) comprises an antibody molecule, VH and/or VL domain, CDR e.g. HCDR3, and/or set of CDRs listed in the Table 3.

For example, in some embodiments, the anti-IL-18 antibody may compete with an antibody molecule comprising:

(i) a VH domain having the sequence of SEQ ID NO. 152 and a VL domain having the sequence of SEQ ID NO. 157;

(ii) a VH domain having a sequence with 15 or fewer amino acid substitutions such as 14, 13, 12, 11, 10, 9, 8, 7, 6, 5, 4, 3, 2, or 1 as compared to SEQ ID NO. 152; and a VL domain having a sequence with 13 or fewer amino acid substitutions such as 12, 11, 10, 9, 8, 7, 6, 5, 4, 3, 2, or 1 as compared to or SEQ ID NO. 157, or;

(iii) a VH domain and a VL domain having sequences with at least 90% sequence identity to SEQ ID NO. 152 and SEQ ID NO. 157, respectively.

Competition between anti-IL-18 antibodies may be assayed easily in vitro, for example using ELISA and/or by a biochemical competition assay such as one tagging a specific reporter molecule to one anti-IL-18 antibody which can be detected in the presence of one or more other untagged anti-IL-18 antibodies, to enable identification of anti-IL-18 antibodies which bind the same epitope or an overlapping epitope. Such methods are readily known to one of ordinary skill in the art and are described in more detail herein.

Variable domain amino acid sequence variants of any of the VH and VL domains whose sequences are specifically disclosed herein may be employed in accordance with the present invention.

As described above, aspects of the invention provide an anti-IL-18 antibody, comprising a VH domain that has at least 75%, at least 80%, at least 85%, at least 90%, at least 93%, at least 95%, at least 96%, at least 95%, at least 97%, at least 98% or at least 99% amino acid sequence identity with a VH domain of any of the antibodies listed herein, for which VH domain sequences are shown in the appended Table 3 below; and/or comprising a VL domain that has at least 75%, at least 80%, at least 85%, at least 90%, at least 93%, at least 95%, at least 96%, at least 95%, at least 97%, at least 98% or at least 99% amino acid sequence identity with a VL domain of any of the antibodies listed herein, for which VL domain sequences are shown in the appended Table 3 below.

Aspects of the invention provide an anti-IL-18 antibody comprising a VH domain having a set of VH CDRs that have at least 75%, at least 80%, at least 85%, at least 90%, at least 93%, at least 95%, at least 96%, at least 95%, at least 97%, at least 98% or at least 99% amino acid sequence identity with the set of VH CDRs of any of the antibodies listed herein, for which VH CDR sequences are shown in the appended Table 3; and/or comprising a VL domain having a set of VL CDRs that have at that has at least 75%, at least 80%, at least 85%, at least 90%, at least 93%, at least 95%, at least 96%, at least 95%, at least 97%, at least 98% or at least 99% amino acid sequence identity with the set of VL CDRs of any of the antibodies listed herein, for which the VL CDR sequences are shown in the appended Table 3.

Algorithms that can be used to calculate % identity of two amino acid sequences are known in the art and include e.g. BLAST [Altschul et al. (1990) *J. Mol. Biol.* 215: 405-410], FASTA [Pearson and Lipman (1988) *PNAS USA* 85: 2444-2448], or the Smith-Waterman algorithm [Smith and Waterman (1981) *J. Mol Biol.* 147: 195-197] e.g. employing default parameters.

Kits and Articles of Manufacture

Any of the aforementioned methods can be implemented via kits for the detection of IL-18 and/or the diagnosis and/or treatment of a condition associated with elevated IL-18, including a viral and/or bacterial infection, such as a coronavirus, including COVID-19. The kit may contain an antibody, one or more non-naturally occurring detectable labels, marker, or reporter, a pharmaceutically acceptable carrier, a physiologically acceptable carrier, instructions for use, a container, a vessel for administration, an assay substrate, or any combination thereof.

In some embodiments, the kit is for use in a method of detecting IL-18 in a biological sample.

In some embodiments, the kit is for use in a method of detecting IL-18 in a biological sample from a subject having or suspected of having coronavirus infection, ALI, ARDS, or pulmonary fibrosis.

In some embodiments, the kit is for use in method of detecting elevated IL-18 in a biological sample from a subject, optionally wherein the subject is suspected of having a coronavirus infection and also for treating the subject after diagnosis by administering an anti-IL-18 antibody in an effective amount.

In some embodiments, the kit for use in one of the above methods is suitable for a subject with a mild, moderate, or severe coronavirus infection. In some embodiments, the mild, moderate, or severe coronavirus infection is a COVID-19 infection. In some embodiments, the coronavirus (including COVID-19) infection is associated with respiratory disease. In some embodiments, the coronavirus (including COVID-19) infection is associated with ALI or ARDS.

In some embodiments, the kit for use in a method of detecting and/or treating comprises a solid phase to which the anti-IL-18 antibody reagent is attached. In some embodiments, the kit for use in a method of detecting and/or treating comprises a solid phase to which IL-18 derived from the biological sample will be attached.

The solid phase to be used in the kits of the present invention includes, but is not limited, to microplates, magnetic particles, filter papers for immunochromatography, polymers such as polystyrene, glass beads, glass filters and other insoluble carriers. In one embodiment, a solid substrate containing many compartments or regions has at least one compartment coated with antibodies of the invention.

The kits of the invention may also include a further component to the diagnostic agent, the anti-IL-18 antibody. The further component may include, but is not limited, to enzymes for labeling, substrates therefor, radioisotopes, light-reflecting substances, fluorescent substances, colored substances, buffer solutions, and plates, and those mentioned herein above.

Example 1

COVID-19 patients demonstrate cytokine storm hyperinflammation disorders such as ARDS and sHLH which are strongly driven by IL-18. Moreover, IL-18 has a well-characterized proinflammatory role in ARDS and IFN-γ-related cytokine storm, which has been demonstrated to ameliorate when using IL-18 neutralizing agents.

The information herein can be applied clinically to subjects for determining whether an anti-IL-18 therapy could be beneficial for subjects with coronavirus infection, such as COVID-19, or a respiratory disease associated with coronavirus infection, such as ALI/ARDS or sHLH/MAS.

A small study was conducted in which serum from subjects with acute COVID-19 infections was tested to determine the levels of total IL-18 and other cytokines/inflammatory markers during the acute phase of the illness. Whether there are differences in IL-18 levels and other inflammatory markers in healthy controls versus subjects with mild to severe disease with or without ALI/ARDS was determined. Given IL-18's role in mediating immune response, particularly its roles in driving innate and adaptive inflammation by, for example, inducing IFN-γ secretion from T cells, NK cells, NKT cells, B cells, DC and macrophages, these subjects are expected to benefit from anti-IL-18 antibody therapy. Thus, the assay results were expected to provide the clinician with guidance as to which therapeutic agents are appropriate.

The study was conducted and included 30 healthy controls, 28 subjects who were intubated and had severe COVID-19 infection, and 20 subjects who were non-ventilated and had mild to moderate COVID-19 infection. Blood was drawn from the subjects at a single timepoint. Using the Myriad RBM InflammationMAP™ Assay v1.0, which is microsphere-based and consists of using antigen-specific antibodies optimized in a capture-sandwich format, the presence and level of total IL-18 in the blood serum was determined; the determination took place upon intubation for intubated patients.

IL-18 was significantly ($p<0.0001$) elevated in COVID-19 subjects (N=47) as compared to healthy controls (N=30). See FIG. 1.

Figure 2:
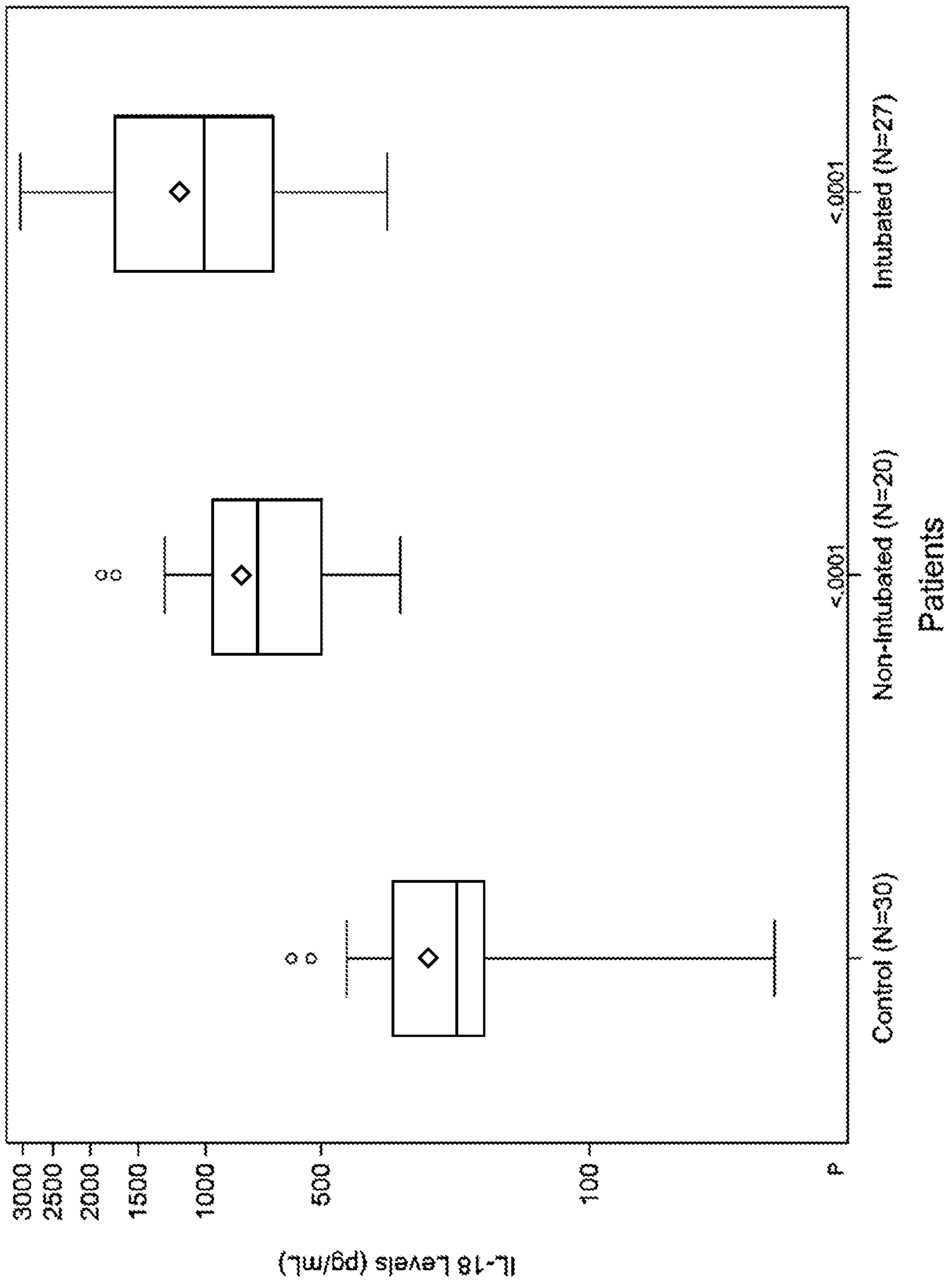
FIG. 2. Serum total IL-18 levels in non-intubated and intubated COVID-19 patients versus healthy controls. P-values for both tests were <0.0001 using the Kruskal-Wallis test (non-parametric one-way ANOVA).

IL-18 was also significantly ($p<0.0001$) elevated in serum of non-ventilated (intubated) COVID-19 patients (N=20) and intubated COVID-19 patients (N=27) as compared to healthy controls (N=30). See FIG. 2.

Figure 3:
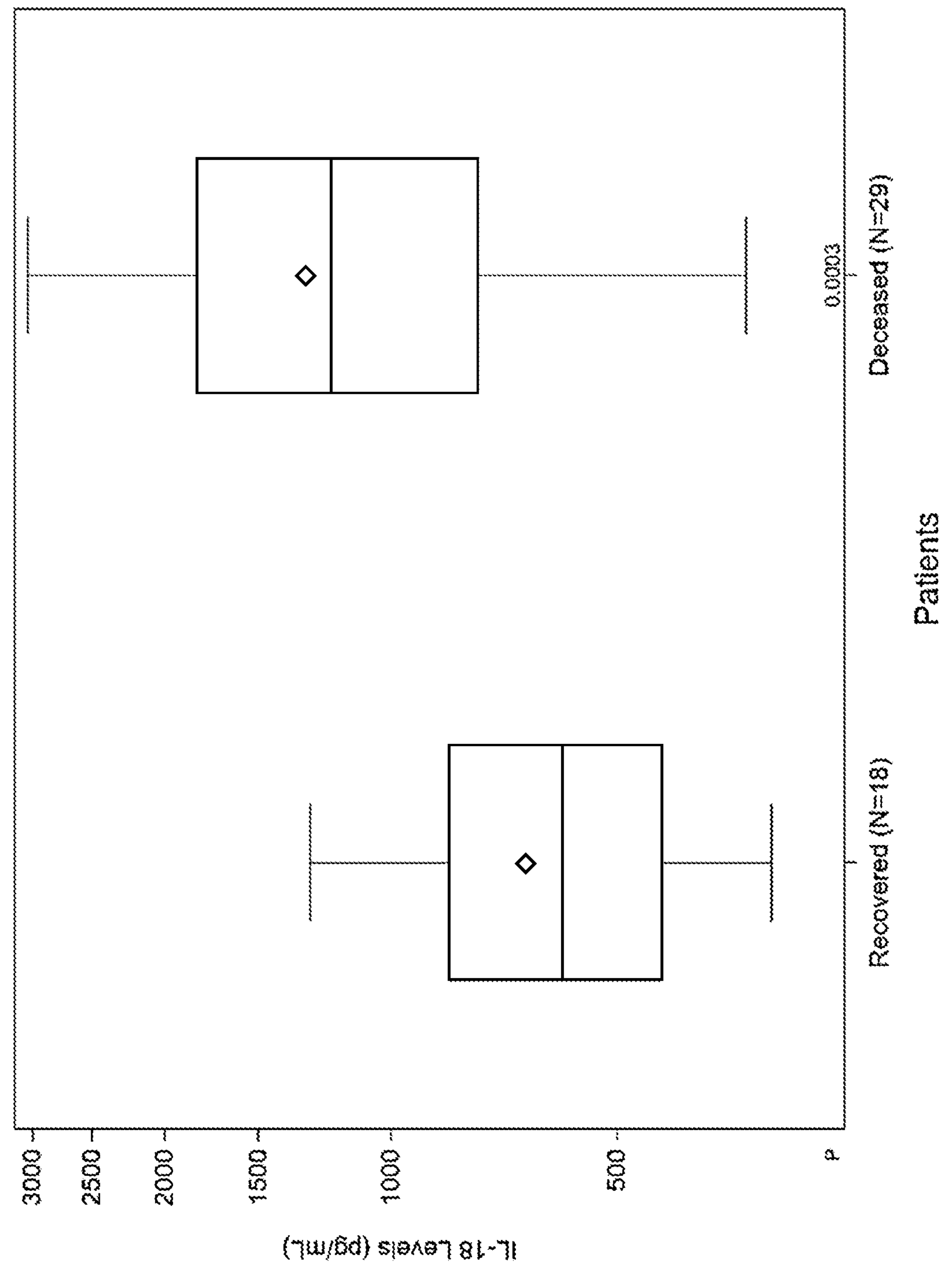
FIG. 3. Serum total IL-18 levels in deceased COVID-19 patients versus recovered COVID-19 patients. P-value for deceased COVID-19 patients was 0.0003 using the Kruskal-Wallis test (non-parametric one-way ANOVA) relative to recovered COVID-19 patients.

IL-18 was also significantly ($p=0.0003$) elevated in serum of deceased COVID-19 patients (N=18) as compared to recovered COVID-19 patients (N=29). See FIG. 3.

Example 2

Total IL-18 testing was performed using the Myriad RBM InflammationMAP™ Assay v1.0 on samples from ARDS patients and compared to healthy control total IL-18 levels. The samples were from patients with acute lung injury and acute respiratory distress syndrome who were enrolled in a multicenter, randomized trial. Patients were enrolled from 24 hospitals at the 10 centers constituting the ARDS Clinical Trials Network. Patients were eligible for the study if they were in an ICU, required positive pressure ventilation, and had acute onset of significantly impaired oxygenation with a PaO2-to-fraction of inspired oxygen (FIO2) ratio less than or equal to 300 (adjusted for barometric pressure), bilateral infiltrates consistent with pulmonary edema on a frontal chest radiograph, and no clinical evidence of left atrial hypertension. Patients had to be enrolled within 36 hours of developing these criteria. The serum samples were taken at baseline, Day 0, with blood drawn into EDTA-anticoagulated tubes, centrifuged, and frozen at −70 C.

Figure 4:
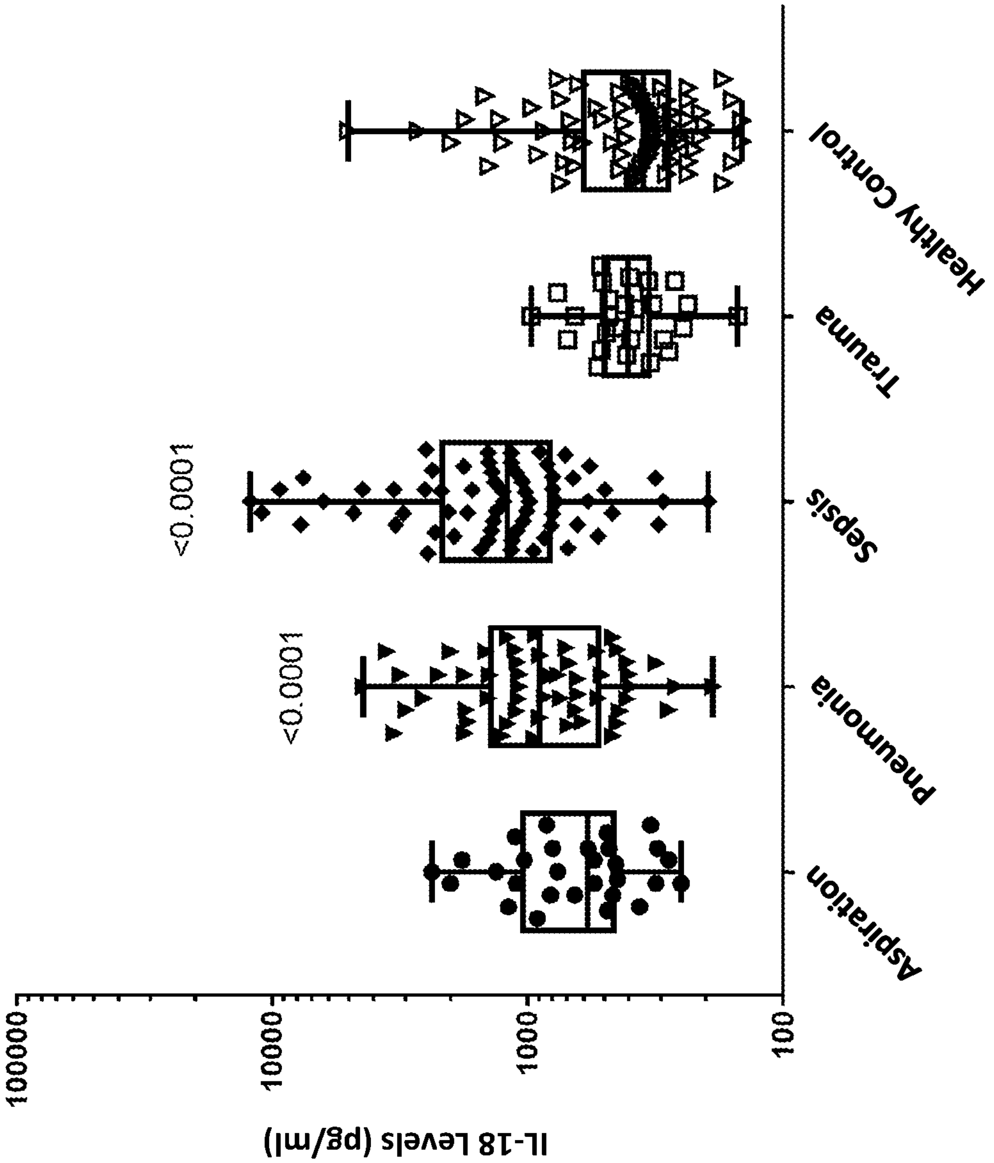
FIG. 4 shows a box plot generated from data from IL-18 testing using the Myriad RBM InflammationMAP™ Assay v1.0 performed on samples from ARDS patients and compared to healthy control IL-18 levels. The box plot shows total IL-18 levels for ARDS patients separated by different causes of ARDS: aspiration, pneumonia, sepsis, or trauma. There are 79 healthy control data points. P-values were calculated using the non paired t-test using Graphpad Prism.

The preliminary data shows elevated total IL-18 levels in the ARDS population compared to healthy control levels. A box plot generated on this data is shown in FIG. 4. The box plot shows total IL-18 levels for ARDS patients separated by different causes of ARDS: aspiration, pneumonia, sepsis, or trauma. It also shows total IL-18 levels for 79 healthy control samples.

Table 1 shows the average total IL-18 levels in healthy control samples and ARDS samples in pg/ml. The ARDS samples are divided by the cause of ARDS. Standard deviation is also shown for each.

TABLE 1

Total IL-18 Levels in ARDS and Healthy Control Samples

| Sample Type | No. of Samples | Average IL-18 Level (pg/ml) | Standard Deviation (pg/ml) |
|---|---|---|---|
| Healthy Control (HC) | 79 | 505.93 | 420.37 |
| Aspiration | 12 | 752.75 | 372.63 |
| Aspiration Pneumonia | 13 | 827.82 | 632.15 |
| Pneumonia | 55 | 1159.65 | 919.50 |
| Sepsis | 32 | 2009.44 | 2524.87 |
| Sepsis Pneumonia | 30 | 2321.47 | 2563.40 |
| Trauma | 28 | 438.29 | 174.04 |

Table 2 shows the fold change between the average total IL-18 level for the healthy control samples compared to ARDS samples divided by cause of ARDS. For example, "1.49" in the first row for "Aspiration" indicates that the average total IL-18 level for the aspiration ARDS samples was 1.49-fold higher than the average total IL-18 level for the healthy control samples.

TABLE 2

Fold Change for Healthy Controls

| Cause of ARDS | Fold Change Compared to Healthy Control IL-18 Levels |
|---|---|
| Aspiration | 1.49 |
| Aspiration Pneumonia | 1.64 |
| Pneumonia | 2.29 |
| Sepsis | 3.97 |
| Sepsis Pneumonia | 4.59 |
| Trauma | 0.87 |

The following table provides the sequences referred to in this application.

TABLE 3

Table of Sequences

| SEQ ID NO | DESCRIPTION | SEQUENCE |
|---|---|---|
| 1 | Antibody 1 VH | Gln Val Gln Leu Gln Gln Ser Gly Pro Arg Leu Val Lys Pro Ser Gln Thr Leu Ser Leu Thr Cys Thr Val Ser Gly Gly Ser Ile Ser Ser Gly Gly Tyr Tyr Trp Ser Trp Ile Arg Gln Pro Ala Gly |

TABLE 3-continued

Table of Sequences

| SEQ ID NO | DESCRIPTION | SEQUENCE |
|---|---|---|
| | | Lys Gly Leu Glu Trp Ile Gly Ser Ile Tyr Tyr Ser Gly Ser Thr Tyr Tyr Asn Pro Ser Leu Lys Ser Arg Val Thr Ile Ser Gly Asp Thr Pro Lys Asn Gln Phe Ser Leu Lys Leu Ser Ser Val Thr Ala Ala Asp Thr Ala Val Tyr Tyr Cys Ala Arg Thr Pro Ala Tyr Asp Gly Asp Ala Arg Ala Asp Phe Phe Asp Val Trp Gly Arg Gly Thr Leu Val Thr Val Ser Ser |
| 2 | Antibody 1 HCDR1 | Ser Gly Gly Tyr Tyr Trp Ser |
| 3 | Antibody 1 HCDR2 | Ser Ile Tyr Tyr Ser Gly Ser Thr Tyr Tyr Asn Pro Ser Leu Lys Ser |
| 4 | Antibody 1 HCDR3 | Thr Pro Ala Tyr Asp Gly Asp Ala Arg Ala Asp Phe Phe Asp Val |
| 5 | Antibody 1 VL | Asp Ile Val Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Arg Ala Pro Lys Val Leu Ile Tyr Lys Ala Ser Thr Leu Glu Ser Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Gln Gln Ser Tyr Ser Thr Pro Trp Thr Phe Gly Gln Gly Thr Lys Leu Glu Ile Lys |
| 6 | Antibody 1 LCDR1 | Arg Ala Ser Gln Gly Ile Ser Ser Trp Leu Ala |
| 7 | Antibody 1 LCDR2 | Lys Ala Ser Thr Leu Glu Ser |
| 8 | Antibody 1 LCDR3 | Gln Gln Ser Tyr Ser Thr Pro Trp Thr |
| 9 | Antibody 1_GL VH | Gln Val Gln Leu Gln Glu Ser Gly Pro Gly Leu Val Lys Pro Ser Glu Thr Leu Ser Leu Thr Cys Thr Val Ser Gly Gly Ser Ile Ser Ser Gly Gly Tyr Tyr Trp Ser Trp Ile Arg Gln Pro Pro Gly Lys Gly Leu Glu Trp Ile Gly Ser Ile Tyr Tyr Ser Gly Ser Thr Tyr Tyr Asn Pro Ser Leu Lys Ser Arg Val Thr Ile Ser Gly Asp Thr Ser Lys Asn Gln Phe Ser Leu Lys Leu Ser Ser Val Thr Ala Ala Asp Thr Ala Val Tyr Tyr Cys Ala Arg Thr Pro Ala Tyr Asp Gly Asp Ala Arg Ala Asp Phe Phe Asp Val Trp Gly Arg Gly Thr Leu Val Thr Val Ser Ser |
| 10 | Antibody 1_GL HCDR1 | Ser Gly Gly Tyr Tyr Trp Ser |
| 11 | Antibody 1_GL HCDR2 | Ser Ile Tyr Tyr Ser Gly Ser Thr Tyr Tyr Asn Pro Ser Leu Lys Ser |
| 12 | Antibody 1_GL HCDR3 | Thr Pro Ala Tyr Asp Gly Asp Ala Arg Ala Asp Phe Phe Asp Val |
| 13 | Antibody 1_GL VL | Asp Ile Gln Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Lys Ala Pro Lys Val Leu Ile Tyr Lys Ala Ser Thr Leu Glu Ser Gly Val Pro Ser Arg Phe Ser Gly Ser Gly Ser Gly Thr Glu Phe Thr Leu Thr Ile Ser Ser Leu Gln Pro Asp Asp Phe Ala Thr Tyr Tyr Cys Gln Gln Ser Tyr Ser Thr Pro Trp Thr Phe Gly Gln Gly Thr Lys Leu Glu Ile Lys |
| 14 | Antibody 1_GL LCDR1 | Arg Ala Ser Gln Gly Ile Ser Ser Trp Leu Ala |
| 15 | Antibody 1_GL LCDR2 | Lys Ala Ser Thr Leu Glu Ser |
| 16 | Antibody 1_GL LCDR3 | Gln Gln Ser Tyr Ser Thr Pro Trp Thr |

TABLE 3-continued

Table of Sequences

| SEQ ID NO | DESCRIPTION | SEQUENCE |
|---|---|---|
| 17 | Antibody 2 VH | Gln Val Gln Leu Gln Gln Ser Gly Pro Arg Leu Val Lys Pro Ser Gln Thr Leu Ser Leu Thr Cys Thr Val Ser Gly Gly Ser Ile Ser Ser Gly Gly Tyr Tyr Trp Ser Trp Ile Arg Gln Pro Ala Gly Lys Gly Leu Glu Trp Ile Gly Ser Ile Tyr Tyr Ser Gly Ser Thr Tyr Tyr Asn Pro Ser Leu Lys Ser Arg Val Thr Ile Ser Gly Asp Thr Pro Lys Asn Gln Phe Ser Leu Lys Leu Ser Ser Val Thr Ala Ala Asp Thr Ala Val Tyr Tyr Cys Ala Arg Thr Pro Ala Tyr Asp Gly Asp Ala Arg Ala Asp Phe Phe Asp Val Trp Gly Arg Gly Thr Leu Val Thr Val Ser Ser |
| 18 | Antibody 2 HCDR1 | Ser Gly Gly Tyr Tyr Trp Ser |
| 19 | Antibody 2 HCDR2 | Ser Ile Tyr Tyr Ser Gly Ser Thr Tyr Tyr Asn Pro Ser Leu Lys Ser |
| 20 | Antibody 2 HCDR3 | Thr Pro Ala Tyr Asp Gly Asp Ala Arg Ala Asp Phe Phe Asp Val |
| 21 | Antibody 2 VL | Asp Ile Val Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Arg Ala Pro Lys Val Leu Ile Tyr Lys Ala Ser Thr Leu Glu Ser Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Gln Asp Ile Ser Phe Pro Pro Trp Thr Phe Gly Gln Gly Thr Lys Leu Glu Ile Lys |
| 22 | Antibody 2 LCDR1 | Arg Ala Ser Gln Gly Ile Ser Ser Trp Leu Ala |
| 23 | Antibody 2 LCDR2 | Lys Ala Ser Thr Leu Glu Ser |
| 24 | Antibody 2 LCDR3 | Gln Asp Ile Ser Phe Pro Pro Trp Thr |
| 25 | Antibody 3 VH | Gln Val Gln Leu Gln Gln Ser Gly Pro Arg Leu Val Lys Pro Ser Gln Thr Leu Ser Leu Thr Cys Thr Val Ser Gly Gly Ser Ile Ser Ser Gly Gly Tyr Tyr Trp Ser Trp Ile Arg Gln Pro Ala Gly Lys Gly Leu Glu Trp Ile Gly Ser Ile Tyr Tyr Ser Gly Ser Thr Tyr Tyr Asn Pro Ser Leu Lys Ser Arg Val Thr Ile Ser Gly Asp Thr Pro Lys Asn Gln Phe Ser Leu Lys Leu Ser Ser Val Thr Ala Ala Asp Thr Ala Val Tyr Tyr Cys Ala Arg Thr Pro Ala Tyr Asp Gly Asp Ala Arg Ala Asp Phe Phe Asp Val Trp Gly Arg Gly Thr Leu Val Thr Val Ser Ser |
| 26 | Antibody 3 HCDR1 | Ser Gly Gly Tyr Tyr Trp Ser |
| 27 | Antibody 3 HCDR2 | Ser Ile Tyr Tyr Ser Gly Ser Thr Tyr Tyr Asn Pro Ser Leu Lys Ser |
| 28 | Antibody 3 HCDR3 | Thr Pro Ala Tyr Asp Gly Asp Ala Arg Ala Asp Phe Phe Asp Val |
| 29 | Antibody 3 VL | Asp Ile Val Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Arg Ala Pro Lys Val Leu Ile Tyr Lys Ala Ser Thr Leu Glu Ser Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Gln Gln Ser Leu Tyr Pro Pro Trp Thr Phe Gly Gln Gly Thr Lys Leu Glu Ile Lys |
| 30 | Antibody 3 LCDR1 | Arg Ala Ser Gln Gly Ile Ser Ser Trp Leu Ala |
| 31 | Antibody 3 LCDR2 | Lys Ala Ser Thr Leu Glu Ser |

TABLE 3-continued

Table of Sequences

| SEQ ID NO | DESCRIPTION | SEQUENCE |
|---|---|---|
| 32 | Antibody 3 LCDR3 | Gln Gln Ser Leu Tyr Pro Pro Trp Thr |
| 33 | Antibody 4 VH | Gln Val Gln Leu Gln Gln Ser Gly Pro Arg Leu Val Lys Pro Ser Gln Thr Leu Ser Leu Thr Cys Thr Val Ser Gly Gly Ser Ile Ser Ser Gly Gly Tyr Tyr Trp Ser Trp Ile Arg Gln Pro Ala Gly Lys Gly Leu Glu Trp Ile Gly Ser Ile Tyr Tyr Ser Gly Ser Thr Tyr Tyr Asn Pro Ser Leu Lys Ser Arg Val Thr Ile Ser Gly Asp Thr Pro Lys Asn Gln Phe Ser Leu Lys Leu Ser Ser Val Thr Ala Ala Asp Thr Ala Val Tyr Tyr Cys Ala Arg Thr Pro Ala Tyr Asp Gly Asp Ala Arg Ala Asp Phe Phe Asp Val Trp Gly Arg Gly Thr Leu Val Thr Val Ser Ser |
| 34 | Antibody 4 HCDR1 | Ser Gly Gly Tyr Tyr Trp Ser |
| 35 | Antibody 4 HCDR2 | Ser Ile Tyr Tyr Ser Gly Ser Thr Tyr Tyr Asn Pro Ser Leu Lys Ser |
| 36 | Antibody 4 HCDR3 | Thr Pro Ala Tyr Asp Gly Asp Ala Arg Ala Asp Phe Phe Asp Val |
| 37 | Antibody 4 VL | Asp Ile Val Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Arg Ala Pro Lys Val Leu Ile Tyr Lys Ala Ser Thr Leu Glu Ser Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Gln Gln Ser His His Pro Asn Trp Asp Phe Gly Gln Gly Thr Lys Leu Glu Ile Lys |
| 38 | Antibody 4 LCDR1 | Arg Ala Ser Gln Gly Ile Ser Ser Trp Leu Ala |
| 39 | Antibody 4 LCDR2 | Lys Ala Ser Thr Leu Glu Ser |
| 40 | Antibody 4 LCDR3 | Gln Gln Ser His His Pro Asn Trp Asp |
| 41 | Antibody 5 VH | Gln Val Gln Leu Gln Gln Ser Gly Pro Arg Leu Val Lys Pro Ser Gln Thr Leu Ser Leu Thr Cys Thr Val Ser Gly Gly Ser Ile Ser Ser Gly Gly Tyr Tyr Trp Ser Trp Ile Arg Gln Pro Ala Gly Lys Gly Leu Glu Trp Ile Gly Ser Ile Tyr Tyr Ser Gly Ser Thr Tyr Tyr Asn Pro Ser Leu Lys Ser Arg Val Thr Ile Ser Gly Asp Thr Pro Lys Asn Gln Phe Ser Leu Lys Leu Ser Ser Val Thr Ala Ala Asp Thr Ala Val Tyr Tyr Cys Ala Arg Thr Pro Ala Tyr Asp Gly Asp Ala Arg Ala Asp Phe Phe Asp Val Trp Gly Arg Gly Thr Leu Val Thr Val Ser Ser |
| 42 | Antibody 5 HCDR1 | Ser Gly Gly Tyr Tyr Trp Ser |
| 43 | Antibody 5 HCDR2 | Ser Ile Tyr Tyr Ser Gly Ser Thr Tyr Tyr Asn Pro Ser Leu Lys Ser |
| 44 | Antibody 5 HCDR3 | Thr Pro Ala Tyr Asp Gly Asp Ala Arg Ala Asp Phe Phe Asp Val |
| 45 | Antibody 5 VL | Asp Ile Val Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Arg Ala Pro Lys Val Leu Ile Tyr Lys Ala Ser Thr Leu Glu Ser Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Gln Gln Ser Leu Ile Pro Gln Trp Asp Phe Gly Gln Gly Thr Lys Leu Glu Ile Lys |
| 46 | Antibody 5 LCDR1 | Arg Ala Ser Gln Gly Ile Ser Ser Trp Leu Ala |

TABLE 3-continued

Table of Sequences

| SEQ ID NO | DESCRIPTION | SEQUENCE |
|---|---|---|
| 47 | Antibody 5 LCDR2 | Lys Ala Ser Thr Leu Glu Ser |
| 48 | Antibody 5 LCDR3 | Gln Gln Ser Leu Ile Pro Gln Trp Asp |
| 49 | Antibody 6 VH | Gln Val Gln Leu Gln Gln Ser Gly Pro Arg Leu Val Lys Pro Ser Gln Thr Leu Ser Leu Thr Cys Thr Val Ser Gly Gly Ser Ile Ser Ser Gly Gly Tyr Tyr Trp Ser Trp Ile Arg Gln Pro Ala Gly Lys Gly Leu Glu Trp Ile Gly Ser Ile Tyr Tyr Ser Gly Ser Thr Tyr Tyr Asn Pro Ser Leu Lys Ser Arg Val Thr Ile Ser Gly Asp Thr Pro Lys Asn Gln Phe Ser Leu Lys Leu Ser Ser Val Thr Ala Ala Asp Thr Ala Val Tyr Tyr Cys Ala Arg Thr Pro Ala Tyr Phe Gly Gln Asp Arg Thr Asp Phe Phe Asp Val Trp Gly Arg Gly Thr Leu Val Thr Val Ser Ser |
| 50 | Antibody 6 HCDR1 | Ser Gly Gly Tyr Tyr Trp Ser |
| 51 | Antibody 6 HCDR2 | Ser Ile Tyr Tyr Ser Gly Ser Thr Tyr Tyr Asn Pro Ser Leu Lys Ser |
| 52 | Antibody 6 HCDR3 | Thr Pro Ala Tyr Phe Gly Gln Asp Arg Thr Asp Phe Phe Asp Val |
| 53 | Antibody 6 VL | Asp Ile Val Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Arg Ala Pro Lys Val Leu Ile Tyr Lys Ala Ser Thr Leu Glu Ser Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Ala Asn Ile Ala Phe Pro Pro Trp Thr Phe Gly Gln Gly Thr Lys Leu Glu Ile Lys |
| 54 | Antibody 6 LCDR1 | Arg Ala Ser Gln Gly Ile Ser Ser Trp Leu Ala |
| 55 | Antibody 6 LCDR2 | Lys Ala Ser Thr Leu Glu Ser |
| 56 | Antibody 6 LCDR3 | Ala Asn Ile Ala Phe Pro Pro Trp Thr |
| 57 | Antibody 6_GL VH | Gln Val Gln Leu Gln Glu Ser Gly Pro Gly Leu Val Lys Pro Ser Glu Thr Leu Ser Leu Thr Cys Thr Val Ser Gly Gly Ser Ile Ser Ser Gly Gly Tyr Tyr Trp Ser Trp Ile Arg Gln Pro Pro Gly Lys Gly Leu Glu Trp Ile Gly Ser Ile Tyr Tyr Ser Gly Ser Thr Tyr Tyr Asn Pro Ser Leu Lys Ser Arg Val Thr Ile Ser Gly Asp Thr Ser Lys Asn Gln Phe Ser Leu Lys Leu Ser Ser Val Thr Ala Ala Asp Thr Ala Val Tyr Tyr Cys Ala Arg Thr Pro Ala Tyr Phe Gly Gln Asp Arg Thr Asp Phe Phe Asp Val Trp Gly Arg Gly Thr Leu Val Thr Val Ser Ser |
| 58 | Antibody 6_GL HCDR1 | Ser Gly Gly Tyr Tyr Trp Ser |
| 59 | Antibody 6_GL HCDR2 | Ser Ile Tyr Tyr Ser Gly Ser Thr Tyr Tyr Asn Pro Ser Leu Lys Ser |
| 60 | Antibody 6_GL HCDR3 | Thr Pro Ala Tyr Phe Gly Gln Asp Arg Thr Asp Phe Phe Asp Val |
| 61 | Antibody 6_GL VL | Asp Ile Gln Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Lys Ala Pro Lys Val Leu Ile Tyr Lys Ala Ser Thr Leu Glu Ser Gly Val Pro Ser Arg Phe Ser Gly Ser Gly Ser Gly Thr Glu Phe Thr Leu Thr Ile Ser Ser Leu Gln Pro Asp Asp Phe Ala Thr Tyr Tyr Cys Ala Asn Ile Ala Phe Pro Pro Trp Thr Phe Gly Gln Gly Thr Lys Leu Glu Ile Lys |

TABLE 3-continued

Table of Sequences

| SEQ ID NO | DESCRIPTION | SEQUENCE |
|---|---|---|
| 62 | Antibody 6_GL LCDR1 | Arg Ala Ser Gln Gly Ile Ser Ser Trp Leu Ala |
| 63 | Antibody 6_GL LCDR2 | Lys Ala Ser Thr Leu Glu Ser |
| 64 | Antibody 6_GL | Ala Asn Ile Ala Phe Pro Pro Trp Thr |
| 65 | Antibody 7 VH | Gln Val Gln Leu Gln Gln Ser Gly Pro Arg Leu Val Lys Pro Ser Gln Thr Leu Ser Leu Thr Cys Thr Val Ser Gly Gly Ser Ile Ser Ser Gly Gly Tyr Tyr Trp Ser Trp Ile Arg Gln Pro Ala Gly Lys Gly Leu Glu Trp Ile Gly Ser Ile Tyr Tyr Ser Gly Ser Thr Tyr Tyr Asn Pro Ser Leu Lys Ser Arg Val Thr Ile Ser Gly Asp Thr Pro Lys Asn Gln Phe Ser Leu Lys Leu Ser Ser Val Thr Ala Ala Asp Thr Ala Val Tyr Tyr Cys Ala Arg Thr Pro Ala Tyr Phe Gly Gln Asp Arg Thr Asp Phe Phe Asp Val Trp Gly Arg Gly Thr Leu Val Thr Val Ser Ser |
| 66 | Antibody 7 HCDR1 | Ser Gly Gly Tyr Tyr Trp Ser |
| 67 | Antibody 7 HCDR2 | Ser Ile Tyr Tyr Ser Gly Ser Thr Tyr Tyr Asn Pro Ser Leu Lys Ser |
| 68 | Antibody 7 HCDR3 | Thr Pro Ala Tyr Phe Gly Gln Asp Arg Thr Asp Phe Phe Asp Val |
| 69 | Antibody 7 VL | Asp Ile Val Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Arg Ala Pro Lys Val Leu Ile Tyr Lys Ala Ser Thr Leu Glu Ser Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Gln Gln Ser His His Pro Pro Trp Thr Phe Gly Gln Gly Thr Lys Leu Glu Ile Lys |
| 70 | Antibody 7 LCDR1 | Arg Ala Ser Gln Gly Ile Ser Ser Trp Leu Ala |
| 71 | Antibody 7 LCDR2 | Lys Ala Ser Thr Leu Glu Ser |
| 72 | Antibody 7 LCDR3 | Gln Gln Ser His His Pro Pro Trp Thr |
| 73 | Antibody 7_GL VH | Gln Val Gln Leu Gln Glu Ser Gly Pro Gly Leu Val Lys Pro Ser Glu Thr Leu Ser Leu Thr Cys Thr Val Ser Gly Gly Ser Ile Ser Ser Gly Gly Tyr Tyr Trp Ser Trp Ile Arg Gln Pro Pro Gly Lys Gly Leu Glu Trp Ile Gly Ser Ile Tyr Tyr Ser Gly Ser Thr Tyr Tyr Asn Pro Ser Leu Lys Ser Arg Val Thr Ile Ser Gly Asp Thr Ser Lys Asn Gln Phe Ser Leu Lys Leu Ser Ser Val Thr Ala Ala Asp Thr Ala Val Tyr Tyr Cys Ala Arg Thr Pro Ala Tyr Phe Gly Gln Asp Arg Thr Asp Phe Phe Asp Val Trp Gly Arg Gly Thr Leu Val Thr Val Ser Ser |
| 74 | Antibody 7_GL HCDR1 | Ser Gly Gly Tyr Tyr Trp Ser |
| 75 | Antibody 7_GL HCDR2 | Ser Ile Tyr Tyr Ser Gly Ser Thr Tyr Tyr Asn Pro Ser Leu Lys Ser |
| 76 | Antibody 7_GL HCDR3 | Thr Pro Ala Tyr Phe Gly Gln Asp Arg Thr Asp Phe Phe Asp Val |
| 77 | Antibody 7_GL VL | Asp Ile Gln Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Lys Ala Pro Lys Val Leu Ile Tyr Lys Ala Ser Thr Leu Glu Ser Gly Val Pro Ser Arg Phe Ser Gly Ser Gly Ser Gly Thr Glu Phe Thr Leu Thr Ile Ser Ser Leu Gln Pro Asp Asp Phe Ala Thr Tyr Tyr Cys |

TABLE 3-continued

Table of Sequences

| SEQ ID NO | DESCRIPTION | SEQUENCE |
|---|---|---|
| | | Gln Gln Ser His His Pro Pro Trp Thr Phe Gly Gln Gly Thr Lys Leu Glu Ile Lys |
| 78 | Antibody 7_GL LCDR1 | Arg Ala Ser Gln Gly Ile Ser Ser Trp Leu Ala |
| 79 | Antibody 7_GL LCDR2 | Lys Ala Ser Thr Leu Glu Ser |
| 80 | Antibody 7_GL LCDR3 | Gln Gln Ser His His Pro Pro Trp Thr |
| 81 | Antibody 8_GL VH | Gln Val Gln Leu Gln Glu Ser Gly Pro Gly Leu Val Lys Pro Ser Glu Thr Leu Ser Leu Thr Cys Thr Val Ser Gly Gly Ser Ile Ser Ala Gly Gly Tyr Tyr Trp Ser Trp Ile Arg Gln Pro Pro Gly Lys Gly Leu Glu Trp Ile Gly Ser Leu Tyr Tyr Ser Gly Ser Thr Tyr Tyr Asn Pro Ser Leu Lys Gly Arg Val Thr Ile Ser Gly Asp Thr Ser Lys Asn Gln Phe Ser Leu Lys Leu Ser Ser Val Thr Ala Ala Asp Thr Ala Val Tyr Tyr Cys Ala Arg Thr Pro Ala Tyr Phe Gly Gln Asp Arg Thr Asp Phe Phe Asp Val Trp Gly Arg Gly Thr Leu Val Thr Val Ser Ser |
| 82 | Antibody 8_GL HCDR1 | Ala Gly Gly Tyr Tyr Trp Ser |
| 83 | Antibody 8_GL HCDR2 | Ser Leu Tyr Tyr Ser Gly Ser Thr Tyr Tyr Asn Pro Ser Leu Lys Gly |
| 84 | Antibody 8_GL HCDR3 | Thr Pro Ala Tyr Phe Gly Gln Asp Arg Thr Asp Phe Phe Asp Val |
| 85 | Antibody 8_GL VL | Asp Ile Gln Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Lys Ala Pro Lys Val Leu Ile Tyr Lys Ala Ser Thr Leu Glu Ser Gly Val Pro Ser Arg Phe Ser Gly Ser Gly Ser Gly Thr Glu Phe Thr Leu Thr Ile Ser Ser Leu Gln Pro Asp Asp Phe Ala Thr Tyr Tyr Cys Gln Gln Ser His His Pro Pro Trp Thr Phe Gly Gln Gly Thr Lys Leu Glu Ile Lys |
| 86 | Antibody 8_GL LCDR1 | Arg Ala Ser Gln Gly Ile Ser Ser Trp Leu Ala |
| 87 | Antibody 8_GL LCDR2 | Lys Ala Ser Thr Leu Glu Ser |
| 88 | Antibody 8_GL LCDR3 | Gln Gln Ser His His Pro Pro Trp Thr |
| 89 | Antibody 9 VH | Gln Val Gln Leu Gln Gln Ser Gly Pro Arg Leu Val Glu Pro Ser Gln Thr Leu Ser Leu Thr Cys Thr Val Ser Gly Gly Ser Ile Ser Ser Asp Gly Tyr Tyr Trp Ser Trp Ile Arg Gln Pro Ala Gly Lys Gly Leu Glu Trp Ile Gly Ser Ile Tyr Tyr Ser Gly Ser Thr Tyr Tyr Asn Pro Ser Leu Lys Ser Arg Val Thr Ile Ser Gly Asp Thr Pro Lys Asn Gln Phe Ser Leu Lys Leu Ser Ser Val Thr Ala Ala Asp Thr Ala Val Tyr Tyr Cys Ala Arg Thr Pro Ala Tyr Phe Gly Gln Asp Arg Thr Asp Phe Phe Asp Val Trp Gly Arg Gly Thr Leu Val Thr Val Ser Ser |
| 90 | Antibody 9 HCDR1 | Ser Asp Gly Tyr Tyr Trp Ser |
| 91 | Antibody 9 HCDR2 | Ser Ile Tyr Tyr Ser Gly Ser Thr Tyr Tyr Asn Pro Ser Leu Lys Ser |
| 92 | Antibody 9 HCDR3 | Thr Pro Ala Tyr Phe Gly Gln Asp Arg Thr Asp Phe Phe Asp Val |
| 93 | Antibody 9 VL | Asp Ile Val Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Arg Ala Pro Lys Val Leu Ile Tyr Lys Ala Ser Thr Leu Glu Ser Gly Val Pro Ser Arg Phe Ser Gly Ser Gly |

TABLE 3-continued

| Table of Sequences | | |
|---|---|---|
| SEQ ID NO | DESCRIPTION | SEQUENCE |
| | | Ser Gly Thr Asp Phe Thr Leu Thr Ile Ser Ser Leu Gln Pro Glu Asp Phe Ala Thr Tyr Tyr Cys Gln Gln Ser His His Pro Pro Trp Thr Phe Gly Gln Gly Thr Lys Leu Glu Ile Lys |
| 94 | Antibody 9 LCDR1 | Arg Ala Ser Gln Gly Ile Ser Ser Trp Leu Ala |
| 95 | Antibody 9 LCDR2 | Lys Ala Ser Thr Leu Glu Ser |
| 96 | Antibody 9 LCDR3 | Gln Gln Ser His His Pro Pro Trp Thr |
| 97 | Antibody 10 VH | Gln Val Gln Leu Gln Gln Ser Gly Pro Arg Leu Val Glu Pro Ser Gln Thr Leu Ser Leu Thr Cys Thr Val Ser Gly Gly Ser Ile Ser Ser Asp Gly Tyr Tyr Trp Ser Trp Ile Arg Gln Pro Ala Gly Lys Gly Leu Glu Trp Ile Gly Ser Ile Tyr Tyr Ser Gly Ser Thr Tyr Tyr Asn Pro Ser Leu Arg Ser Arg Val Thr Ile Ser Gly Asp Thr Pro Lys Asn Gln Phe Ser Leu Lys Leu Ser Ser Val Thr Ala Ala Asp Thr Ala Val Tyr Tyr Cys Ala Arg Thr Pro Ala Tyr Phe Gly Gln Asp Arg Thr Asp Phe Phe Asp Val Trp Gly Arg Gly Thr Leu Val Thr Val Ser Ser |
| 98 | Antibody 10 HCDR1 | Ser Asp Gly Tyr Tyr Trp Ser |
| 99 | Antibody 10 HCDR2 | Ser Ile Tyr Tyr Ser Gly Ser Thr Tyr Tyr Asn Pro Ser Leu Arg Ser |
| 100 | Antibody 10 HCDR3 | Thr Pro Ala Tyr Phe Gly Gln Asp Arg Thr Asp Phe Phe Asp Val |
| 101 | Antibody 10 VL | Asp Ile Val Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Gly Ala Pro Lys Val Leu Ile Tyr Lys Ala Ser Thr Leu Glu Ser Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Gln Gln Ser His His Pro Pro Trp Thr Phe Ser Gln Gly Thr Lys Leu Glu Ile Lys |
| 102 | Antibody 10 LCDR1 | Arg Ala Ser Gln Gly Ile Ser Ser Trp Leu Ala |
| 103 | Antibody 10 LCDR2 | Lys Ala Ser Thr Leu Glu Ser |
| 104 | Antibody 10 LCDR3 | Gln Gln Ser His His Pro Pro Trp Thr |
| 105 | Antibody 11 VH | Gln Val Gln Leu Gln Gln Ser Gly Pro Arg Leu Val Glu Pro Ser Gln Thr Leu Ser Leu Thr Cys Thr Val Ser Gly Gly Ser Ile Ser Ala Asp Gly Tyr Tyr Trp Ser Trp Ile Arg Gln Pro Ala Gly Lys Gly Leu Glu Trp Ile Gly Ser Leu Tyr Tyr Ser Gly Ser Thr Tyr Tyr Asn Pro Ser Leu Arg Gly Arg Val Thr Ile Ser Gly Asp Thr Pro Lys Asn Gln Phe Ser Leu Lys Leu Ser Ser Val Thr Ala Ala Asp Thr Ala Val Tyr Tyr Cys Ala Arg Thr Pro Ala Tyr Phe Gly Gln Asp Arg Thr Asp Phe Phe Asp Val Trp Gly Arg Gly Thr Leu Val Thr Val Ser Ser |
| 106 | Antibody 11 HCDR1 | Ala Asp Gly Tyr Tyr Trp Ser |
| 107 | Antibody 11 HCDR2 | Ser Leu Tyr Tyr Ser Gly Ser Thr Tyr Tyr Asn Pro Ser Leu Arg Gly |
| 108 | Antibody 11 HCDR3 | Thr Pro Ala Tyr Phe Gly Gln Asp Arg Thr Asp Phe Phe Asp Val |
| 109 | Antibody 11 VL | Asp Ile Val Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Gly Ala Pro |

TABLE 3-continued

Table of Sequences

| SEQ ID NO | DESCRIPTION | SEQUENCE |
|---|---|---|
| | | Lys Val Leu Ile Tyr Lys Ala Ser Thr Leu Glu Ser Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Gln Gln Ser His His Pro Pro Trp Thr Phe Ser Gln Gly Thr Lys Leu Glu Ile Lys |
| 110 | Antibody 11 LCDR1 | Arg Ala Ser Gln Gly Ile Ser Ser Trp Leu Ala |
| ill | Antibody 11 LCDR2 | Lys Ala Ser Thr Leu Glu Ser |
| 112 | Antibody 11 LCDR3 | Gln Gln Ser His His Pro Pro Trp Thr |
| 113 | Antibody 11_GL VH | Gln Val Gln Leu Gln Glu Ser Gly Pro Gly Leu Val Lys Pro Ser Glu Thr Leu Ser Leu Thr Cys Thr Val Ser Gly Gly Ser Ile Ser Ala Asp Gly Tyr Tyr Trp Ser Trp Ile Arg Gln Pro Pro Gly Lys Gly Leu Glu Trp Ile Gly Ser Leu Tyr Tyr Ser Gly Ser Thr Tyr Tyr Asn Pro Ser Leu Arg Gly Arg Val Thr Ile Ser Gly Asp Thr Ser Lys Asn Gln Phe Ser Leu Lys Leu Ser Ser Val Thr Ala Ala Asp Thr Ala Val Tyr Tyr Cys Ala Arg Thr Pro Ala Tyr Phe Gly Gln Asp Arg Thr Asp Phe Phe Asp Val Trp Gly Arg Gly Thr Leu Val Thr Val Ser Ser |
| 114 | Antibody 11_GL HCDRI | Ala Asp Gly Tyr Tyr Trp Ser |
| 115 | Antibody 11_GL HCDR2 | Ser Leu Tyr Tyr Ser Gly Ser Thr Tyr Tyr Asn Pro Ser Leu Arg Gly |
| 116 | Antibody 11_GL HCDR3 | Thr Pro Ala Tyr Phe Gly Gln Asp Arg Thr Asp Phe Phe Asp Val |
| 117 | Antibody 11_GL VL | Asp Ile Gln Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Lys Ala Pro Lys Val Leu Ile Tyr Lys Ala Ser Thr Leu Glu Ser Gly Val Pro Ser Arg Phe Ser Gly Ser Gly Ser Gly Thr Glu Phe Thr Leu Thr Ile Ser Ser Leu Gln Pro Asp Asp Phe Ala Thr Tyr Tyr Cys Gln Gln Ser His His Pro Pro Trp Thr Phe Gly Gln Gly Thr Lys Leu Glu Ile Lys |
| 118 | Antibody 11_GL LCDR1 | Arg Ala Ser Gln Gly Ile Ser Ser Trp Leu Ala |
| 119 | Antibody 11_GL LCDR2 | Lys Ala Ser Thr Leu Glu Ser |
| 120 | Antibody 11_GL LCDR3 | Gln Gln Ser His His Pro Pro Trp Thr |
| 121 | Antibody 12_GL VH | Gln Val Gln Leu Gln Glu Ser Gly Pro Gly Leu Val Lys Pro Ser Glu Thr Leu Ser Leu Thr Cys Thr Val Ser Gly Gly Ser Ile Ser Ala Asp Gly Tyr Tyr Trp Ser Trp Ile Arg Gln Pro Pro Gly Lys Gly Leu Glu Trp Ile Gly Ser Leu Tyr Tyr Ser Gly Ser Thr Tyr Tyr Asn Pro Ser Leu Lys Gly Arg Val Thr Ile Ser Gly Asp Thr Ser Lys Asn Gln Phe Ser Leu Lys Leu Ser Ser Val Thr Ala Ala Asp Thr Ala Val Tyr Tyr Cys Ala Arg Thr Pro Ala Tyr Phe Gly Gln Asp Arg Thr Asp Phe Phe Asp Val Trp Gly Arg Gly Thr Leu Val Thr Val Ser Ser |
| 122 | Antibody 12_GL HCDR1 | Ala Asp Gly Tyr Tyr Trp Ser |
| 123 | Antibody 12_GL HCDR2 | Ser Leu Tyr Tyr Ser Gly Ser Thr Tyr Tyr Asn Pro Ser Leu Lys Gly |

TABLE 3-continued

| SEQ ID NO | DESCRIPTION | SEQUENCE |
|---|---|---|
| | | Table of Sequences |
| 124 | Antibody 12_GL HCDR3 | Thr Pro Ala Tyr Phe Gly Gln Asp Arg Thr Asp Phe Phe Asp Val |
| 125 | Antibody 12_GL VL | Asp Ile Gln Met Thr Gln Ser Pro Ser Thr Leu Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Lys Ala Pro Lys Val Leu Ile Tyr Lys Ala Ser Thr Leu Glu Ser Gly Val Pro Ser Arg Phe Ser Gly Ser Gly Ser Gly Thr Glu Phe Thr Leu Thr Ile Ser Ser Leu Gln Pro Asp Asp Phe Ala Thr Tyr Tyr Cys Gln Gln Ser His His Pro Pro Trp Thr Phe Gly Gln Gly Thr Lys Leu Glu Ile Lys |
| 126 | Antibody 12_GL LCDR1 | Arg Ala Ser Gln Gly Ile Ser Ser Trp Leu Ala |
| 127 | Antibody 12_GL LCDR2 | Lys Ala Ser Thr Leu Glu Ser |
| 128 | Antibody 12_GL LCDR3 | Gln Gln Ser His His Pro Pro Trp Thr |
| 129 | HCDR1 | Gly Tyr Tyr Phe His |
| 130 | HCDR2 | Arg Ile Asp Pro Glu Asp Asp Ser Thr Lys Tyr Ala Glu Arg Phe Lys Asp |
| 131 | HCDR3 | Trp Arg Ile Tyr Arg Asp Ser Ser Gly Arg Pro Phe Tyr Val Met Asp Ala |
| 132 | LCDR1 | Leu Ala Ser Glu Asp Ile Tyr Thr Tyr Leu Thr |
| 133 | LCDR2 | Gly Ala Asn Lys Leu Gln Asp |
| 134 | LCDR3 | Leu Gln Gly Ser Lys Phe Pro Leu Thr |
| 135 | Human IL-18 | Met Ala Ala Glu Pro Val Glu Asp Asn Cys Ile Asn Phe Val Ala Met Lys Phe Ile Asp Asn Thr Leu Tyr Phe Ile Ala Glu Asp Asp Glu Asn Leu Glu Ser Asp Tyr Phe Gly Lys Leu Glu Ser Lys Leu Ser Val Ile Arg Asn Leu Asn Asp Gln Val Leu Phe Ile Asp Gln Gly Asn Arg Pro Leu Phe Glu Asp Met Thr Asp Ser Asp Cys Arg Asp Asn Ala Pro Arg Thr Ile Phe Ile Ile Ser Met Tyr Lys Asp Ser Gln Pro Arg Gly Met Ala Val Thr Ile Ser Val Lys Cys Glu Lys Ile Ser Thr Leu Ser Cys Glu Asn Lys Ile Ile Ser Phe Lys Glu Met Asn Pro Pro Asp Asn Ile Lys Asp Thr Lys Ser Asp Ile Ile Phe Phe Gln Arg Ser Val Pro Gly His Asp Asn Lys Met Gln Phe Glu Ser Ser Ser Tyr Glu Gly Tyr Phe Leu Ala Cys Glu Lys Glu Arg Asp Leu Phe Lys Leu Ile Leu Lys Lys Glu Asp Glu Leu Gly Asp Arg Ser Ile Met Phe Thr Val Gln Asn Glu Asp |
| 136 | Human I1-18 (PN) | atggctgctg aaccagtaga agacaattgc atcaactttg tggcaatgaa atttattgac 60 aatacgcttt actttatagc tgaagatgat gaaaacctgg aatcagatta ctttggcaag 120 cttgaatcta aattatcagt cataagaaat ttgaatgacc aagttctctt cattgaccaa 180 ggaaatcggc ctctatttga agatatgact gattctgact gtagagataa tgcaccccgg 240 accatattta ttataagtat gtataaagat agccagccta gaggtatggc tgtaactatc 300 tctgtgaagt gtgagaaaat ttcaactctc tcctgtgaga acaaaattat ttcctttaag 360 gaaatgaatc ctcctgataa catcaaggat acaaaaagtg acatcatatt ctttcagaga 420 agtgtcccag gacatgataa taagatgcaa tttgaatctt catcatacga aggatacttt 480 |

TABLE 3-continued

| SEQ ID NO | DESCRIPTION | SEQUENCE |
|---|---|---|
| | | Table of Sequences |
| | | ctagcttgtg aaaaagagag agaccttttt aaactcattt tgaaaaaaga ggatgaattg 540 ggggatagat ctataatgtt cactgttcaa aacgaagact ag 582 |
| 137 | H1 heavy chain | Gln Val Gln Leu Val Gln Ser Gly Ala Glu Val Lys Lys Pro Gly Ala Ser Val Lys Val Ser Cys Lys Val Ser Gly Glu Ile Ser Thr Gly Tyr Tyr Phe His Trp Val Arg Gln Ala Pro Gly Lys Gly Leu Glu Trp Met Gly Arg Ile Asp Pro Glu Asp Asp Ser Thr Lys Tyr Ala Glu Arg Phe Lys Asp Arg Val Thr Met Thr Glu Asp Thr Ser Thr Asp Thr Ala Tyr Met Glu Leu Ser Ser Leu Arg Ser Glu Asp Thr Ala Val Tyr Tyr Cys Thr Thr Trp Arg Ile Tyr Arg Asp Ser Ser Gly Arg Pro Phe Tyr Val Met Asp Ala Trp Gly Gln Gly Thr Leu Val Thr Val Ser Ser Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys |
| 138 | H1 heavy chain (PN) | aggtgcagc tggtgcagag cggagccgag gtgaagaagc ctggcgccag cgtcaaggtg 60 tcctgtaagg tgtccggcga gatcagcacc ggctactact tccactgggt gaggcaggcc 120 cctggcaagg gcctggagtg gatgggcaga atcgaccccg aggacgacag caccaagtac 180 gccgagcggt tcaaggacag ggtgaccatg accgaggaca ccagcaccga taccgcctac 240 atggagctgt ccagcctgag aagcgaggat accgccgtgt actactgtac cacctggcgg 300 atctacagag acagcagcgg cagacccttc tacgtgatgg atgcctgggg ccagggcaca 360 ctagtgaccg tgtccagcgc cagcaccaag ggccccagcg tgttccccct ggcccccagc 420 agcaagagca ccagcggcgg cacagccgcc ctgggctgcc tggtgaagga ctacttcccc 480 gaaccggtga ccgtgtcctg gaacagcgga gccctgacca gcggcgtgca caccttcccc 540 gccgtgctgc agagcagcgg cctgtacagc ctgagcagcg tggtgaccgt gcccagcagc 600 agcctgggca cccagaccta catctgtaac gtgaaccaca agcccagcaa caccaaggtg 660 gacaagaagg tggagcccaa gagctgtgac aagacccaca cctgcccccc ctgccctgcc 720 |

TABLE 3-continued

| Table of Sequences | | |
|---|---|---|
| SEQ ID NO | DESCRIPTION | SEQUENCE |
| | | cccgagctgc tgggaggccc cagcgtgttc ctgttccccc ccaagcctaa ggacaccctg 780 atgatcagca gaacccccga ggtgacctgt gtggtggtgg atgtgagcca cgaggaccct 840 gaggtgaagt tcaactggta cgtggacggc gtggaggtgc acaatgccaa gaccaagccc 900 agggaggagc agtacaacag cacctaccgg gtggtgtccg tgctgaccgt gctgcaccag 960 gattggctga acggcaagga gtacaagtgt aaggtgtcca acaaggccct gcctgcccct 1020 atcgagaaaa ccatcagcaa ggccaagggc cagcccagag agccccaggt gtacaccctg 1080 ccccctagca gagatgagct gaccaagaac caggtgtccc tgacctgcct ggtgaagggc 1140 ttctacccca gcgacatcgc cgtggagtgg gagagcaacg gccagcccga gaacaactac 1200 aagaccaccc cccctgtgct ggacagcgat ggcagcttct tcctgtacag caagctgacc 1260 gtggacaaga gcagatggca gcagggcaac gtgttcagct gctccgtgat gcacgaggcc 1320 ctgcacaatc actacaccca gaagagcctg agcctgtccc ctggcaagtg a 1371 |
| 139 | H1 variable region | Gln Val Gln Leu Val Gln Ser Gly Ala Glu Val Lys Lys Pro Gly Ala Ser Val Lys Val Ser Cys Lys Val Ser Gly Glu Ile Ser Thr Gly Tyr Tyr Phe His Trp Val Arg Gln Ala Pro Gly Lys Gly Leu Glu Trp Met Gly Arg Ile Asp Pro Glu Asp Asp Ser Thr Lys Tyr Ala Glu Arg Phe Lys Asp Arg Val Thr Met Thr Glu Asp Thr Ser Thr Asp Thr Ala Tyr Met Glu Leu Ser Ser Leu Arg Ser Glu Asp Thr Ala Val Tyr Tyr Cys Thr Thr Trp Arg Ile Tyr Arg Asp Ser Ser Gly Arg Pro Phe Tyr Val Met Asp Ala Trp Gly Gln Gly Thr Leu Val Thr Val Ser Ser |
| 140 | H1 variable region (PN) | caggtgcagc tggtgcagag cggagccgag gtgaagaagc ctggcgccag cgtcaaggtg 60 tcctgtaagg tgtccggcga gatcagcacc ggctactact tccactgggt gaggcaggcc 120 cctggcaagg gcctggagtg gatgggcaga atcgaccccg aggacgacag caccaagtac 180 gccgagcggt tcaaggacag ggtgaccatg accgaggaca ccagcaccga taccgcctac 240 atggagctgt ccagcctgag aagcgaggat accgccgtgt actactgtac cacctggcgg 300 atctacagag acagcagcgg cagacccttc tacgtgatgg atgcctgggg ccagggcaca 360 ctagtgaccg tgtccagc 378 |
| 141 | L2 light chain | Asp Ile Gln Met Thr Gln Ser Pro Ser Ser Val Ser Ala Ser Val Gly Asp Arg Val Thr Ile Thr Cys Leu Ala Ser Glu Asp Ile Tyr Thr Tyr Leu Thr Trp Tyr Gln Gln Lys Pro Gly Lys Ala Pro Lys Leu Leu Ile Tyr Gly Ala Asn Lys Leu Gln Asp Gly Val Pro Ser Arg Phe Ser Gly Ser Gly Ser Gly Thr Asp Tyr Thr Leu Thr Ile Ser Ser Leu Gln Pro Glu Asp Phe Ala Thr Tyr Tyr Cys Leu Gln Gly Ser Lys Phe Pro Leu Thr Phe Gly Gln Gly Thr Lys Leu Glu Ile Lys Arg Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu Lys His Lys Val Tyr Ala Cys Glu Val Thr His Gln Gly Leu Ser Ser Pro Val Thr Lys Ser Phe Asn Arg Gly Glu Cys |

TABLE 3-continued

Table of Sequences

| SEQ ID NO | DESCRIPTION | SEQUENCE |
|---|---|---|
| 142 | L2 light chain (PN) | gatatccaga tgacccagtc ccccagcagc gtgtccgcct ctgtgggcga tagagtgacc 60<br>atcacctgcc tggccagcga ggacatctac acctacctga cctggtatca gcagaagcct 120<br>ggcaaggccc ctaagctgct gatctacggc gccaacaagc tgcaggacgg cgtgcccagc 180<br>agattcagcg gcagcggctc cggcaccgac tacaccctga ccatcagcag cctgcagcct 240<br>gaggatttcg ccacctacta ctgcctgcag ggcagcaagt tcccccctgac cttcggccag 300<br>ggcaccaagc tggagatcaa gcgtacggtg gccgccccca gcgtgttcat cttccccccc 360<br>agcgatgagc agctgaagag cggcaccgcc agcgtggtgt gtctgctgaa caacttctac 420<br>ccccgggagg ccaaggtgca gtggaaggtg gacaatgccc tgcagagcgg caacagccag 480<br>gagagcgtga ccgagcagga cagcaaggac tccacctaca gcctgagcag caccctgacc 540<br>ctgagcaagg ccgactacga gaagcacaag gtgtacgcct gtgaggtgac ccaccagggc 600<br>ctgtccagcc ccgtgaccaa gagcttcaac cggggcgagt gc 642 |
| 143 | L2 variable region | Asp Ile Gln Met Thr Gln Ser Pro Ser Ser Val Ser Ala Ser Val Gly Asp Arg Val Thr Ile Thr Cys Leu Ala Ser Glu Asp Ile Tyr Thr Tyr Leu Thr Trp Tyr Gln Gln Lys Pro Gly Lys Ala Pro Lys Leu Leu Ile Tyr Gly Ala Asn Lys Leu Gln Asp Gly Val Pro Ser Arg Phe Ser Gly Ser Gly Ser Gly Thr Asp Tyr Thr Leu Thr Ile Ser Ser Leu Gln Pro Glu Asp Phe Ala Thr Tyr Tyr Cys Leu Gln Gly Ser Lys Phe Pro Leu Thr Phe Gly Gln Gly Thr Lys Leu Glu Ile Lys |
| 144 | L2 var (PN) | gatatccaga tgacccagtc ccccagcagc gtgtccgcct ctgtgggcga tagagtgacc 60<br>atcacctgcc tggccagcga ggacatctac acctacctga cctggtatca gcagaagcct 120<br>ggcaaggccc ctaagctgct gatctacggc gccaacaagc tgcaggacgg cgtgcccagc 180<br>agattcagcg gcagcggctc cggcaccgac tacaccctga ccatcagcag cctgcagcct 240<br>gaggatttcg ccacctacta ctgcctgcag ggcagcaagt tcccccctgac cttcggccag 300<br>ggcaccaagc tggagatcaa g 321 |
| 145 | H2 heavy chain | Gln Val Gln Leu Val Gln Ser Gly Ala Glu Val Lys Lys Pro Gly Ala Ser Val Lys Val Ser Cys Lys Val Ser Gly Glu Ile Ser Thr Gly Tyr Tyr Phe His Trp Val Arg Arg Arg Pro Gly Lys Gly Leu Glu Trp Met Gly Arg Ile Asp Pro Glu Asp Asp Ser Thr Lys Tyr Ala Glu Arg Phe Lys Asp Arg Val Thr Met Thr Glu Asp Thr Ser Thr Asp Thr Ala Tyr Met Glu Leu Ser Ser Leu Arg Ser Glu Asp Thr Ala Val Tyr Tyr Cys Thr Thr Trp Arg Ile Tyr Arg Asp Ser Ser Gly Arg Pro Phe Tyr Val Met Asp Ala Trp Gly Gln Gly Thr Leu Val Thr Val Ser Ser Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp |

TABLE 3-continued

Table of Sequences

| SEQ ID NO | DESCRIPTION | SEQUENCE |
|---|---|---|
| | | Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys |
| 146 | H2 heavy chain (PN) | caggtccagc tggtacagtc tggggctgag gtgaagaagc ctggggcctc agtgaaggtc 60 tcctgcaagg tttccggaga aataagtact ggatactatt tccactgggt gcgacgaagg 120 cctggaaaag ggcttgagtg gatgggaagg attgatcctg aggatgatag tactaaatat 180 gctgagaggt tcaaagacag agtcaccatg accgaggaca catctacaga cacagcctac 240 atggagctga gcagcctgag atctgaggac acggccgtgt attactgtac cacatggcgg 300 atataccgag atagttctgg ccgccccttc tatgttatgg atgcctgggg ccaagggaca 360 ctagtcacag tctcctcagc ctccaccaag ggcccatcgg tcttccccct ggcaccctcc 420 tccaagagca cctctggggg cacagcggcc ctgggctgcc tggtcaagga ctacttcccc 480 gaaccggtga cggtgtcgtg gaactcaggc gccctgacca gcggcgtgca caccttcccg 540 gctgtcctac agtcctcagg actctactcc ctcagcagcg tggtgaccgt gccctccagc 600 agcttgggca cccagaccta catctgcaac gtgaatcaca agcccagcaa caccaaggtg 660 gacaagaaag ttgagcccaa atcttgtgac aaaactcaca catgcccacc gtgcccagca 720 cctgaactcc tggggggacc gtcagtcttc ctcttccccc caaaacccaa ggacaccctc 780 atgatctccc ggacccctga ggtcacatgc gtggtggtgg acgtgagcca cgaagaccct 840 gaggtcaagt tcaactggta cgtggacggc gtggaggtgc ataatgccaa gacaaagccg 900 cgggaggagc agtacaacag cacgtaccgt gtggtcagcg tcctcaccgt cctgcaccag 960 gactggctga atggcaagga gtacaagtgc aaggtctcca acaaagccct cccagccccc 1020 atcgagaaaa ccatctccaa agccaaaggg cagccccgag aaccacaggt gtacaccctg 1080 cccccatccc gggatgagct gaccaagaac caggtcagcc tgacctgcct ggtcaaaggc 1140 ttctatccca gcgacatcgc cgtggagtgg gagagcaatg ggcagccgga gaacaactac 1200 aagaccacgc ctcccgtgct ggactccgac ggctccttct tcctctacag caagctcacc 1260 gtggacaaga gcaggtggca gcaggggaac gtcttctcat gctccgtgat gcatgaggct 1320 ctgcacaacc actacacgca gaagagcctc tccctgtctc cgggtaaa 1368 |
| 147 | H2 variable region | Gln Val Gln Leu Val Gln Ser Gly Ala Glu Val Lys Lys Pro Gly Ala Ser Val Lys Val Ser Cys Lys Val Ser Gly Glu Ile Ser Thr Gly Tyr Tyr Phe His Trp Val Arg Arg Arg Pro Gly Lys Gly Leu Glu Trp Met Gly Arg Ile Asp Pro Glu Asp Asp Ser Thr Lys Tyr Ala Glu Arg Phe Lys Asp Arg Val Thr Met Thr Glu Asp Thr Ser Thr Asp Thr Ala Tyr Met Glu Leu Ser Ser Leu Arg Ser Glu Asp Thr Ala Val Tyr Tyr Cys Thr Thr Trp Arg Ile Tyr Arg Asp Ser Ser Gly Arg Pro Phe |

TABLE 3-continued

| Table of Sequences | | |
|---|---|---|
| SEQ ID NO | DESCRIPTION | SEQUENCE |
| | | Tyr Val Met Asp Ala Trp Gly Gln Gly Thr Leu Val Thr Val Ser Ser |
| 148 | H2 variable region (PN) | caggtccagc tggtacagtc tggggctgag gtgaagaagc ctggggcctc agtgaaggtc 60 tcctgcaagg tttccggaga aataagtact ggatactatt tccactgggt gcgacgaagg 120 cctggaaaag ggcttgagtg gatgggaagg attgatcctg aggatgatag tactaaatat 180 gctgagaggt tcaaagacag agtcaccatg accgaggaca catctacaga cacagcctac 240 atggagctga gcagcctgag atctgaggac acggccgtgt attactgtac cacatggcgg 300 atataccgag atagttctgg ccgccccttc tatgttatgg atgcctgggg ccaagggaca 360 ctagtcacag tctcctca 378 |
| 149 | H3 heavy chain | Gln Val Gln Leu Val Gln Ser Gly Ala Glu Val Lys Lys Pro Gly Ala Ser Val Lys Val Ser Cys Lys Val Ser Gly Glu Ile Ser Thr Gly Tyr Tyr Phe His Phe Val Arg Arg Arg Pro Gly Lys Gly Leu Glu Trp Met Gly Arg Ile Asp Pro Glu Asp Asp Ser Thr Lys Tyr Ala Glu Arg Phe Lys Asp Arg Val Thr Met Thr Ala Asp Thr Ser Thr Asp Thr Ala Tyr Met Glu Leu Ser Ser Leu Arg Ser Glu Asp Thr Ala Thr Tyr Phe Cys Thr Thr Trp Arg Ile Tyr Arg Asp Ser Ser Gly Arg Pro Phe Tyr Val Met Asp Ala Trp Gly Gln Gly Thr Leu Val Thr Val Ser Ser Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys |
| 150 | H3 heavy chain (PN) | caggtccagc tggtacagtc tggggctgag gtgaagaagc ctggggcctc agtgaaggtc 60 tcctgcaagg tttccggaga aataagtact ggatactatt tccactttgt gcgacgaagg 120 cctggaaaag ggcttgagtg gatgggaagg attgatcctg aggatgatag tactaaatat 180 gctgagaggt tcaaagacag agtcaccatg accgcagaca catctacaga cacagcctac 240 atggagctga gcagcctgag atctgaggac acggccactt atttttgtac cacatggcgg 300 atataccgag atagttctgg ccgccccttc tatgttatgg atgcctgggg ccaagggaca 360 |

TABLE 3-continued

Table of Sequences

| SEQ ID NO | DESCRIPTION | SEQUENCE |
|---|---|---|
| | | ctagtcacag tctcctcagc ctccaccaag ggcccatcgg tcttcccccct ggcaccctcc 420 tccaagagca cctctggggg cacagcggcc ctgggctgcc tggtcaagga ctacttcccc 480 gaaccggtga cggtgtcgtg gaactcaggc gccctgacca gcggcgtgca caccttcccg 540 gctgtcctac agtcctcagg actctactcc ctcagcagcg tggtgaccgt gccctccagc 600 agcttgggca cccagaccta catctgcaac gtgaatcaca agcccagcaa caccaaggtg 660 gacaagaaag ttgagcccaa atcttgtgac aaaactcaca catgcccacc gtgcccagca 720 cctgaactcc tgggggggacc gtcagtcttc ctcttccccc caaaacccaa ggacaccctc 780 atgatctccc ggacccctga ggtcacatgc gtggtggtgg acgtgagcca cgaagaccct 840 gaggtcaagt tcaactggta cgtggacggc gtggaggtgc ataatgccaa gacaaagccg 900 egggaggagc agtacaacag cacgtaccgt gtggtcagcg tcctcaccgt cctgcaccag 960 gactggctga atggcaagga gtacaagtgc aaggtctcca acaaagccct cccagccccc 1020 atcgagaaaa ccatctccaa agccaaaggg cagccccgag aaccacaggt gtacaccctg 1080 cccccatccc gggatgagct gaccaagaac caggtcagcc tgacctgcct ggtcaaaggc 1140 ttctatccca gcgacatcgc cgtggagtgg gagagcaatg ggcagccgga gaacaactac 1200 aagaccacgc ctcccgtgct ggactccgac ggctccttct tcctctacag caagctcacc 1260 gtggacaaga gcaggtggca gcaggggaac gtcttctcat gctccgtgat gcatgaggct 1320 ctgcacaacc actacacgca gaagagcctc tccctgtctc cgggtaaa 1368 |
| 151 | H3 variable region | Gln Val Gln Leu Val Gln Ser Gly Ala Glu Val Lys Lys Pro Gly Ala Ser Val Lys Val Ser Cys Lys Val Ser Gly Glu Ile Ser Thr Gly Tyr Tyr Phe His Phe Val Arg Arg Arg Pro Gly Lys Gly Leu Glu Trp Met Gly Arg Ile Asp Pro Glu Asp Asp Ser Thr Lys Tyr Ala Glu Arg Phe Lys Asp Arg Val Thr Met Thr Ala Asp Thr Ser Thr Asp Thr Ala Tyr Met Glu Leu Ser Ser Leu Arg Ser Glu Asp Thr Ala Thr Tyr Phe Cys Thr Thr Trp Arg Ile Tyr Arg Asp Ser Ser Gly Arg Pro Phe Tyr Val Met Asp Ala Trp Gly Gln Gly Thr Leu Val Thr Val Ser Ser |
| 152 | H3 variable region (PN) | caggtccagc tggtacagtc tggggctgag gtgaagaagc ctggggcctc agtgaaggtc 60 tcctgcaagg tttccggaga aataagtact ggatactatt tccactttgt gcgacgaagg 120 cctggaaaag ggcttgagtg gatgggaagg attgatcctg aggatgatag tactaaatat 180 gctgagaggt tcaaagacag agtcaccatg accgcagaca catctacaga cacagcctac 240 atggagctga gcagcctgag atctgaggac acggccactt atttttgtac cacatggcgg 300 atataccgag atagttctgg ccgccccttc tatgttatgg atgcctgggg ccaagggaca 360 ctagtcacag tctcctca 378 |
| 153 | L1 light chain | Asp Ile Gln Met Thr Gln Ser Pro Ser Ser Val Ser Ala Ser Val Gly Asp Arg Val Thr Ile Thr Cys Leu Ala Ser Glu Asp Ile Tyr Thr Tyr Leu Thr Trp Tyr Gln Gln Lys Pro Gly Lys Ala Pro Lys Leu Leu Ile Tyr Gly Ala Asn Lys Leu Gln Asp Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Leu Gln Gly Ser Lys Phe Pro Leu Thr Phe Gly Gln Gly Thr Lys Leu Glu Ile Lys Arg Thr Val Ala Ala Pro Ser Val Phe Ile Phe Pro Pro Ser |

TABLE 3-continued

Table of Sequences

| SEQ ID NO | DESCRIPTION | SEQUENCE |
|---|---|---|
| | | Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu Lys His Lys Val Tyr Ala Cys Glu Val Thr His Gln Gly Leu Ser Ser Pro Val Thr Lys Ser Phe Asn Arg Gly Glu Cys |
| 154 | L1 light chain (PN) | gacatccaga tgacccagtc tccatcttct gtgtctgcat ctgtaggaga cagagtcacc 60 atcacttgtc tggcaagtga ggacatatac acttatttaa catggtatca gcagaaacca 120 gggaaagccc ctaagctcct gatctatggt gcaaataagt tgcaagatgg ggtcccatca 180 aggttcagcg gcagtggatc tgggacagat ttcactctca ctatcagcag cctgcagcct 240 gaagattttg caacttacta ttgtctacag ggttccaagt ttccgctcac gtttggccag 300 gggaccaagc tggagatcaa acgtacggtg gctgcaccat ctgtcttcat cttcccgcca 360 tctgatgagc agttgaaatc tggaactgcc tctgttgtgt gcctgctgaa taacttctat 420 cccagagagg ccaaagtaca gtggaaggtg gacaacgccc tccaatcggg taactcccag 480 gagagtgtca cagagcagga cagcaaggac agcacctaca gcctcagcag caccctgacg 540 ctgagcaaag cagactacga gaaacacaaa gtctacgcct gcgaagtcac ccatcagggc 600 ctgagctcgc ccgtcacaaa gagcttcaac aggggagagt gt 642 |
| 155 | L1 variable region | Asp Ile Gln Met Thr Gln Ser Pro Ser Ser Val Ser Ala Ser Val Gly Asp Arg Val Thr Ile Thr Cys Leu Ala Ser Glu Asp Ile Tyr Thr Tyr Leu Thr Trp Tyr Gln Gln Lys Pro Gly Lys Ala Pro Lys Leu Leu Ile Tyr Gly Ala Asn Lys Leu Gln Asp Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Leu Gln Gly Ser Lys Phe Pro Leu Thr Phe Gly Gln Gly Thr Lys Leu Glu Ile Lys |
| 156 | L1 variable region (PN) | gacatccaga tgacccagtc tccatcttct gtgtctgcat ctgtaggaga cagagtcacc 60 atcacttgtc tggcaagtga ggacatatac acttatttaa catggtatca gcagaaacca 120 gggaaagccc ctaagctcct gatctatggt gcaaataagt tgcaagatgg ggtcccatca 180 aggttcagcg gcagtggatc tgggacagat ttcactctca ctatcagcag cctgcagcct 240 gaagattttg caacttacta ttgtctacag ggttccaagt ttccgctcac gtttggccag 300 gggaccaagc tggagatcaa a 321 |
| 157 | L3 light chain | Asp Ile Gln Met Thr Gln Ser Pro Ser Ser Val Ser Ala Ser Val Gly Asp Arg Val Thr Ile Thr Cys Leu Ala Ser Glu Asp Ile Tyr Thr Tyr Leu Thr Trp Tyr Gln Gln Lys Pro Gly Lys Ala Pro Gln Leu Leu Ile Tyr Gly Ala Asn Lys Leu Gln Asp Gly Val Pro Ser Arg Phe Ser Gly Ser Gly Ser Gly Thr Asp Tyr Thr Leu Thr Ile Ser Ser Leu Gln Pro Glu Asp Glu Gly Asp Tyr Tyr Cys Leu Gln Gly Ser Lys Phe Pro Leu Thr Phe Gly Gln Gly Thr Lys Leu Glu Ile Lys Arg Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu |

TABLE 3-continued

| Table of Sequences | | |
|---|---|---|
| SEQ ID NO | DESCRIPTION | SEQUENCE |
| | | Lys His Lys Val Tyr Ala Cys Glu Val Thr His<br>Gln Gly Leu Ser Ser Pro Val Thr Lys Ser Phe<br>Asn Arg Gly Glu Cys |
| 158 | L3 light chain (PN) | gacatccaga tgacccagtc tccatcttct gtgtctgcat<br>etgtaggaga cagagtcacc 60<br>atcacttgtc tggcaagtga ggacatatac acttatttaa<br>catggtatca gcagaaacca 120<br>gggaaagccc ctcaactcct gatctatggt gcaaataagt<br>tgcaagatgg ggtcccatca 180<br>aggttcagcg gcagtggatc tgggacagat tatactctca<br>ctatcagcag cctgcagcct 240<br>gaagatgaag ggattacta ttgtctacag ggttccaagt<br>ttccgctcac gtttggccag 300<br>gggaccaagc tggagatcaa acgtacggtg gctgcaccat<br>ctgtcttcat cttcccgcca 360<br>tctgatgagc agttgaaatc tggaactgcc tctgttgtgt<br>gcctgctgaa taacttctat 420<br>cccagagagg ccaaagtaca gtggaaggtg gacaacgccc<br>tccaatcggg taactcccag 480<br>gagagtgtca cagagcagga cagcaaggac agcacctaca<br>gcctcagcag caccctgacg 540<br>ctgagcaaag cagactacga gaaacacaaa gtctacgcct<br>gcgaagtcac ccatcagggc 600<br>ctgagctcgc ccgtcacaaa gagcttcaac aggggagagt<br>gttag 645 |
| 159 | L3 variable region | Asp Ile Gln Met Thr Gln Ser Pro Ser Ser Val<br>Ser Ala Ser Val Gly Asp Arg Val Thr Ile Thr<br>Cys Leu Ala Ser Glu Asp Ile Tyr Thr Tyr Leu<br>Thr Trp Tyr Gln Gln Lys Pro Gly Lys Ala Pro<br>Gln Leu Leu Ile Tyr Gly Ala Asn Lys Leu Gln<br>Asp Gly Val Pro Ser Arg Phe Ser Gly Ser Gly<br>Ser Gly Thr Asp Tyr Thr Leu Thr Ile Ser Ser<br>Leu Gln Pro Glu Asp Glu Gly Asp Tyr Tyr Cys<br>Leu Gln Gly Ser Lys Phe Pro Leu Thr Phe Gly<br>Gln Gly Thr Lys Leu Glu Ile Lys |
| 160 | L3 variable region (PN) | gacatccaga tgacccagtc tccatcttct gtgtctgcat<br>ctgtaggaga cagagtcacc 60<br>atcacttgtc tggcaagtga ggacatatac acttatttaa<br>catggtatca gcagaaacca 120<br>gggaaagccc ctcaactcct gatctatggt gcaaataagt<br>tgcaagatgg ggtcccatca 180<br>aggttcagcg gcagtggatc tgggacagat tatactctca<br>ctatcagcag cctgcagcct 240<br>gaagatgaag ggattacta ttgtctacag ggttccaagt<br>ttccgctcac gtttggccag 300<br>gggaccaagc tggagatcaa a<br>321 |
| 161 | 2c10 rat-human IgG1 chimera | Glu Val Gln Leu Gln Gln Ser Gly Ala Glu Leu<br>Val Arg Pro Gly Thr Ser Val Lys Leu Ser Cys<br>Lys Val Ser Gly Glu Ile Ser Thr Gly Tyr Tyr<br>Phe His Phe Val Arg Arg Arg Pro Gly Gln Gly<br>Leu Glu Trp Ile Gly Arg Ile Asp Pro Glu Asp<br>Asp Ser Thr Lys Tyr Ala Glu Arg Phe Lys Asp<br>Arg Ala Thr Leu Thr Ala Gln Thr Ser Ser Asn<br>Thr Ala Tyr Leu Asn Leu Ser Ser Leu Thr Ser<br>Glu Asp Thr Ala Thr Tyr Phe Cys Thr Thr Trp<br>Arg Ile Tyr Arg Asp Ser Ser Gly Arg Pro Phe<br>Tyr Val Met Asp Ala Trp Gly Gln Gly Thr Leu<br>Val Thr Val Ser Ser Ala Ser Thr Lys Gly Pro<br>Ser Val Phe Pro Leu Ala Pro Ser Ser Lys Ser<br>Thr Ser Gly Gly Thr Ala Ala Leu Gly Cys Leu<br>Val Lys Asp Tyr Phe Pro Glu Pro Val Thr Val<br>Ser Trp Asn Ser Gly Ala Leu Thr Ser Gly Val<br>His Thr Phe Pro Ala Val Leu Gln Ser Ser Gly<br>Leu Tyr Ser Leu Ser Ser Val Val Thr Val Pro<br>Ser Ser Ser Leu Gly Thr Gln Thr Tyr Ile Cys<br>Asn Val Asn His Lys Pro Ser Asn Thr Lys Val<br>Asp Lys Lys Val Glu Pro Lys Ser Cys Asp Lys<br>Thr His Thr Cys Pro Pro Cys Pro Ala Pro Glu<br>Leu Leu Gly Gly Pro Ser Val Phe Leu Phe Pro |

TABLE 3-continued

Table of Sequences

| SEQ ID NO | DESCRIPTION | SEQUENCE |
|---|---|---|
| | | Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys |
| 162 | 2c10 rat-human IgG1 chimera (PN) | gaggtccagc tacagcagtc tggggctgag cttgtgagac ctgggacctc tgtgaagtta 60 tcttgcaaag tttctggcga aataagtaca ggatactatt tccactttgt gaggcgaagg 120 cctggacagg gtctggaatg gataggaagg attgatcctg aggatgatag tactaaatat 180 gctgagaggt tcaaagacag ggcgacgctc actgcacaaa catcctccaa cacagcctac 240 ctgaacctca gcagcctgac ctctgaggac actgcaactt atttttgtac cacatggcgg 300 atataccgag atagttctgg ccgccccttc tatgttatgg atgcctgggg tcaaggaaca 360 ctagtcacag tctcctcagc ctccaccaag ggcccatcgg tcttccccct ggcaccctcc 420 tccaagagca cctctggggg cacagcggcc ctgggctgcc tggtcaagga ctacttcccc 480 gaaccggtga cggtgtcgtg gaactcaggc gccctgacca gcggcgtgca caccttcccg 540 gctgtcctac agtcctcagg actctactcc ctcagcagcg tggtgaccgt gccctccagc 600 agcttgggca cccagaccta catctgcaac gtgaatcaca agcccagcaa caccaaggtg 660 gacaagaaag ttgagcccaa atcttgtgac aaaactcaca catgcccacc gtgcccagca 720 cctgaactcc tggggggacc gtcagtcttc ctcttccccc caaaacccaa ggacaccctc 780 atgatctccc ggacccctga ggtcacatgc gtggtggtgg acgtgagcca cgaagaccct 840 gaggtcaagt tcaactggta cgtggacggc gtggaggtgc ataatgccaa gacaaagccg 900 cgggaggagc agtacaacag cacgtaccgt gtggtcagcg tcctcaccgt cctgcaccag 960 gactggctga atggcaagga gtacaagtgc aaggtctcca acaaagccct cccagccccc 1020 atcgagaaaa ccatctccaa agccaaaggg cagccccgag aaccacaggt gtacaccctg 1080 cccccatccc gggatgagct gaccaagaac caggtcagcc tgacctgcct ggtcaaaggc 1140 ttctatccca gcgacatcgc cgtggagtgg gagagcaatg ggcagccgga gaacaactac 1200 aagaccacgc ctcccgtgct ggactccgac ggctccttct tcctctacag caagctcacc 1260 gtggacaaga gcaggtggca gcaggggaac gtcttctcat gctccgtgat gcatgaggct 1320 ctgcacaacc actacacgca gaagagcctc tccctgtctc cgggtaaa 1368 |
| 163 | 2c10 rat-human CKappa chimera | Asp Ile Gln Met Thr Gln Ser Pro Ala Ser Leu Ser Ala Ser Leu Gly Glu Thr Val Ser Ile Glu Cys Leu Ala Ser Glu Asp Ile Tyr Thr Tyr Leu Thr Trp Tyr Gln Gln Lys Pro Gly Lys Ser Pro Gln Leu Leu Ile Tyr Gly Ala Asn Lys Leu Gln Asp Gly Val Pro Ser Arg Phe Ser Gly Ser Gly Ser Gly Thr Gln Tyr Ser Leu Lys Ile Ser Gly |

TABLE 3-continued

| Table of Sequences | | |
|---|---|---|
| SEQ ID NO | DESCRIPTION | SEQUENCE |
| | | Ile Gln Pro Glu Asp Glu Gly Asp Tyr Phe Cys Leu Gln Gly Ser Lys Phe Pro Leu Thr Phe Gly Ser Gly Thr Lys Leu Glu Ile Lys Arg Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu Lys His Lys Val Tyr Ala Cys Glu Val Thr His Gln Gly Leu Ser Ser Pro Val Thr Lys Ser Phe Asn Arg Gly Glu Cys |
| 164 | 2c10 rat-human CKappa chimera (PN) | gacattcaaa tgacccagtc tccagcttcc ctgtctgcat ctctgggaga aactgtctcc 60 atcgaatgtc tggcaagtga ggacatatac acttatttaa catggtatca gcagaaacca 120 gggaaatctc ctcaactcct gatctatggt gcaaataagt tgcaagatgg ggtcccatca 180 cggttcagtg gcagtggatc tggcacacag tattctctca agatcagcgg catacaacct 240 gaagatgaag gggattattt ctgtctacag ggttccaagt ttccgctcac gttcggttct 300 gggaccaagc tggagatcaa acgtacggtg gctgcaccat ctgtcttcat cttcccgcca 360 tctgatgagc agttgaaatc tggaactgcc tctgttgtgt gcctgctgaa taacttctat 420 cccagagagg ccaaagtaca gtggaaggtg gacaacgccc tccaatcggg taactcccag 480 gagagtgtca cagagcagga cagcaaggac agcacctaca gcctcagcag caccctgacg 540 ctgagcaaag cagactacga gaaacacaaa gtctacgcct gcgaagtcac ccatcagggc 600 ctgagctcgc ccgtcacaaa gagcttcaac aggggagagt gt 642 |
| 165 | Heavy chain acceptor framework | Gln Val Gln Leu Val Gln Ser Gly Ala Glu Val Lys Lys Pro Gly Ala Ser Val Lys Val Ser Cys Lys Val Ser Gly Tyr Thr Leu Thr Glu Leu Ser Met His Trp Val Arg Gln Ala Pro Gly Lys Gly Leu Glu Trp Met Gly Gly Phe Asp Pro Glu Asp Gly Glu Thr Ile Tyr Ala Gln Lys Phe Gln Gly Arg Val Thr Met Thr Glu Asp Thr Ser Thr Asp Thr Ala Tyr Met Glu Leu Ser Ser Leu Arg Ser Glu Asp Thr Ala Val Tyr Tyr Cys Ala Thr |
| 166 | Light chain acceptor framework | Asp Ile Gln Met Thr Gln Ser Pro Ser Ser Val Ser Ala Ser Val Gly Asp Arg Val Thr Ile Thr Cys Arg Ala Ser Gln Gly Ile Ser Ser Trp Leu Ala Trp Tyr Gln Gln Lys Pro Gly Lys Ala Pro Lys Leu Leu Ile Tyr Ala Ala Ser Ser Leu Gln Ser Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Gln Gln Ala Asn Ser Phe Pro |
| 167 | JH6 amino acid sequence added to SEQ ID NO: 37 | Trp Gly Gln Gly Thr Leu Val Thr Val Ser Ser |
| 168 | Jkappa 2 amino acid sequence added to SEQ ID NO: 38 | Phe Gly Gln Gly Thr Lys Leu Glu Ile Lys |

What is claimed is:

1. A method of treating a condition associated with elevated IL-18, comprising administering to a subject in need thereof an effective amount of an anti-IL-18 antibody wherein the anti-IL-18 antibody comprises:

(a) a HCDR1 having an amino acid sequence of SEQ ID NO: 122;

(b) a HCDR2 having an amino acid sequence of SEQ ID NO: 123;

(c) a HCDR3 having an amino acid sequence of SEQ ID NO: 124;

(d) a LCDR1 having an amino acid sequence of SEQ ID NO: 126;

(e) a LCDR2 having an amino acid sequence of SEQ ID NO: 127; and (f) a LCDR3 having an amino acid sequence of SEQ ID NO: 128 and wherein the condition associated with elevated IL-18 comprises acute respiratory distress syndrome (ARDS), optionally wherein the ARDS is associated with a bacterial or viral infection, optionally coronavirus infection.

2. The method of claim 1, wherein the method further comprises the following steps prior to administering the anti-IL-18 antibody:

(a) contacting a biological sample isolated from the subject with an anti-IL-18 antibody;

(b) incubating the biological sample to allow an anti-IL-18 antibody to bind to IL-18; and (c) detecting the presence of complexes formed between an anti-IL-18 antibody and IL-18 in the biological sample, optionally wherein the detection of IL-18 indicates that treatment of the condition associated with elevated IL-18 with an anti-IL-18 antibody will be effective.

3. The method of claim 1, wherein the anti-IL-18 antibody comprises a VH domain having an amino acid sequence that is at least 90% identical to the full sequence of SEQ ID NO:

121, and/or wherein the anti-IL-18 antibody comprises a VH domain having an amino acid sequence that is identical to the full sequence of SEQ ID NO: 121.

4. The method of claim 1, wherein the anti-IL-18 antibody comprises a VL domain having an amino acid sequence that is at least 90% identical to the full sequence of SEQ ID NO: 125, and/or wherein the anti-IL-18 antibody comprises a VL domain having an amino acid sequence that is identical to the full sequence of SEQ ID NO: 125.

5. The method of claim 1, wherein the anti-IL-18 antibody comprises an antibody VH domain and an antibody VL domain, wherein the amino acid sequence of the antibody VH domain and the antibody VL domain are at least 90% identical to the full sequence of SEQ ID NOS: 121 and 125.

6. The method of claim 1, wherein the anti-IL-18 antibody administered to the subject suppresses T cell activation, suppresses increased expression of cytokines, optionally suppresses increased expression of IFN-γ; and/or reduces the subject's risk of mortality or morbidity.

7. The method of claim 1, wherein the subject is human.

8. The method of claim 1, wherein the subject has pneumonia, acute lung injury (ALI), and/or mild, moderate and/or severe coronavirus infection.

9. The method of claim 8, wherein the subject is at the Early Infection (Stage I), the Pulmonary Phase (Stage II), or the Hyperinflammation Phase (Stage III) of a coronavirus infection.

10. The method of claim 1, wherein the subject is a pediatric subject.

11. The method of claim 1, wherein the subject is an adult.

* * * * *

SEQUENCE LISTING

<160> NUMBER OF SEQ ID NOS: 168

<210> SEQ ID NO 1
<211> LENGTH: 125
<212> TYPE: PRT
<213> ORGANISM: Artificial Sequence
<220> FEATURE:
<223> OTHER INFORMATION: Synthetic: Antibody 1 VH

<400> SEQUENCE: 1

```
Gln Val Gln Leu Gln Gln Ser Gly Pro Arg Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Ala Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Pro Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Asp Gly Asp Ala Arg Ala Asp Phe Phe
            100                 105                 110

Asp Val Trp Gly Arg Gly Thr Leu Val Thr Val Ser Ser
        115                 120                 125
```

<210> SEQ ID NO 2
<211> LENGTH: 7
<212> TYPE: PRT
<213> ORGANISM: Artificial Sequence
<220> FEATURE:
<223> OTHER INFORMATION: Synthetic: Antibody 1 HCDR1

<400> SEQUENCE: 2

```
Ser Gly Gly Tyr Tyr Trp Ser
1               5
```

<210> SEQ ID NO 3
<211> LENGTH: 16
<212> TYPE: PRT
<213> ORGANISM: Artificial Sequence
<220> FEATURE:
<223> OTHER INFORMATION: Synthetic: Antibody 1 HCDR2

<400> SEQUENCE: 3

```
Ser Ile Tyr Tyr Ser Gly Ser Thr Tyr Tyr Asn Pro Ser Leu Lys Ser
1               5                   10                  15
```

<210> SEQ ID NO 4
<211> LENGTH: 15
<212> TYPE: PRT
<213> ORGANISM: Artificial Sequence
<220> FEATURE:
<223> OTHER INFORMATION: Synthetic: Antibody 1 HCDR3

<400> SEQUENCE: 4

```
Thr Pro Ala Tyr Asp Gly Asp Ala Arg Ala Asp Phe Phe Asp Val
1               5                   10                  15
```

<210> SEQ ID NO 5
<211> LENGTH: 107
<212> TYPE: PRT

<213> ORGANISM: Artificial Sequence
<220> FEATURE:
<223> OTHER INFORMATION: Synthetic: Antibody 1 VL

<400> SEQUENCE: 5

```
Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys
            100                 105
```

<210> SEQ ID NO 6
<211> LENGTH: 11
<212> TYPE: PRT
<213> ORGANISM: Artificial Sequence
<220> FEATURE:
<223> OTHER INFORMATION: Synthetic: Antibody 1 LCDR1

<400> SEQUENCE: 6

```
Arg Ala Ser Gln Gly Ile Ser Ser Trp Leu Ala
1               5                   10
```

<210> SEQ ID NO 7
<211> LENGTH: 7
<212> TYPE: PRT
<213> ORGANISM: Artificial Sequence
<220> FEATURE:
<223> OTHER INFORMATION: Synthetic: Antibody 1 LCDR2

<400> SEQUENCE: 7

```
Lys Ala Ser Thr Leu Glu Ser
1               5
```

<210> SEQ ID NO 8
<211> LENGTH: 9
<212> TYPE: PRT
<213> ORGANISM: Artificial Sequence
<220> FEATURE:
<223> OTHER INFORMATION: Synthetic: Antibody 1 LCDR3

<400> SEQUENCE: 8

```
Gln Gln Ser Tyr Ser Thr Pro Trp Thr
1               5
```

<210> SEQ ID NO 9
<211> LENGTH: 125
<212> TYPE: PRT
<213> ORGANISM: Artificial Sequence
<220> FEATURE:
<223> OTHER INFORMATION: Synthetic: Antibody 1_GL VH

<400> SEQUENCE: 9

```
Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Asp Gly Asp Ala Arg Ala Asp Phe Phe
            100                 105                 110

Asp Val Trp Gly Arg Gly Thr Leu Val Thr Val Ser Ser
        115                 120                 125


<210> SEQ ID NO 10
<211> LENGTH: 7
<212> TYPE: PRT
<213> ORGANISM: Artificial Sequence
<220> FEATURE:
<223> OTHER INFORMATION: Synthetic: Antibody 1_GL HCDR1

<400> SEQUENCE: 10

Ser Gly Gly Tyr Tyr Trp Ser
1               5


<210> SEQ ID NO 11
<211> LENGTH: 16
<212> TYPE: PRT
<213> ORGANISM: Artificial Sequence
<220> FEATURE:
<223> OTHER INFORMATION: Synthetic: Antibody 1_GL HCDR2

<400> SEQUENCE: 11

Ser Ile Tyr Tyr Ser Gly Ser Thr Tyr Tyr Asn Pro Ser Leu Lys Ser
1               5                   10                  15


<210> SEQ ID NO 12
<211> LENGTH: 15
<212> TYPE: PRT
<213> ORGANISM: Artificial Sequence
<220> FEATURE:
<223> OTHER INFORMATION: Synthetic: Antibody 1_GL HCDR3

<400> SEQUENCE: 12

Thr Pro Ala Tyr Asp Gly Asp Ala Arg Ala Asp Phe Phe Asp Val
1               5                   10                  15


<210> SEQ ID NO 13
<211> LENGTH: 107
<212> TYPE: PRT
<213> ORGANISM: Artificial Sequence
<220> FEATURE:
<223> OTHER INFORMATION: Synthetic: Antibody 1_GL VL

<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45
```

```
Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys
            100                 105


<210> SEQ ID NO 14
<211> LENGTH: 11
<212> TYPE: PRT
<213> ORGANISM: Artificial Sequence
<220> FEATURE:
<223> OTHER INFORMATION: Synthetic: Antibody 1_GL LCDR1

<400> SEQUENCE: 14

Arg Ala Ser Gln Gly Ile Ser Ser Trp Leu Ala
1               5                   10


<210> SEQ ID NO 15
<211> LENGTH: 7
<212> TYPE: PRT
<213> ORGANISM: Artificial Sequence
<220> FEATURE:
<223> OTHER INFORMATION: Synthetic: Antibody 1_GL LCDR2

<400> SEQUENCE: 15

Lys Ala Ser Thr Leu Glu Ser
1               5


<210> SEQ ID NO 16
<211> LENGTH: 9
<212> TYPE: PRT
<213> ORGANISM: Artificial Sequence
<220> FEATURE:
<223> OTHER INFORMATION: Synthetic: Antibody 1_GL LCDR3

<400> SEQUENCE: 16

Gln Gln Ser Tyr Ser Thr Pro Trp Thr
1               5


<210> SEQ ID NO 17
<211> LENGTH: 125
<212> TYPE: PRT
<213> ORGANISM: Artificial Sequence
<220> FEATURE:
<223> OTHER INFORMATION: Synthetic: Antibody 2 VH

<400> SEQUENCE: 17

Gln Val Gln Leu Gln Gln Ser Gly Pro Arg Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Ala Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Pro Lys Asn Gln Phe
65                  70                  75                  80

Ser Leu Lys Leu Ser Ser Val Thr Ala Ala Asp Thr Ala Val Tyr Tyr
                85                  90                  95
```

Cys Ala Arg Thr Pro Ala Tyr Asp Gly Asp Ala Arg Ala Asp Phe Phe
100 105 110

Asp Val Trp Gly Arg Gly Thr Leu Val Thr Val Ser Ser
115 120 125

<210> SEQ ID NO 18
<211> LENGTH: 7
<212> TYPE: PRT
<213> ORGANISM: Artificial Sequence
<220> FEATURE:
<223> OTHER INFORMATION: Synthetic: Antibody 2 HCDR1

<400> SEQUENCE: 18

Ser Gly Gly Tyr Tyr Trp Ser
1 5

<210> SEQ ID NO 19
<211> LENGTH: 16
<212> TYPE: PRT
<213> ORGANISM: Artificial Sequence
<220> FEATURE:
<223> OTHER INFORMATION: Synthetic: Antibody 2 HCDR2

<400> SEQUENCE: 19

Ser Ile Tyr Tyr Ser Gly Ser Thr Tyr Tyr Asn Pro Ser Leu Lys Ser
1 5 10 15

<210> SEQ ID NO 20
<211> LENGTH: 15
<212> TYPE: PRT
<213> ORGANISM: Artificial Sequence
<220> FEATURE:
<223> OTHER INFORMATION: Synthetic: Antibody 2 HCDR3

<400> SEQUENCE: 20

Thr Pro Ala Tyr Asp Gly Asp Ala Arg Ala Asp Phe Phe Asp Val
1 5 10 15

<210> SEQ ID NO 21
<211> LENGTH: 107
<212> TYPE: PRT
<213> ORGANISM: Artificial Sequence
<220> FEATURE:
<223> OTHER INFORMATION: Synthetic: Antibody 2 VL

<400> SEQUENCE: 21

Asp Ile Val Met Thr Gln Ser Pro Ser Thr Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Arg Ala Pro Lys Val Leu Ile
35 40 45

Tyr Lys Ala Ser Thr Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Asp Ile Ser Phe Pro Pro Trp
85 90 95

Thr Phe Gly Gln Gly Thr Lys Leu Glu Ile Lys
100 105

<210> SEQ ID NO 22
<211> LENGTH: 11

<212> TYPE: PRT
<213> ORGANISM: Artificial Sequence
<220> FEATURE:
<223> OTHER INFORMATION: Synthetic: Antibody 2 LCDR1

<400> SEQUENCE: 22

Arg Ala Ser Gln Gly Ile Ser Ser Trp Leu Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic: Antibody 2 LCDR2

<400> SEQUENCE: 23

Lys Ala Ser Thr Leu Glu Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic: Antibody 2 LCDR3

<400> SEQUENCE: 24

Gln Asp Ile Ser Phe Pro Pro Trp Thr
1               5

<210> SEQ ID NO 25
<211> LENGTH: 125
<212> TYPE: PRT
<213> ORGANISM: Artificial Sequence
<220> FEATURE:
<223> OTHER INFORMATION: Synthetic: Antibody 3 VH

<400> SEQUENCE: 25

Gln Val Gln Leu Gln Gln Ser Gly Pro Arg Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Ala Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Pro Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Asp Gly Asp Ala Arg Ala Asp Phe Phe
            100                 105                 110

Asp Val Trp Gly Arg Gly Thr Leu Val Thr Val Ser Ser
        115                 120                 125

<210> SEQ ID NO 26
<211> LENGTH: 7
<212> TYPE: PRT
<213> ORGANISM: Artificial Sequence
<220> FEATURE:
<223> OTHER INFORMATION: Synthetic: Antibody 3 HCDR1

<400> SEQUENCE: 26

Ser Gly Gly Tyr Tyr Trp Ser
1 5

<210> SEQ ID NO 27
<211> LENGTH: 16
<212> TYPE: PRT
<213> ORGANISM: Artificial Sequence
<220> FEATURE:
<223> OTHER INFORMATION: Synthetic: Antibody 3 HCDR2

<400> SEQUENCE: 27

Ser Ile Tyr Tyr Ser Gly Ser Thr Tyr Tyr Asn Pro Ser Leu Lys Ser
1 5 10 15

<210> SEQ ID NO 28
<211> LENGTH: 15
<212> TYPE: PRT
<213> ORGANISM: Artificial Sequence
<220> FEATURE:
<223> OTHER INFORMATION: Synthetic: Antibody 3 HCDR3

<400> SEQUENCE: 28

Thr Pro Ala Tyr Asp Gly Asp Ala Arg Ala Asp Phe Phe Asp Val
1 5 10 15

<210> SEQ ID NO 29
<211> LENGTH: 107
<212> TYPE: PRT
<213> ORGANISM: Artificial Sequence
<220> FEATURE:
<223> OTHER INFORMATION: Synthetic: Antibody 3 VL

<400> SEQUENCE: 29

Asp Ile Val Met Thr Gln Ser Pro Ser Thr Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Arg Ala Pro Lys Val Leu Ile
35 40 45

Tyr Lys Ala Ser Thr Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Leu Tyr Pro Pro Trp
85 90 95

Thr Phe Gly Gln Gly Thr Lys Leu Glu Ile Lys
100 105

<210> SEQ ID NO 30
<211> LENGTH: 11
<212> TYPE: PRT
<213> ORGANISM: Artificial Sequence
<220> FEATURE:
<223> OTHER INFORMATION: Synthetic: Antibody 3 LCDR1

<400> SEQUENCE: 30

Arg Ala Ser Gln Gly Ile Ser Ser Trp Leu Ala
1 5 10

<210> SEQ ID NO 31
<211> LENGTH: 7

<212> TYPE: PRT
<213> ORGANISM: Artificial Sequence
<220> FEATURE:
<223> OTHER INFORMATION: Synthetic: Antibody 3 LCDR2

<400> SEQUENCE: 31

Lys Ala Ser Thr Leu Glu Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic: Antibody 3 LCDR3

<400> SEQUENCE: 32

Gln Gln Ser Leu Tyr Pro Pro Trp Thr
1               5

<210> SEQ ID NO 33
<211> LENGTH: 125
<212> TYPE: PRT
<213> ORGANISM: Artificial Sequence
<220> FEATURE:
<223> OTHER INFORMATION: Synthetic: Antibody 4 VH

<400> SEQUENCE: 33

Gln Val Gln Leu Gln Gln Ser Gly Pro Arg Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Ala Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Pro Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Asp Gly Asp Ala Arg Ala Asp Phe Phe
            100                 105                 110

Asp Val Trp Gly Arg Gly Thr Leu Val Thr Val Ser Ser
        115                 120                 125

<210> SEQ ID NO 34
<211> LENGTH: 7
<212> TYPE: PRT
<213> ORGANISM: Artificial Sequence
<220> FEATURE:
<223> OTHER INFORMATION: Synthetic: Antibody 4 HCDR1

<400> SEQUENCE: 34

Ser Gly Gly Tyr Tyr Trp Ser
1               5

<210> SEQ ID NO 35
<211> LENGTH: 16
<212> TYPE: PRT
<213> ORGANISM: Artificial Sequence
<220> FEATURE:
<223> OTHER INFORMATION: Synthetic: Antibody 4 HCDR2

<400> SEQUENCE: 35

Ser Ile Tyr Tyr Ser Gly Ser Thr Tyr Tyr Asn Pro Ser Leu Lys Ser
1 5 10 15

<210> SEQ ID NO 36
<211> LENGTH: 15
<212> TYPE: PRT
<213> ORGANISM: Artificial Sequence
<220> FEATURE:
<223> OTHER INFORMATION: Synthetic: Antibody 4 HCDR3

<400> SEQUENCE: 36

Thr Pro Ala Tyr Asp Gly Asp Ala Arg Ala Asp Phe Phe Asp Val
1 5 10 15

<210> SEQ ID NO 37
<211> LENGTH: 107
<212> TYPE: PRT
<213> ORGANISM: Artificial Sequence
<220> FEATURE:
<223> OTHER INFORMATION: Synthetic: Antibody 4 VL

<400> SEQUENCE: 37

Asp Ile Val Met Thr Gln Ser Pro Ser Thr Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Arg Ala Pro Lys Val Leu Ile
35 40 45

Tyr Lys Ala Ser Thr Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser His His Pro Asn Trp
85 90 95

Asp Phe Gly Gln Gly Thr Lys Leu Glu Ile Lys
100 105

<210> SEQ ID NO 38
<211> LENGTH: 11
<212> TYPE: PRT
<213> ORGANISM: Artificial Sequence
<220> FEATURE:
<223> OTHER INFORMATION: Synthetic: Antibody 4 LCDR1

<400> SEQUENCE: 38

Arg Ala Ser Gln Gly Ile Ser Ser Trp Leu Ala
1 5 10

<210> SEQ ID NO 39
<211> LENGTH: 7
<212> TYPE: PRT
<213> ORGANISM: Artificial Sequence
<220> FEATURE:
<223> OTHER INFORMATION: Synthetic: Antibody 4 LCDR2

<400> SEQUENCE: 39

Lys Ala Ser Thr Leu Glu Ser
1 5

<210> SEQ ID NO 40
<211> LENGTH: 9

<212> TYPE: PRT
<213> ORGANISM: Artificial Sequence
<220> FEATURE:
<223> OTHER INFORMATION: Synthetic: Antibody 4 LCDR3

<400> SEQUENCE: 40

Gln Gln Ser His His Pro Asn Trp Asp
1 5

<210> SEQ ID NO 41
<211> LENGTH: 125
<212> TYPE: PRT
<213> ORGANISM: Artificial Sequence
<220> FEATURE:
<223> OTHER INFORMATION: Synthetic: Antibody 5 VH

<400> SEQUENCE: 41

Gln Val Gln Leu Gln Gln Ser Gly Pro Arg Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln Pro Ala Gly Lys Gly Leu Glu
35 40 45

Trp Ile Gly Ser Ile Tyr Tyr Ser Gly Ser Thr Tyr Tyr Asn Pro Ser
50 55 60

Leu Lys Ser Arg Val Thr Ile Ser Gly Asp Thr Pro Lys Asn Gln Phe
65 70 75 80

Ser Leu Lys Leu Ser Ser Val Thr Ala Ala Asp Thr Ala Val Tyr Tyr
85 90 95

Cys Ala Arg Thr Pro Ala Tyr Asp Gly Asp Ala Arg Ala Asp Phe Phe
100 105 110

Asp Val Trp Gly Arg Gly Thr Leu Val Thr Val Ser Ser
115 120 125

<210> SEQ ID NO 42
<211> LENGTH: 7
<212> TYPE: PRT
<213> ORGANISM: Artificial Sequence
<220> FEATURE:
<223> OTHER INFORMATION: Synthetic: Antibody 5 HCDR1

<400> SEQUENCE: 42

Ser Gly Gly Tyr Tyr Trp Ser
1 5

<210> SEQ ID NO 43
<211> LENGTH: 16
<212> TYPE: PRT
<213> ORGANISM: Artificial Sequence
<220> FEATURE:
<223> OTHER INFORMATION: Synthetic: Antibody 5 HCDR2

<400> SEQUENCE: 43

Ser Ile Tyr Tyr Ser Gly Ser Thr Tyr Tyr Asn Pro Ser Leu Lys Ser
1 5 10 15

<210> SEQ ID NO 44
<211> LENGTH: 15
<212> TYPE: PRT
<213> ORGANISM: Artificial Sequence
<220> FEATURE:
<223> OTHER INFORMATION: Synthetic: Antibody 5 HCDR3

<400> SEQUENCE: 44

Thr Pro Ala Tyr Asp Gly Asp Ala Arg Ala Asp Phe Phe Asp Val
1 5 10 15

<210> SEQ ID NO 45
<211> LENGTH: 107
<212> TYPE: PRT
<213> ORGANISM: Artificial Sequence
<220> FEATURE:
<223> OTHER INFORMATION: Synthetic: Antibody 5 VL

<400> SEQUENCE: 45

Asp Ile Val Met Thr Gln Ser Pro Ser Thr Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Arg Ala Pro Lys Val Leu Ile
35 40 45

Tyr Lys Ala Ser Thr Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Leu Ile Pro Gln Trp
85 90 95

Asp Phe Gly Gln Gly Thr Lys Leu Glu Ile Lys
100 105

<210> SEQ ID NO 46
<211> LENGTH: 11
<212> TYPE: PRT
<213> ORGANISM: Artificial Sequence
<220> FEATURE:
<223> OTHER INFORMATION: Synthetic: Antibody 5 LCDR1

<400> SEQUENCE: 46

Arg Ala Ser Gln Gly Ile Ser Ser Trp Leu Ala
1 5 10

<210> SEQ ID NO 47
<211> LENGTH: 7
<212> TYPE: PRT
<213> ORGANISM: Artificial Sequence
<220> FEATURE:
<223> OTHER INFORMATION: Synthetic: Antibody 5 LCDR2

<400> SEQUENCE: 47

Lys Ala Ser Thr Leu Glu Ser
1 5

<210> SEQ ID NO 48
<211> LENGTH: 9
<212> TYPE: PRT
<213> ORGANISM: Artificial Sequence
<220> FEATURE:
<223> OTHER INFORMATION: Synthetic: Antibody 5 LCDR3

<400> SEQUENCE: 48

Gln Gln Ser Leu Ile Pro Gln Trp Asp
1 5

<210> SEQ ID NO 49
<211> LENGTH: 125

<212> TYPE: PRT
<213> ORGANISM: Artificial Sequence
<220> FEATURE:
<223> OTHER INFORMATION: Synthetic: Antibody 6 VH

<400> SEQUENCE: 49

Gln Val Gln Leu Gln Gln Ser Gly Pro Arg Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln Pro Ala Gly Lys Gly Leu Glu
35 40 45

Trp Ile Gly Ser Ile Tyr Tyr Ser Gly Ser Thr Tyr Tyr Asn Pro Ser
50 55 60

Leu Lys Ser Arg Val Thr Ile Ser Gly Asp Thr Pro Lys Asn Gln Phe
65 70 75 80

Ser Leu Lys Leu Ser Ser Val Thr Ala Ala Asp Thr Ala Val Tyr Tyr
85 90 95

Cys Ala Arg Thr Pro Ala Tyr Phe Gly Gln Asp Arg Thr Asp Phe Phe
100 105 110

Asp Val Trp Gly Arg Gly Thr Leu Val Thr Val Ser Ser
115 120 125

<210> SEQ ID NO 50
<211> LENGTH: 7
<212> TYPE: PRT
<213> ORGANISM: Artificial Sequence
<220> FEATURE:
<223> OTHER INFORMATION: Synthetic: Antibody 6 HCDR1

<400> SEQUENCE: 50

Ser Gly Gly Tyr Tyr Trp Ser
1 5

<210> SEQ ID NO 51
<211> LENGTH: 16
<212> TYPE: PRT
<213> ORGANISM: Artificial Sequence
<220> FEATURE:
<223> OTHER INFORMATION: Synthetic: Antibody 6 HCDR2

<400> SEQUENCE: 51

Ser Ile Tyr Tyr Ser Gly Ser Thr Tyr Tyr Asn Pro Ser Leu Lys Ser
1 5 10 15

<210> SEQ ID NO 52
<211> LENGTH: 15
<212> TYPE: PRT
<213> ORGANISM: Artificial Sequence
<220> FEATURE:
<223> OTHER INFORMATION: Synthetic: Antibody 6 HCDR3

<400> SEQUENCE: 52

Thr Pro Ala Tyr Phe Gly Gln Asp Arg Thr Asp Phe Phe Asp Val
1 5 10 15

<210> SEQ ID NO 53
<211> LENGTH: 107
<212> TYPE: PRT
<213> ORGANISM: Artificial Sequence
<220> FEATURE:
<223> OTHER INFORMATION: Synthetic: Antibody 6 VL

<400> SEQUENCE: 53

Asp Ile Val Met Thr Gln Ser Pro Ser Thr Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Arg Ala Pro Lys Val Leu Ile
35 40 45

Tyr Lys Ala Ser Thr Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Ala Asn Ile Ala Phe Pro Pro Trp
85 90 95

Thr Phe Gly Gln Gly Thr Lys Leu Glu Ile Lys
100 105

<210> SEQ ID NO 54
<211> LENGTH: 11
<212> TYPE: PRT
<213> ORGANISM: Artificial Sequence
<220> FEATURE:
<223> OTHER INFORMATION: Synthetic: Antibody 6 LCDR1

<400> SEQUENCE: 54

Arg Ala Ser Gln Gly Ile Ser Ser Trp Leu Ala
1 5 10

<210> SEQ ID NO 55
<211> LENGTH: 7
<212> TYPE: PRT
<213> ORGANISM: Artificial Sequence
<220> FEATURE:
<223> OTHER INFORMATION: Synthetic: Antibody 6 LCDR2

<400> SEQUENCE: 55

Lys Ala Ser Thr Leu Glu Ser
1 5

<210> SEQ ID NO 56
<211> LENGTH: 9
<212> TYPE: PRT
<213> ORGANISM: Artificial Sequence
<220> FEATURE:
<223> OTHER INFORMATION: Synthetic: Antibody 6 LCDR3

<400> SEQUENCE: 56

Ala Asn Ile Ala Phe Pro Pro Trp Thr
1 5

<210> SEQ ID NO 57
<211> LENGTH: 125
<212> TYPE: PRT
<213> ORGANISM: Artificial Sequence
<220> FEATURE:
<223> OTHER INFORMATION: Synthetic: Antibody 6_GL VH

<400> SEQUENCE: 57

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Gly
20 25 30

```
Gly Tyr Tyr Trp Ser Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
        115                 120                 125


<210> SEQ ID NO 58
<211> LENGTH: 7
<212> TYPE: PRT
<213> ORGANISM: Artificial Sequence
<220> FEATURE:
<223> OTHER INFORMATION: Synthetic: Antibody 6_GL HCDR1

<400> SEQUENCE: 58

Ser Gly Gly Tyr Tyr Trp Ser
1               5


<210> SEQ ID NO 59
<211> LENGTH: 16
<212> TYPE: PRT
<213> ORGANISM: Artificial Sequence
<220> FEATURE:
<223> OTHER INFORMATION: Synthetic: Antibody 6_GL HCDR2

<400> SEQUENCE: 59

Ser Ile Tyr Tyr Ser Gly Ser Thr Tyr Tyr Asn Pro Ser Leu Lys Ser
1               5                   10                  15


<210> SEQ ID NO 60
<211> LENGTH: 15
<212> TYPE: PRT
<213> ORGANISM: Artificial Sequence
<220> FEATURE:
<223> OTHER INFORMATION: Synthetic: Antibody 6_GL HCDR3

<400> SEQUENCE: 60

Thr Pro Ala Tyr Phe Gly Gln Asp Arg Thr Asp Phe Phe Asp Val
1               5                   10                  15


<210> SEQ ID NO 61
<211> LENGTH: 107
<212> TYPE: PRT
<213> ORGANISM: Artificial Sequence
<220> FEATURE:
<223> OTHER INFORMATION: Synthetic: Antibody 6_GL VL

<400> SEQUENCE: 61

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60
```

Ser Gly Ser Gly Thr Glu Phe Thr Leu Thr Ile Ser Ser Leu Gln Pro
65 70 75 80

Asp Asp Phe Ala Thr Tyr Tyr Cys Ala Asn Ile Ala Phe Pro Pro Trp
85 90 95

Thr Phe Gly Gln Gly Thr Lys Leu Glu Ile Lys
100 105

<210> SEQ ID NO 62
<211> LENGTH: 11
<212> TYPE: PRT
<213> ORGANISM: Artificial Sequence
<220> FEATURE:
<223> OTHER INFORMATION: Synthetic: Antibody 6_GL LCDR1

<400> SEQUENCE: 62

Arg Ala Ser Gln Gly Ile Ser Ser Trp Leu Ala
1 5 10

<210> SEQ ID NO 63
<211> LENGTH: 7
<212> TYPE: PRT
<213> ORGANISM: Artificial Sequence
<220> FEATURE:
<223> OTHER INFORMATION: Synthetic: Antibody 6_GL LCDR2

<400> SEQUENCE: 63

Lys Ala Ser Thr Leu Glu Ser
1 5

<210> SEQ ID NO 64
<211> LENGTH: 9
<212> TYPE: PRT
<213> ORGANISM: Artificial Sequence
<220> FEATURE:
<223> OTHER INFORMATION: Synthetic: Antibody 6_GL

<400> SEQUENCE: 64

Ala Asn Ile Ala Phe Pro Pro Trp Thr
1 5

<210> SEQ ID NO 65
<211> LENGTH: 125
<212> TYPE: PRT
<213> ORGANISM: Artificial Sequence
<220> FEATURE:
<223> OTHER INFORMATION: Synthetic: Antibody 7 VH

<400> SEQUENCE: 65

Gln Val Gln Leu Gln Gln Ser Gly Pro Arg Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln Pro Ala Gly Lys Gly Leu Glu
35 40 45

Trp Ile Gly Ser Ile Tyr Tyr Ser Gly Ser Thr Tyr Tyr Asn Pro Ser
50 55 60

Leu Lys Ser Arg Val Thr Ile Ser Gly Asp Thr Pro Lys Asn Gln Phe
65 70 75 80

Ser Leu Lys Leu Ser Ser Val Thr Ala Ala Asp Thr Ala Val Tyr Tyr
85 90 95

Cys Ala Arg Thr Pro Ala Tyr Phe Gly Gln Asp Arg Thr Asp Phe Phe
100 105 110

```
Asp Val Trp Gly Arg Gly Thr Leu Val Thr Val Ser Ser
        115                 120                 125


<210> SEQ ID NO 66
<211> LENGTH: 7
<212> TYPE: PRT
<213> ORGANISM: Artificial Sequence
<220> FEATURE:
<223> OTHER INFORMATION: Synthetic: Antibody 7 HCDR1

<400> SEQUENCE: 66

Ser Gly Gly Tyr Tyr Trp Ser
1               5


<210> SEQ ID NO 67
<211> LENGTH: 16
<212> TYPE: PRT
<213> ORGANISM: Artificial Sequence
<220> FEATURE:
<223> OTHER INFORMATION: Synthetic: Antibody 7 HCDR2

<400> SEQUENCE: 67

Ser Ile Tyr Tyr Ser Gly Ser Thr Tyr Tyr Asn Pro Ser Leu Lys Ser
1               5                   10                  15


<210> SEQ ID NO 68
<211> LENGTH: 15
<212> TYPE: PRT
<213> ORGANISM: Artificial Sequence
<220> FEATURE:
<223> OTHER INFORMATION: Synthetic: Antibody 7 HCDR3

<400> SEQUENCE: 68

Thr Pro Ala Tyr Phe Gly Gln Asp Arg Thr Asp Phe Phe Asp Val
1               5                   10                  15


<210> SEQ ID NO 69
<211> LENGTH: 107
<212> TYPE: PRT
<213> ORGANISM: Artificial Sequence
<220> FEATURE:
<223> OTHER INFORMATION: Synthetic: Antibody 7 VL

<400> SEQUENCE: 69

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His His Pro Pro Trp
                85                  90                  95

Thr Phe Gly Gln Gly Thr Lys Leu Glu Ile Lys
            100                 105


<210> SEQ ID NO 70
<211> LENGTH: 11
<212> TYPE: PRT
<213> ORGANISM: Artificial Sequence
<220> FEATURE:
```

<223> OTHER INFORMATION: Synthetic: Antibody 7 LCDR1

<400> SEQUENCE: 70

Arg Ala Ser Gln Gly Ile Ser Ser Trp Leu Ala
1 5 10

<210> SEQ ID NO 71
<211> LENGTH: 7
<212> TYPE: PRT
<213> ORGANISM: Artificial Sequence
<220> FEATURE:
<223> OTHER INFORMATION: Synthetic: Antibody 7 LCDR2

<400> SEQUENCE: 71

Lys Ala Ser Thr Leu Glu Ser
1 5

<210> SEQ ID NO 72
<211> LENGTH: 9
<212> TYPE: PRT
<213> ORGANISM: Artificial Sequence
<220> FEATURE:
<223> OTHER INFORMATION: Synthetic: Antibody 7 LCDR3

<400> SEQUENCE: 72

Gln Gln Ser His His Pro Pro Trp Thr
1 5

<210> SEQ ID NO 73
<211> LENGTH: 125
<212> TYPE: PRT
<213> ORGANISM: Artificial Sequence
<220> FEATURE:
<223> OTHER INFORMATION: Synthetic: Antibody 7_GL VH

<400> SEQUENCE: 73

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln Pro Pro Gly Lys Gly Leu Glu
35 40 45

Trp Ile Gly Ser Ile Tyr Tyr Ser Gly Ser Thr Tyr Tyr Asn Pro Ser
50 55 60

Leu Lys Ser Arg Val Thr Ile Ser Gly Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Thr Pro Ala Tyr Phe Gly Gln Asp Arg Thr Asp Phe Phe
100 105 110

Asp Val Trp Gly Arg Gly Thr Leu Val Thr Val Ser Ser
115 120 125

<210> SEQ ID NO 74
<211> LENGTH: 7
<212> TYPE: PRT
<213> ORGANISM: Artificial Sequence
<220> FEATURE:
<223> OTHER INFORMATION: Synthetic: Antibody 7_GL HCDR1

<400> SEQUENCE: 74

Ser Gly Gly Tyr Tyr Trp Ser
1 5

<210> SEQ ID NO 75
<211> LENGTH: 16
<212> TYPE: PRT
<213> ORGANISM: Artificial Sequence
<220> FEATURE:
<223> OTHER INFORMATION: Synthetic: Antibody 7_GL HCDR2

<400> SEQUENCE: 75

```
Ser Ile Tyr Tyr Ser Gly Ser Thr Tyr Tyr Asn Pro Ser Leu Lys Ser
1               5                   10                  15
```

<210> SEQ ID NO 76
<211> LENGTH: 15
<212> TYPE: PRT
<213> ORGANISM: Artificial Sequence
<220> FEATURE:
<223> OTHER INFORMATION: Synthetic: Antibody 7_GL HCDR3

<400> SEQUENCE: 76

```
Thr Pro Ala Tyr Phe Gly Gln Asp Arg Thr Asp Phe Phe Asp Val
1               5                   10                  15
```

<210> SEQ ID NO 77
<211> LENGTH: 107
<212> TYPE: PRT
<213> ORGANISM: Artificial Sequence
<220> FEATURE:
<223> OTHER INFORMATION: Synthetic: Antibody 7_GL VL

<400> SEQUENCE: 77

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser His His Pro Pro Trp
                85                  90                  95

Thr Phe Gly Gln Gly Thr Lys Leu Glu Ile Lys
            100                 105
```

<210> SEQ ID NO 78
<211> LENGTH: 11
<212> TYPE: PRT
<213> ORGANISM: Artificial Sequence
<220> FEATURE:
<223> OTHER INFORMATION: Synthetic: Antibody 7_GL LCDR1

<400> SEQUENCE: 78

```
Arg Ala Ser Gln Gly Ile Ser Ser Trp Leu Ala
1               5                   10
```

<210> SEQ ID NO 79
<211> LENGTH: 7
<212> TYPE: PRT
<213> ORGANISM: Artificial Sequence
<220> FEATURE:
<223> OTHER INFORMATION: Synthetic: Antibody 7_GL LCDR2

<400> SEQUENCE: 79

Lys Ala Ser Thr Leu Glu Ser
1 5

<210> SEQ ID NO 80
<211> LENGTH: 9
<212> TYPE: PRT
<213> ORGANISM: Artificial Sequence
<220> FEATURE:
<223> OTHER INFORMATION: Synthetic: Antibody 7_GL LCDR3

<400> SEQUENCE: 80

Gln Gln Ser His His Pro Pro Trp Thr
1 5

<210> SEQ ID NO 81
<211> LENGTH: 125
<212> TYPE: PRT
<213> ORGANISM: Artificial Sequence
<220> FEATURE:
<223> OTHER INFORMATION: Synthetic: Antibody 8_GL VH

<400> SEQUENCE: 81

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ala Gly
20 25 30

Gly Tyr Tyr Trp Ser Trp Ile Arg Gln Pro Pro Gly Lys Gly Leu Glu
35 40 45

Trp Ile Gly Ser Leu Tyr Tyr Ser Gly Ser Thr Tyr Tyr Asn Pro Ser
50 55 60

Leu Lys Gly Arg Val Thr Ile Ser Gly Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Thr Pro Ala Tyr Phe Gly Gln Asp Arg Thr Asp Phe Phe
100 105 110

Asp Val Trp Gly Arg Gly Thr Leu Val Thr Val Ser Ser
115 120 125

<210> SEQ ID NO 82
<211> LENGTH: 7
<212> TYPE: PRT
<213> ORGANISM: Artificial Sequence
<220> FEATURE:
<223> OTHER INFORMATION: Synthetic: Antibody 8_GL HCDR1

<400> SEQUENCE: 82

Ala Gly Gly Tyr Tyr Trp Ser
1 5

<210> SEQ ID NO 83
<211> LENGTH: 16
<212> TYPE: PRT
<213> ORGANISM: Artificial Sequence
<220> FEATURE:
<223> OTHER INFORMATION: Synthetic: Antibody 8_GL HCDR2

<400> SEQUENCE: 83

Ser Leu Tyr Tyr Ser Gly Ser Thr Tyr Tyr Asn Pro Ser Leu Lys Gly
1 5 10 15

<210> SEQ ID NO 84
<211> LENGTH: 15
<212> TYPE: PRT
<213> ORGANISM: Artificial Sequence
<220> FEATURE:
<223> OTHER INFORMATION: Synthetic: Antibody 8_GL HCDR3

<400> SEQUENCE: 84

```
Thr Pro Ala Tyr Phe Gly Gln Asp Arg Thr Asp Phe Phe Asp Val
1               5                   10                  15
```

<210> SEQ ID NO 85
<211> LENGTH: 107
<212> TYPE: PRT
<213> ORGANISM: Artificial Sequence
<220> FEATURE:
<223> OTHER INFORMATION: Synthetic: Antibody 8_GL VL

<400> SEQUENCE: 85

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser His His Pro Pro Trp
                85                  90                  95

Thr Phe Gly Gln Gly Thr Lys Leu Glu Ile Lys
            100                 105
```

<210> SEQ ID NO 86
<211> LENGTH: 11
<212> TYPE: PRT
<213> ORGANISM: Artificial Sequence
<220> FEATURE:
<223> OTHER INFORMATION: Synthetic: Antibody 8_GL LCDR1

<400> SEQUENCE: 86

```
Arg Ala Ser Gln Gly Ile Ser Ser Trp Leu Ala
1               5                   10
```

<210> SEQ ID NO 87
<211> LENGTH: 7
<212> TYPE: PRT
<213> ORGANISM: Artificial Sequence
<220> FEATURE:
<223> OTHER INFORMATION: Synthetic: Antibody 8_GL LCDR2

<400> SEQUENCE: 87

```
Lys Ala Ser Thr Leu Glu Ser
1               5
```

<210> SEQ ID NO 88
<211> LENGTH: 9
<212> TYPE: PRT
<213> ORGANISM: Artificial Sequence
<220> FEATURE:
<223> OTHER INFORMATION: Synthetic: Antibody 8_GL LCDR3

<400> SEQUENCE: 88

Gln Gln Ser His His Pro Pro Trp Thr
1 5

<210> SEQ ID NO 89
<211> LENGTH: 125
<212> TYPE: PRT
<213> ORGANISM: Artificial Sequence
<220> FEATURE:
<223> OTHER INFORMATION: Synthetic: Antibody 9 VH

<400> SEQUENCE: 89

Gln Val Gln Leu Gln Gln Ser Gly Pro Arg Leu Val Glu Pro Ser Gln
1 5 10 15

Thr Leu Ser Leu Thr Cys Thr Val Ser Gly Gly Ser Ile Ser Ser Asp
20 25 30

Gly Tyr Tyr Trp Ser Trp Ile Arg Gln Pro Ala Gly Lys Gly Leu Glu
35 40 45

Trp Ile Gly Ser Ile Tyr Tyr Ser Gly Ser Thr Tyr Tyr Asn Pro Ser
50 55 60

Leu Lys Ser Arg Val Thr Ile Ser Gly Asp Thr Pro Lys Asn Gln Phe
65 70 75 80

Ser Leu Lys Leu Ser Ser Val Thr Ala Ala Asp Thr Ala Val Tyr Tyr
85 90 95

Cys Ala Arg Thr Pro Ala Tyr Phe Gly Gln Asp Arg Thr Asp Phe Phe
100 105 110

Asp Val Trp Gly Arg Gly Thr Leu Val Thr Val Ser Ser
115 120 125

<210> SEQ ID NO 90
<211> LENGTH: 7
<212> TYPE: PRT
<213> ORGANISM: Artificial Sequence
<220> FEATURE:
<223> OTHER INFORMATION: Synthetic: Antibody 9 HCDR1

<400> SEQUENCE: 90

Ser Asp Gly Tyr Tyr Trp Ser
1 5

<210> SEQ ID NO 91
<211> LENGTH: 16
<212> TYPE: PRT
<213> ORGANISM: Artificial Sequence
<220> FEATURE:
<223> OTHER INFORMATION: Synthetic: Antibody 9 HCDR2

<400> SEQUENCE: 91

Ser Ile Tyr Tyr Ser Gly Ser Thr Tyr Tyr Asn Pro Ser Leu Lys Ser
1 5 10 15

<210> SEQ ID NO 92
<211> LENGTH: 15
<212> TYPE: PRT
<213> ORGANISM: Artificial Sequence
<220> FEATURE:
<223> OTHER INFORMATION: Synthetic: Antibody 9 HCDR3

<400> SEQUENCE: 92

Thr Pro Ala Tyr Phe Gly Gln Asp Arg Thr Asp Phe Phe Asp Val
1 5 10 15

```
<210> SEQ ID NO 93
<211> LENGTH: 107
<212> TYPE: PRT
<213> ORGANISM: Artificial Sequence
<220> FEATURE:
<223> OTHER INFORMATION: Synthetic: Antibody 9 VL

<400> SEQUENCE: 93

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His His Pro Pro Trp
                85                  90                  95

Thr Phe Gly Gln Gly Thr Lys Leu Glu Ile Lys
            100                 105


<210> SEQ ID NO 94
<211> LENGTH: 11
<212> TYPE: PRT
<213> ORGANISM: Artificial Sequence
<220> FEATURE:
<223> OTHER INFORMATION: Synthetic: Antibody 9 LCDR1

<400> SEQUENCE: 94

Arg Ala Ser Gln Gly Ile Ser Ser Trp Leu Ala
1               5                   10


<210> SEQ ID NO 95
<211> LENGTH: 7
<212> TYPE: PRT
<213> ORGANISM: Artificial Sequence
<220> FEATURE:
<223> OTHER INFORMATION: Synthetic: Antibody 9 LCDR2

<400> SEQUENCE: 95

Lys Ala Ser Thr Leu Glu Ser
1               5


<210> SEQ ID NO 96
<211> LENGTH: 9
<212> TYPE: PRT
<213> ORGANISM: Artificial Sequence
<220> FEATURE:
<223> OTHER INFORMATION: Synthetic: Antibody 9 LCDR3

<400> SEQUENCE: 96

Gln Gln Ser His His Pro Pro Trp Thr
1               5


<210> SEQ ID NO 97
<211> LENGTH: 125
<212> TYPE: PRT
<213> ORGANISM: Artificial Sequence
<220> FEATURE:
<223> OTHER INFORMATION: Synthetic: Antibody 10 VH
```

<400> SEQUENCE: 97

Gln Val Gln Leu Gln Gln Ser Gly Pro Arg Leu Val Glu Pro Ser Gln
1 5 10 15

Thr Leu Ser Leu Thr Cys Thr Val Ser Gly Gly Ser Ile Ser Ser Asp
20 25 30

Gly Tyr Tyr Trp Ser Trp Ile Arg Gln Pro Ala Gly Lys Gly Leu Glu
35 40 45

Trp Ile Gly Ser Ile Tyr Tyr Ser Gly Ser Thr Tyr Tyr Asn Pro Ser
50 55 60

Leu Arg Ser Arg Val Thr Ile Ser Gly Asp Thr Pro Lys Asn Gln Phe
65 70 75 80

Ser Leu Lys Leu Ser Ser Val Thr Ala Ala Asp Thr Ala Val Tyr Tyr
85 90 95

Cys Ala Arg Thr Pro Ala Tyr Phe Gly Gln Asp Arg Thr Asp Phe Phe
100 105 110

Asp Val Trp Gly Arg Gly Thr Leu Val Thr Val Ser Ser
115 120 125

<210> SEQ ID NO 98
<211> LENGTH: 7
<212> TYPE: PRT
<213> ORGANISM: Artificial Sequence
<220> FEATURE:
<223> OTHER INFORMATION: Synthetic: Antibody 10 HCDR1

<400> SEQUENCE: 98

Ser Asp Gly Tyr Tyr Trp Ser
1 5

<210> SEQ ID NO 99
<211> LENGTH: 16
<212> TYPE: PRT
<213> ORGANISM: Artificial Sequence
<220> FEATURE:
<223> OTHER INFORMATION: Synthetic: Antibody 10 HCDR2

<400> SEQUENCE: 99

Ser Ile Tyr Tyr Ser Gly Ser Thr Tyr Tyr Asn Pro Ser Leu Arg Ser
1 5 10 15

<210> SEQ ID NO 100
<211> LENGTH: 15
<212> TYPE: PRT
<213> ORGANISM: Artificial Sequence
<220> FEATURE:
<223> OTHER INFORMATION: Synthetic: Antibody 10 HCDR3

<400> SEQUENCE: 100

Thr Pro Ala Tyr Phe Gly Gln Asp Arg Thr Asp Phe Phe Asp Val
1 5 10 15

<210> SEQ ID NO 101
<211> LENGTH: 107
<212> TYPE: PRT
<213> ORGANISM: Artificial Sequence
<220> FEATURE:
<223> OTHER INFORMATION: Synthetic: Antibody 10 VL

<400> SEQUENCE: 101

Asp Ile Val Met Thr Gln Ser Pro Ser Thr Leu Ser Ala Ser Val Gly
1 5 10 15

```
Asp Arg Val Thr Ile Thr Cys Arg Ala Ser Gln Gly Ile Ser Ser Trp
            20                  25                  30

Leu Ala Trp Tyr Gln Gln Lys Pro Gly Gly Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His His Pro Pro Trp
                85                  90                  95

Thr Phe Ser Gln Gly Thr Lys Leu Glu Ile Lys
            100                 105


<210> SEQ ID NO 102
<211> LENGTH: 11
<212> TYPE: PRT
<213> ORGANISM: Artificial Sequence
<220> FEATURE:
<223> OTHER INFORMATION: Synthetic: Antibody 10 LCDR1

<400> SEQUENCE: 102

Arg Ala Ser Gln Gly Ile Ser Ser Trp Leu Ala
1               5                   10


<210> SEQ ID NO 103
<211> LENGTH: 7
<212> TYPE: PRT
<213> ORGANISM: Artificial Sequence
<220> FEATURE:
<223> OTHER INFORMATION: Synthetic: Antibody 10 LCDR2

<400> SEQUENCE: 103

Lys Ala Ser Thr Leu Glu Ser
1               5


<210> SEQ ID NO 104
<211> LENGTH: 9
<212> TYPE: PRT
<213> ORGANISM: Artificial Sequence
<220> FEATURE:
<223> OTHER INFORMATION: Synthetic: Antibody 10 LCDR3

<400> SEQUENCE: 104

Gln Gln Ser His His Pro Pro Trp Thr
1               5


<210> SEQ ID NO 105
<211> LENGTH: 125
<212> TYPE: PRT
<213> ORGANISM: Artificial Sequence
<220> FEATURE:
<223> OTHER INFORMATION: Synthetic: Antibody 11 VH

<400> SEQUENCE: 105

Gln Val Gln Leu Gln Gln Ser Gly Pro Arg Leu Val Glu Pro Ser Gln
1               5                   10                  15

Thr Leu Ser Leu Thr Cys Thr Val Ser Gly Gly Ser Ile Ser Ala Asp
            20                  25                  30

Gly Tyr Tyr Trp Ser Trp Ile Arg Gln Pro Ala Gly Lys Gly Leu Glu
        35                  40                  45

Trp Ile Gly Ser Leu Tyr Tyr Ser Gly Ser Thr Tyr Tyr Asn Pro Ser
    50                  55                  60
```

```
Leu Arg Gly Arg Val Thr Ile Ser Gly Asp Thr Pro Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
        115                 120                 125


<210> SEQ ID NO 106
<211> LENGTH: 7
<212> TYPE: PRT
<213> ORGANISM: Artificial Sequence
<220> FEATURE:
<223> OTHER INFORMATION: Synthetic: Antibody 11 HCDR1

<400> SEQUENCE: 106

Ala Asp Gly Tyr Tyr Trp Ser
1               5


<210> SEQ ID NO 107
<211> LENGTH: 16
<212> TYPE: PRT
<213> ORGANISM: Artificial Sequence
<220> FEATURE:
<223> OTHER INFORMATION: Synthetic: Antibody 11 HCDR2

<400> SEQUENCE: 107

Ser Leu Tyr Tyr Ser Gly Ser Thr Tyr Tyr Asn Pro Ser Leu Arg Gly
1               5                   10                  15


<210> SEQ ID NO 108
<211> LENGTH: 15
<212> TYPE: PRT
<213> ORGANISM: Artificial Sequence
<220> FEATURE:
<223> OTHER INFORMATION: Synthetic: Antibody 11 HCDR3

<400> SEQUENCE: 108

Thr Pro Ala Tyr Phe Gly Gln Asp Arg Thr Asp Phe Phe Asp Val
1               5                   10                  15


<210> SEQ ID NO 109
<211> LENGTH: 107
<212> TYPE: PRT
<213> ORGANISM: Artificial Sequence
<220> FEATURE:
<223> OTHER INFORMATION: Synthetic: Antibody 11 VL

<400> SEQUENCE: 109

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Gly Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His His Pro Pro Trp
                85                  90                  95
```

Thr Phe Ser Gln Gly Thr Lys Leu Glu Ile Lys
100 105

<210> SEQ ID NO 110
<211> LENGTH: 11
<212> TYPE: PRT
<213> ORGANISM: Artificial Sequence
<220> FEATURE:
<223> OTHER INFORMATION: Synthetic: Antibody 11 LCDR1

<400> SEQUENCE: 110

Arg Ala Ser Gln Gly Ile Ser Ser Trp Leu Ala
1 5 10

<210> SEQ ID NO 111
<211> LENGTH: 7
<212> TYPE: PRT
<213> ORGANISM: Artificial Sequence
<220> FEATURE:
<223> OTHER INFORMATION: Synthetic: Antibody 11 LCDR2

<400> SEQUENCE: 111

Lys Ala Ser Thr Leu Glu Ser
1 5

<210> SEQ ID NO 112
<211> LENGTH: 9
<212> TYPE: PRT
<213> ORGANISM: Artificial Sequence
<220> FEATURE:
<223> OTHER INFORMATION: Synthetic: Antibody 11 LCDR3

<400> SEQUENCE: 112

Gln Gln Ser His His Pro Pro Trp Thr
1 5

<210> SEQ ID NO 113
<211> LENGTH: 125
<212> TYPE: PRT
<213> ORGANISM: Artificial Sequence
<220> FEATURE:
<223> OTHER INFORMATION: Synthetic: Antibody 11_GL VH

<400> SEQUENCE: 113

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ala Asp
20 25 30

Gly Tyr Tyr Trp Ser Trp Ile Arg Gln Pro Pro Gly Lys Gly Leu Glu
35 40 45

Trp Ile Gly Ser Leu Tyr Tyr Ser Gly Ser Thr Tyr Tyr Asn Pro Ser
50 55 60

Leu Arg Gly Arg Val Thr Ile Ser Gly Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Thr Pro Ala Tyr Phe Gly Gln Asp Arg Thr Asp Phe Phe
100 105 110

Asp Val Trp Gly Arg Gly Thr Leu Val Thr Val Ser Ser
115 120 125

<210> SEQ ID NO 114
<211> LENGTH: 7

<212> TYPE: PRT
<213> ORGANISM: Artificial Sequence
<220> FEATURE:
<223> OTHER INFORMATION: Synthetic: Antibody 11_GL HCDR1

<400> SEQUENCE: 114

Ala Asp Gly Tyr Tyr Trp Ser
1 5

<210> SEQ ID NO 115
<211> LENGTH: 16
<212> TYPE: PRT
<213> ORGANISM: Artificial Sequence
<220> FEATURE:
<223> OTHER INFORMATION: Synthetic: Antibody 11_GL HCDR2

<400> SEQUENCE: 115

Ser Leu Tyr Tyr Ser Gly Ser Thr Tyr Tyr Asn Pro Ser Leu Arg Gly
1 5 10 15

<210> SEQ ID NO 116
<211> LENGTH: 15
<212> TYPE: PRT
<213> ORGANISM: Artificial Sequence
<220> FEATURE:
<223> OTHER INFORMATION: Synthetic: Antibody 11_GL HCDR3

<400> SEQUENCE: 116

Thr Pro Ala Tyr Phe Gly Gln Asp Arg Thr Asp Phe Phe Asp Val
1 5 10 15

<210> SEQ ID NO 117
<211> LENGTH: 107
<212> TYPE: PRT
<213> ORGANISM: Artificial Sequence
<220> FEATURE:
<223> OTHER INFORMATION: Synthetic: Antibody 11_GL VL

<400> SEQUENCE: 117

Asp Ile Gln Met Thr Gln Ser Pro Ser Thr Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Val Leu Ile
35 40 45

Tyr Lys Ala Ser Thr Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Ser His His Pro Pro Trp
85 90 95

Thr Phe Gly Gln Gly Thr Lys Leu Glu Ile Lys
100 105

<210> SEQ ID NO 118
<211> LENGTH: 11
<212> TYPE: PRT
<213> ORGANISM: Artificial Sequence
<220> FEATURE:
<223> OTHER INFORMATION: Synthetic: Antibody 11_GL LCDR1

<400> SEQUENCE: 118

Arg Ala Ser Gln Gly Ile Ser Ser Trp Leu Ala
1 5 10

<210> SEQ ID NO 119
<211> LENGTH: 7
<212> TYPE: PRT
<213> ORGANISM: Artificial Sequence
<220> FEATURE:
<223> OTHER INFORMATION: Synthetic: Antibody 11_GL LCDR2

<400> SEQUENCE: 119

```
Lys Ala Ser Thr Leu Glu Ser
1               5
```

<210> SEQ ID NO 120
<211> LENGTH: 9
<212> TYPE: PRT
<213> ORGANISM: Artificial Sequence
<220> FEATURE:
<223> OTHER INFORMATION: Synthetic: Antibody 11_GL LCDR3

<400> SEQUENCE: 120

```
Gln Gln Ser His His Pro Pro Trp Thr
1               5
```

<210> SEQ ID NO 121
<211> LENGTH: 125
<212> TYPE: PRT
<213> ORGANISM: Artificial Sequence
<220> FEATURE:
<223> OTHER INFORMATION: Synthetic: Antibody 12_GL VH

<400> SEQUENCE: 121

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ala Asp
            20                  25                  30

Gly Tyr Tyr Trp Ser Trp Ile Arg Gln Pro Pro Gly Lys Gly Leu Glu
        35                  40                  45

Trp Ile Gly Ser Leu Tyr Tyr Ser Gly Ser Thr Tyr Tyr Asn Pro Ser
    50                  55                  60

Leu Lys Gly Arg Val Thr Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
        115                 120                 125
```

<210> SEQ ID NO 122
<211> LENGTH: 7
<212> TYPE: PRT
<213> ORGANISM: Artificial Sequence
<220> FEATURE:
<223> OTHER INFORMATION: Synthetic: Antibody 12_GL HCDR1

<400> SEQUENCE: 122

```
Ala Asp Gly Tyr Tyr Trp Ser
1               5
```

<210> SEQ ID NO 123
<211> LENGTH: 16
<212> TYPE: PRT
<213> ORGANISM: Artificial Sequence
<220> FEATURE:
<223> OTHER INFORMATION: Synthetic: Antibody 12_GL HCDR2

<400> SEQUENCE: 123

Ser Leu Tyr Tyr Ser Gly Ser Thr Tyr Tyr Asn Pro Ser Leu Lys Gly
1 5 10 15

<210> SEQ ID NO 124
<211> LENGTH: 15
<212> TYPE: PRT
<213> ORGANISM: Artificial Sequence
<220> FEATURE:
<223> OTHER INFORMATION: Synthetic: Antibody 12_GL HCDR3

<400> SEQUENCE: 124

Thr Pro Ala Tyr Phe Gly Gln Asp Arg Thr Asp Phe Phe Asp Val
1 5 10 15

<210> SEQ ID NO 125
<211> LENGTH: 107
<212> TYPE: PRT
<213> ORGANISM: Artificial Sequence
<220> FEATURE:
<223> OTHER INFORMATION: Synthetic: Antibody 12_GL VL

<400> SEQUENCE: 125

Asp Ile Gln Met Thr Gln Ser Pro Ser Thr Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Val Leu Ile
35 40 45

Tyr Lys Ala Ser Thr Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Ser His His Pro Pro Trp
85 90 95

Thr Phe Gly Gln Gly Thr Lys Leu Glu Ile Lys
100 105

<210> SEQ ID NO 126
<211> LENGTH: 11
<212> TYPE: PRT
<213> ORGANISM: Artificial Sequence
<220> FEATURE:
<223> OTHER INFORMATION: Synthetic: Antibody 12_GL LCDR1

<400> SEQUENCE: 126

Arg Ala Ser Gln Gly Ile Ser Ser Trp Leu Ala
1 5 10

<210> SEQ ID NO 127
<211> LENGTH: 7
<212> TYPE: PRT
<213> ORGANISM: Artificial Sequence
<220> FEATURE:
<223> OTHER INFORMATION: Synthetic: Antibody 12_GL LCDR2

<400> SEQUENCE: 127

Lys Ala Ser Thr Leu Glu Ser
1 5

<210> SEQ ID NO 128
<211> LENGTH: 9
<212> TYPE: PRT
<213> ORGANISM: Artificial Sequence
<220> FEATURE:
<223> OTHER INFORMATION: Synthetic: Antibody 12_GL LCDR3

<400> SEQUENCE: 128

Gln Gln Ser His His Pro Pro Trp Thr
1 5

<210> SEQ ID NO 129
<211> LENGTH: 5
<212> TYPE: PRT
<213> ORGANISM: Artificial Sequence
<220> FEATURE:
<223> OTHER INFORMATION: Synthetic: HCDR1

<400> SEQUENCE: 129

Gly Tyr Tyr Phe His
1 5

<210> SEQ ID NO 130
<211> LENGTH: 17
<212> TYPE: PRT
<213> ORGANISM: Artificial Sequence
<220> FEATURE:
<223> OTHER INFORMATION: Synthetic: HCDR2

<400> SEQUENCE: 130

Arg Ile Asp Pro Glu Asp Asp Ser Thr Lys Tyr Ala Glu Arg Phe Lys
1 5 10 15

Asp

<210> SEQ ID NO 131
<211> LENGTH: 17
<212> TYPE: PRT
<213> ORGANISM: Artificial Sequence
<220> FEATURE:
<223> OTHER INFORMATION: Synthetic: HCDR3

<400> SEQUENCE: 131

Trp Arg Ile Tyr Arg Asp Ser Ser Gly Arg Pro Phe Tyr Val Met Asp
1 5 10 15

Ala

<210> SEQ ID NO 132
<211> LENGTH: 11
<212> TYPE: PRT
<213> ORGANISM: Artificial Sequence
<220> FEATURE:
<223> OTHER INFORMATION: Synthetic: LCDR1

<400> SEQUENCE: 132

Leu Ala Ser Glu Asp Ile Tyr Thr Tyr Leu Thr
1 5 10

<210> SEQ ID NO 133
<211> LENGTH: 7
<212> TYPE: PRT
<213> ORGANISM: Artificial Sequence
<220> FEATURE:
<223> OTHER INFORMATION: Synthetic: LCDR2

<400> SEQUENCE: 133

```
Gly Ala Asn Lys Leu Gln Asp
1               5
```

<210> SEQ ID NO 134
<211> LENGTH: 9
<212> TYPE: PRT
<213> ORGANISM: Artificial Sequence
<220> FEATURE:
<223> OTHER INFORMATION: Synthetic: LCDR3

<400> SEQUENCE: 134

```
Leu Gln Gly Ser Lys Phe Pro Leu Thr
1               5
```

<210> SEQ ID NO 135
<211> LENGTH: 193
<212> TYPE: PRT
<213> ORGANISM: Homo sapiens
<220> FEATURE:
<221> NAME/KEY: misc_feature
<223> OTHER INFORMATION: Human IL-18

<400> SEQUENCE: 135

```
Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp
```

<210> SEQ ID NO 136
<211> LENGTH: 582
<212> TYPE: DNA
<213> ORGANISM: Homo sapiens
<220> FEATURE:
<221> NAME/KEY: misc_feature
<223> OTHER INFORMATION: Human IL-18 (PN)

<400> SEQUENCE: 136

```
atggctgctg aaccagtaga agacaattgc atcaactttg tggcaatgaa atttattgac     60

aatacgcttt actttatagc tgaagatgat gaaaacctgg aatcagatta ctttggcaag    120

cttgaatcta aattatcagt cataagaaat ttgaatgacc aagttctctt cattgaccaa    180

ggaaatcggc ctctatttga agatatgact gattctgact gtagagataa tgcaccccgg    240

accatattta ttataagtat gtataaagat agccagccta gaggtatggc tgtaactatc    300

tctgtgaagt gtgagaaaat ttcaactctc tcctgtgaga acaaaattat ttcctttaag    360

gaaatgaatc ctcctgataa catcaaggat acaaaaagtg acatcatatt ctttcagaga    420

agtgtcccag gacatgataa taagatgcaa tttgaatctt catcatacga aggatacttt    480

ctagcttgtg aaaaagagag agaccttttt aaactcattt tgaaaaaaga ggatgaattg    540

ggggatagat ctataatgtt cactgttcaa aacgaagact ag                       582
```

<210> SEQ ID NO 137
<211> LENGTH: 456
<212> TYPE: PRT
<213> ORGANISM: Artificial Sequence
<220> FEATURE:
<223> OTHER INFORMATION: Synthetic: H1 heavy chain

<400> SEQUENCE: 137

```
Gln Val Gln Leu Val Gln Ser Gly Ala Glu Val Lys Lys Pro Gly Ala
1               5                   10                  15

Ser Val Lys Val Ser Cys Lys Val Ser Gly Glu Ile Ser Thr Gly Tyr
            20                  25                  30

Tyr Phe His Trp Val Arg Gln Ala Pro Gly Lys Gly Leu Glu Trp Met
        35                  40                  45

Gly Arg Ile Asp Pro Glu Asp Asp Ser Thr Lys Tyr Ala Glu Arg Phe
    50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Thr Trp Arg Ile Tyr Arg Asp Ser Ser Gly Arg Pro Phe Tyr Val
            100                 105                 110

Met Asp Ala Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240
```

```
Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

<210> SEQ ID NO 138
<211> LENGTH: 1370
<212> TYPE: DNA
<213> ORGANISM: Artificial Sequence
<220> FEATURE:
<223> OTHER INFORMATION: Synthetic: H1 heavy chain (PN)

<400> SEQUENCE: 138

```
aggtgcagct ggtgcagagc ggagccgagg tgaagaagcc tggcgccagc gtcaaggtgt     60

cctgtaaggt gtccggcgag atcagcaccg gctactactt ccactgggtg aggcaggccc    120

ctggcaaggg cctggagtgg atgggcagaa tcgaccccga ggacgacagc accaagtacg    180

ccgagcggtt caaggacagg gtgaccatga ccgaggacac cagcaccgat accgcctaca    240

tggagctgtc cagcctgaga agcgaggata ccgccgtgta ctactgtacc acctggcgga    300

tctacagaga cagcagcggc agacccttct acgtgatgga tgcctggggc cagggcacac    360

tagtgaccgt gtccagcgcc agcaccaagg gccccagcgt gttccccctg gcccccagca    420

gcaagagcac cagcggcggc acagccgccc tgggctgcct ggtgaaggac tacttccccg    480

aaccggtgac cgtgtcctgg aacagcggag ccctgaccag cggcgtgcac accttccccg    540

ccgtgctgca gagcagcggc ctgtacagcc tgagcagcgt ggtgaccgtg cccagcagca    600

gcctgggcac ccagacctac atctgtaacg tgaaccacaa gcccagcaac accaaggtgg    660

acaagaaggt ggagcccaag agctgtgaca agacccacac ctgccccccc tgccctgccc    720

ccgagctgct gggaggcccc agcgtgttcc tgttcccccc caagcctaag gacaccctga    780
```

tgatcagcag aacccccgag gtgacctgtg tggtggtgga tgtgagccac gaggaccctg 840
aggtgaagtt caactggtac gtggacggcg tggaggtgca caatgccaag accaagccca 900
gggaggagca gtacaacagc acctaccggg tggtgtccgt gctgaccgtg ctgcaccagg 960
attggctgaa cggcaaggag tacaagtgta aggtgtccaa caaggccctg cctgccccta 1020
tcgagaaaac catcagcaag gccaagggcc agcccagaga gccccaggtg tacaccctgc 1080
cccctagcag agatgagctg accaagaacc aggtgtccct gacctgcctg gtgaagggct 1140
tctaccccag cgacatcgcc gtggagtggg agagcaacgg ccagcccgag aacaactaca 1200
agaccacccc ccctgtgctg gacagcgatg gcagcttctt cctgtacagc aagctgaccg 1260
tggacaagag cagatggcag cagggcaacg tgttcagctg ctccgtgatg cacgaggccc 1320
tgcacaatca ctacacccag aagagcctga gcctgtcccc tggcaagtga 1370

<210> SEQ ID NO 139
<211> LENGTH: 126
<212> TYPE: PRT
<213> ORGANISM: Artificial Sequence
<220> FEATURE:
<223> OTHER INFORMATION: Synthetic: H1 variable region

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Val Ser Gly Glu Ile Ser Thr Gly Tyr
            20                  25                  30

Tyr Phe His Trp Val Arg Gln Ala Pro Gly Lys Gly Leu Glu Trp Met
        35                  40                  45

Gly Arg Ile Asp Pro Glu Asp Asp Ser Thr Lys Tyr Ala Glu Arg Phe
    50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Thr Trp Arg Ile Tyr Arg Asp Ser Ser Gly Arg Pro Phe Tyr Val
            100                 105                 110

Met Asp Ala Trp Gly Gln Gly Thr Leu Val Thr Val Ser Ser
        115                 120                 125

<210> SEQ ID NO 140
<211> LENGTH: 378
<212> TYPE: DNA
<213> ORGANISM: Artificial Sequence
<220> FEATURE:
<223> OTHER INFORMATION: Synthetic: H1 variable region (PN)

<400> SEQUENCE: 140
caggtgcagc tggtgcagag cggagccgag gtgaagaagc ctggcgccag cgtcaaggtg 60
tcctgtaagg tgtccggcga gatcagcacc ggctactact tccactgggt gaggcaggcc 120
cctggcaagg gcctggagtg gatgggcaga atcgaccccg aggacgacag caccaagtac 180
gccgagcggt tcaaggacag ggtgaccatg accgaggaca ccagcaccga taccgcctac 240
atggagctgt ccagcctgag aagcgaggat accgccgtgt actactgtac cacctggcgg 300
atctacagag acagcagcgg cagacccttc tacgtgatgg atgcctgggg ccagggcaca 360
ctagtgaccg tgtccagc 378

<210> SEQ ID NO 141
<211> LENGTH: 214
<212> TYPE: PRT
<213> ORGANISM: Artificial Sequence
<220> FEATURE:
<223> OTHER INFORMATION: Synthetic: L2 light chain

<400> SEQUENCE: 141

```
Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Tyr Thr Tyr
            20                  25                  30

Leu Thr Trp Tyr Gln Gln Lys Pro Gly Lys Ala Pro Lys Leu Leu Ile
        35                  40                  45

Tyr Gly Ala Asn Lys Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Gly Ser Lys Phe Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 142
<211> LENGTH: 642
<212> TYPE: DNA
<213> ORGANISM: Artificial Sequence
<220> FEATURE:
<223> OTHER INFORMATION: Synthetic: L2 light chain (PN)

<400> SEQUENCE: 142

```
gatatccaga tgacccagtc ccccagcagc gtgtccgcct ctgtgggcga tagagtgacc     60

atcacctgcc tggccagcga ggacatctac acctacctga cctggtatca gcagaagcct    120

ggcaaggccc ctaagctgct gatctacggc gccaacaagc tgcaggacgg cgtgcccagc    180

agattcagcg gcagcggctc cggcaccgac tacaccctga ccatcagcag cctgcagcct    240

gaggatttcg ccacctacta ctgcctgcag ggcagcaagt tcccccctgac cttcggccag    300

ggcaccaagc tggagatcaa gcgtacggtg gccgccccca gcgtgttcat cttccccccc    360

agcgatgagc agctgaagag cggcaccgcc agcgtggtgt gtctgctgaa caacttctac    420

ccccgggagg ccaaggtgca gtggaaggtg gacaatgccc tgcagagcgg caacagccag    480

gagagcgtga ccgagcagga cagcaaggac tccacctaca gcctgagcag caccctgacc    540
```

ctgagcaagg ccgactacga gaagcacaag gtgtacgcct gtgaggtgac ccaccagggc 600
ctgtccagcc ccgtgaccaa gagcttcaac cggggcgagt gc 642

<210> SEQ ID NO 143
<211> LENGTH: 107
<212> TYPE: PRT
<213> ORGANISM: Artificial Sequence
<220> FEATURE:
<223> OTHER INFORMATION: Synthetic: L2 variable region

<400> SEQUENCE: 143

Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Tyr Thr Tyr
            20                  25                  30

Leu Thr Trp Tyr Gln Gln Lys Pro Gly Lys Ala Pro Lys Leu Leu Ile
        35                  40                  45

Tyr Gly Ala Asn Lys Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Gly Ser Lys Phe Pro Leu
                85                  90                  95

Thr Phe Gly Gln Gly Thr Lys Leu Glu Ile Lys
            100                 105

<210> SEQ ID NO 144
<211> LENGTH: 321
<212> TYPE: DNA
<213> ORGANISM: Artificial Sequence
<220> FEATURE:
<223> OTHER INFORMATION: Synthetic: L2 variable region (PN)

<400> SEQUENCE: 144
gatatccaga tgacccagtc ccccagcagc gtgtccgcct ctgtgggcga tagagtgacc 60
atcacctgcc tggccagcga ggacatctac acctacctga cctggtatca gcagaagcct 120
ggcaaggccc ctaagctgct gatctacggc gccaacaagc tgcaggacgg cgtgcccagc 180
agattcagcg gcagcggctc cggcaccgac tacaccctga ccatcagcag cctgcagcct 240
gaggatttcg ccacctacta ctgcctgcag ggcagcaagt tcccctgac cttcggccag 300 ggcaccaagc tggagatcaa g 321

<210> SEQ ID NO 145
<211> LENGTH: 456
<212> TYPE: PRT
<213> ORGANISM: Artificial Sequence
<220> FEATURE:
<223> OTHER INFORMATION: Synthetic: H2 heavy chain

<400> SEQUENCE: 145

Gln Val Gln Leu Val Gln Ser Gly Ala Glu Val Lys Lys Pro Gly Ala
1               5                   10                  15

Ser Val Lys Val Ser Cys Lys Val Ser Gly Glu Ile Ser Thr Gly Tyr
            20                  25                  30

Tyr Phe His Trp Val Arg Arg Arg Pro Gly Lys Gly Leu Glu Trp Met
        35                  40                  45

Gly Arg Ile Asp Pro Glu Asp Asp Ser Thr Lys Tyr Ala Glu Arg Phe
    50                  55                  60

```
Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Thr Trp Arg Ile Tyr Arg Asp Ser Ser Gly Arg Pro Phe Tyr Val
            100                 105                 110

Met Asp Ala Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

<210> SEQ ID NO 146
<211> LENGTH: 1368
<212> TYPE: DNA

<213> ORGANISM: Artificial Sequence
<220> FEATURE:
<223> OTHER INFORMATION: Synthetic: H2 heavy chain (PN)

<400> SEQUENCE: 146

```
caggtccagc tggtacagtc tggggctgag gtgaagaagc ctggggcctc agtgaaggtc     60

tcctgcaagg tttccggaga aataagtact ggatactatt tccactgggt gcgacgaagg    120

cctggaaaag ggcttgagtg gatgggaagg attgatcctg aggatgatag tactaaatat    180

gctgagaggt tcaaagacag agtcaccatg accgaggaca catctacaga cacagcctac    240

atggagctga gcagcctgag atctgaggac acggccgtgt attactgtac cacatggcgg    300

atataccgag atagttctgg ccgccccttc tatgttatgg atgcctgggg ccaagggaca    360

ctagtcacag tctcctcagc ctccaccaag ggcccatcgg tcttccccct ggcaccctcc    420

tccaagagca cctctggggg cacagcggcc ctgggctgcc tggtcaagga ctacttcccc    480

gaaccggtga cggtgtcgtg gaactcaggc gccctgacca gcggcgtgca caccttcccg    540

gctgtcctac agtcctcagg actctactcc ctcagcagcg tggtgaccgt gccctccagc    600

agcttgggca cccagaccta catctgcaac gtgaatcaca agcccagcaa caccaaggtg    660

gacaagaaag ttgagcccaa atcttgtgac aaaactcaca catgcccacc gtgcccagca    720

cctgaactcc tggggggacc gtcagtcttc ctcttccccc caaaacccaa ggacaccctc    780

atgatctccc ggacccctga ggtcacatgc gtggtggtgg acgtgagcca cgaagaccct    840

gaggtcaagt tcaactggta cgtggacggc gtggaggtgc ataatgccaa gacaaagccg    900

cgggaggagc agtacaacag cacgtaccgt gtggtcagcg tcctcaccgt cctgcaccag    960

gactggctga atggcaagga gtacaagtgc aaggtctcca acaaagccct cccagccccc   1020

atcgagaaaa ccatctccaa agccaaaggg cagccccgag aaccacaggt gtacaccctg   1080

cccccatccc gggatgagct gaccaagaac caggtcagcc tgacctgcct ggtcaaaggc   1140

ttctatccca gcgacatcgc cgtggagtgg gagagcaatg ggcagccgga gaacaactac   1200

aagaccacgc ctcccgtgct ggactccgac ggctccttct tcctctacag caagctcacc   1260

gtggacaaga gcaggtggca gcaggggaac gtcttctcat gctccgtgat gcatgaggct   1320

ctgcacaacc actacacgca gaagagcctc tccctgtctc cgggtaaa                1368
```

<210> SEQ ID NO 147
<211> LENGTH: 126
<212> TYPE: PRT
<213> ORGANISM: Artificial Sequence
<220> FEATURE:
<223> OTHER INFORMATION: Synthetic: H2 variable region

<400> SEQUENCE: 147

```
Gln Val Gln Leu Val Gln Ser Gly Ala Glu Val Lys Lys Pro Gly Ala
1               5                   10                  15

Ser Val Lys Val Ser Cys Lys Val Ser Gly Glu Ile Ser Thr Gly Tyr
            20                  25                  30

Tyr Phe His Trp Val Arg Arg Arg Pro Gly Lys Gly Leu Glu Trp Met
        35                  40                  45

Gly Arg Ile Asp Pro Glu Asp Asp Ser Thr Lys Tyr Ala Glu Arg Phe
    50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95
```

```
Thr Thr Trp Arg Ile Tyr Arg Asp Ser Ser Gly Arg Pro Phe Tyr Val
            100                 105                 110

Met Asp Ala Trp Gly Gln Gly Thr Leu Val Thr Val Ser Ser
        115                 120                 125


<210> SEQ ID NO 148
<211> LENGTH: 378
<212> TYPE: DNA
<213> ORGANISM: Artificial Sequence
<220> FEATURE:
<223> OTHER INFORMATION: Synthetic: H2 variable region (PN)

<400> SEQUENCE: 148

caggtccagc tggtacagtc tggggctgag gtgaagaagc ctggggcctc agtgaaggtc      60

tcctgcaagg tttccggaga aataagtact ggatactatt tccactgggt gcgacgaagg     120

cctggaaaag ggcttgagtg gatgggaagg attgatcctg aggatgatag tactaaatat     180

gctgagaggt tcaaagacag agtcaccatg accgaggaca catctacaga cacagcctac     240

atggagctga gcagcctgag atctgaggac acggccgtgt attactgtac cacatggcgg     300

atataccgag atagttctgg ccgccccttc tatgttatgg atgcctgggg ccaagggaca     360

ctagtcacag tctcctca                                                   378


<210> SEQ ID NO 149
<211> LENGTH: 456
<212> TYPE: PRT
<213> ORGANISM: Artificial Sequence
<220> FEATURE:
<223> OTHER INFORMATION: Synthetic: H3 heavy chain

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Val Ser Gly Glu Ile Ser Thr Gly Tyr
            20                  25                  30

Tyr Phe His Phe Val Arg Arg Arg Pro Gly Lys Gly Leu Glu Trp Met
        35                  40                  45

Gly Arg Ile Asp Pro Glu Asp Asp Ser Thr Lys Tyr Ala Glu Arg Phe
    50                  55                  60

Lys Asp Arg Val Thr Met Thr Ala Asp Thr Ser Thr Asp Thr Ala Tyr
65                  70                  75                  80

Met Glu Leu Ser Ser Leu Arg Ser Glu Asp Thr Ala Thr Tyr Phe Cys
                85                  90                  95

Thr Thr Trp Arg Ile Tyr Arg Asp Ser Ser Gly Arg Pro Phe Tyr Val
            100                 105                 110

Met Asp Ala Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205
```

```
Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

<210> SEQ ID NO 150
<211> LENGTH: 1368
<212> TYPE: DNA
<213> ORGANISM: Artificial Sequence
<220> FEATURE:
<223> OTHER INFORMATION: Synthetic: H3 heavy chain (PN)

<400> SEQUENCE: 150

```
caggtccagc tggtacagtc tggggctgag gtgaagaagc ctggggcctc agtgaaggtc     60

tcctgcaagg tttccggaga aataagtact ggatactatt tccactttgt gcgacgaagg    120

cctggaaaag ggcttgagtg gatgggaagg attgatcctg aggatgatag tactaaatat    180

gctgagaggt tcaaagacag agtcaccatg accgcagaca catctacaga cacagcctac    240

atggagctga gcagcctgag atctgaggac acggccactt atttttgtac cacatggcgg    300

atataccgag atagttctgg ccgccccttc tatgttatgg atgcctgggg ccaagggaca    360

ctagtcacag tctcctcagc ctccaccaag ggcccatcgg tcttccccct ggcaccctcc    420

tccaagagca cctctggggg cacagcggcc ctgggctgcc tggtcaagga ctacttcccc    480

gaaccggtga cggtgtcgtg gaactcaggc gccctgacca gcggcgtgca caccttcccg    540

gctgtcctac agtcctcagg actctactcc ctcagcagcg tggtgaccgt gccctccagc    600
```

```
agcttgggca cccagaccta catctgcaac gtgaatcaca agcccagcaa caccaaggtg    660

gacaagaaag ttgagcccaa atcttgtgac aaaactcaca catgcccacc gtgcccagca    720

cctgaactcc tggggggacc gtcagtcttc ctcttccccc caaaacccaa ggacaccctc    780

atgatctccc ggacccctga ggtcacatgc gtggtggtgg acgtgagcca cgaagaccct    840

gaggtcaagt tcaactggta cgtggacggc gtggaggtgc ataatgccaa gacaaagccg    900

cgggaggagc agtacaacag cacgtaccgt gtggtcagcg tcctcaccgt cctgcaccag    960

gactggctga atggcaagga gtacaagtgc aaggtctcca acaaagccct cccagccccc   1020

atcgagaaaa ccatctccaa agccaaaggg cagccccgag aaccacaggt gtacaccctg   1080

cccccatccc gggatgagct gaccaagaac caggtcagcc tgacctgcct ggtcaaaggc   1140

ttctatccca gcgacatcgc cgtggagtgg gagagcaatg ggcagccgga gaacaactac   1200

aagaccacgc ctcccgtgct ggactccgac ggctccttct tcctctacag caagctcacc   1260

gtggacaaga gcaggtggca gcaggggaac gtcttctcat gctccgtgat gcatgaggct   1320

ctgcacaacc actacacgca gaagagcctc tccctgtctc cgggtaaa                1368
```

<210> SEQ ID NO 151
<211> LENGTH: 126
<212> TYPE: PRT
<213> ORGANISM: Artificial Sequence
<220> FEATURE:
<223> OTHER INFORMATION: Synthetic: H3 variable region

<400> SEQUENCE: 151

```
Gln Val Gln Leu Val Gln Ser Gly Ala Glu Val Lys Lys Pro Gly Ala
1               5                   10                  15

Ser Val Lys Val Ser Cys Lys Val Ser Gly Glu Ile Ser Thr Gly Tyr
            20                  25                  30

Tyr Phe His Phe Val Arg Arg Arg Pro Gly Lys Gly Leu Glu Trp Met
        35                  40                  45

Gly Arg Ile Asp Pro Glu Asp Asp Ser Thr Lys Tyr Ala Glu Arg Phe
    50                  55                  60

Lys Asp Arg Val Thr Met Thr Ala Asp Thr Ser Thr Asp Thr Ala Tyr
65                  70                  75                  80

Met Glu Leu Ser Ser Leu Arg Ser Glu Asp Thr Ala Thr Tyr Phe Cys
                85                  90                  95

Thr Thr Trp Arg Ile Tyr Arg Asp Ser Ser Gly Arg Pro Phe Tyr Val
            100                 105                 110

Met Asp Ala Trp Gly Gln Gly Thr Leu Val Thr Val Ser Ser
        115                 120                 125
```

<210> SEQ ID NO 152
<211> LENGTH: 378
<212> TYPE: DNA
<213> ORGANISM: Artificial Sequence
<220> FEATURE:
<223> OTHER INFORMATION: Synthetic: H3 variable region (PN)

<400> SEQUENCE: 152

```
caggtccagc tggtacagtc tggggctgag gtgaagaagc ctggggcctc agtgaaggtc     60

tcctgcaagg tttccggaga aataagtact ggatactatt tccactttgt gcgacgaagg    120

cctggaaaag ggcttgagtg gatgggaagg attgatcctg aggatgatag tactaaatat    180

gctgagaggt tcaaagacag agtcaccatg accgcagaca catctacaga cacagcctac    240

atggagctga gcagcctgag atctgaggac acggccactt atttttgtac cacatggcgg    300
```

atataccgag atagttctgg ccgccccttc tatgttatgg atgcctgggg ccaagggaca 360
ctagtcacag tctcctca 378

<210> SEQ ID NO 153
<211> LENGTH: 214
<212> TYPE: PRT
<213> ORGANISM: Artificial Sequence
<220> FEATURE:
<223> OTHER INFORMATION: Synthetic: L1 light chain

<400> SEQUENCE: 153

Asp Ile Gln Met Thr Gln Ser Pro Ser Ser Val Ser Ala Ser Val Gly
1 5 10 15

Asp Arg Val Thr Ile Thr Cys Leu Ala Ser Glu Asp Ile Tyr Thr Tyr
20 25 30

Leu Thr Trp Tyr Gln Gln Lys Pro Gly Lys Ala Pro Lys Leu Leu Ile
35 40 45

Tyr Gly Ala Asn Lys Leu Gln Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Gly Ser Lys Phe Pro Leu
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 154
<211> LENGTH: 642
<212> TYPE: DNA
<213> ORGANISM: Artificial Sequence
<220> FEATURE:
<223> OTHER INFORMATION: Synthetic: L1 light chain (PN)

<400> SEQUENCE: 154
gacatccaga tgacccagtc tccatcttct gtgtctgcat ctgtaggaga cagagtcacc 60
atcacttgtc tggcaagtga ggacatatac acttatttaa catggtatca gcagaaacca 120
gggaaagccc ctaagctcct gatctatggt gcaaataagt tgcaagatgg ggtcccatca 180
aggttcagcg gcagtggatc tgggacagat ttcactctca ctatcagcag cctgcagcct 240
gaagattttg caacttacta ttgtctacag ggttccaagt ttccgctcac gtttggccag 300
gggaccaagc tggagatcaa acgtacggtg gctgcaccat ctgtcttcat cttcccgcca 360

```
tctgatgagc agttgaaatc tggaactgcc tctgttgtgt gcctgctgaa taacttctat    420

cccagagagg ccaaagtaca gtggaaggtg gacaacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642


<210> SEQ ID NO 155
<211> LENGTH: 107
<212> TYPE: PRT
<213> ORGANISM: Artificial Sequence
<220> FEATURE:
<223> OTHER INFORMATION: Synthetic: L1 variable region

<400> SEQUENCE: 155

Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Tyr Thr Tyr
            20                  25                  30

Leu Thr Trp Tyr Gln Gln Lys Pro Gly Lys Ala Pro Lys Leu Leu Ile
        35                  40                  45

Tyr Gly Ala Asn Lys Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Ser Lys Phe Pro Leu
                85                  90                  95

Thr Phe Gly Gln Gly Thr Lys Leu Glu Ile Lys
            100                 105


<210> SEQ ID NO 156
<211> LENGTH: 321
<212> TYPE: DNA
<213> ORGANISM: Artificial Sequence
<220> FEATURE:
<223> OTHER INFORMATION: Synthetic: L1 variable region (PN)

<400> SEQUENCE: 156

gacatccaga tgacccagtc tccatcttct gtgtctgcat ctgtaggaga cagagtcacc     60

atcacttgtc tggcaagtga ggacatatac acttatttaa catggtatca gcagaaacca    120

gggaaagccc ctaagctcct gatctatggt gcaaataagt tgcaagatgg ggtcccatca    180

aggttcagcg gcagtggatc tgggacagat ttcactctca ctatcagcag cctgcagcct    240

gaagattttg caacttacta ttgtctacag ggttccaagt ttccgctcac gtttggccag    300

gggaccaagc tggagatcaa a                                              321


<210> SEQ ID NO 157
<211> LENGTH: 214
<212> TYPE: PRT
<213> ORGANISM: Artificial Sequence
<220> FEATURE:
<223> OTHER INFORMATION: Synthetic: L3 light chain

<400> SEQUENCE: 157

Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Tyr Thr Tyr
            20                  25                  30
```

-continued

Leu Thr Trp Tyr Gln Gln Lys Pro Gly Lys Ala Pro Gln Leu Leu Ile
        35                  40                  45

Tyr Gly Ala Asn Lys Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Glu Gly Asp Tyr Tyr Cys Leu Gln Gly Ser Lys Phe Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 158
<211> LENGTH: 645
<212> TYPE: DNA
<213> ORGANISM: Artificial Sequence
<220> FEATURE:
<223> OTHER INFORMATION: Synthetic: L3 light chain (PN)

<400> SEQUENCE: 158
gacatccaga tgacccagtc tccatcttct gtgtctgcat ctgtaggaga cagagtcacc 60
atcacttgtc tggcaagtga ggacatatac acttatttaa catggtatca gcagaaacca 120
gggaaagccc ctcaactcct gatctatggt gcaaataagt tgcaagatgg ggtcccatca 180
aggttcagcg gcagtggatc tgggacagat tatactctca ctatcagcag cctgcagcct 240
gaagatgaag ggattacta ttgtctacag ggttccaagt ttccgctcac gtttggccag 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gacaacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 159
<211> LENGTH: 107
<212> TYPE: PRT
<213> ORGANISM: Artificial Sequence
<220> FEATURE:
<223> OTHER INFORMATION: Synthetic: L3 variable region

<400> SEQUENCE: 159

Asp Ile Gln Met Thr Gln Ser Pro Ser Ser Val Ser Ala Ser Val Gly
1 5 10 15

Asp Arg Val Thr Ile Thr Cys Leu Ala Ser Glu Asp Ile Tyr Thr Tyr
20 25 30

Leu Thr Trp Tyr Gln Gln Lys Pro Gly Lys Ala Pro Gln Leu Leu Ile
35 40 45

Tyr Gly Ala Asn Lys Leu Gln Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Glu Gly Asp Tyr Tyr Cys Leu Gln Gly Ser Lys Phe Pro Leu
85 90 95

Thr Phe Gly Gln Gly Thr Lys Leu Glu Ile Lys
100 105

<210> SEQ ID NO 160
<211> LENGTH: 321
<212> TYPE: DNA
<213> ORGANISM: Artificial Sequence
<220> FEATURE:
<223> OTHER INFORMATION: Synthetic: L3 variable region (PN)

<400> SEQUENCE: 160
gacatccaga tgacccagtc tccatcttct gtgtctgcat ctgtaggaga cagagtcacc 60
atcacttgtc tggcaagtga ggacatatac acttatttaa catggtatca gcagaaacca 120
gggaaagccc ctcaactcct gatctatggt gcaaataagt tgcaagatgg ggtcccatca 180
aggttcagcg gcagtggatc tgggacagat tatactctca ctatcagcag cctgcagcct 240
gaagatgaag ggattacta ttgtctacag ggttccaagt ttccgctcac gtttggccag 300
gggaccaagc tggagatcaa a 321

<210> SEQ ID NO 161
<211> LENGTH: 456
<212> TYPE: PRT
<213> ORGANISM: Artificial Sequence
<220> FEATURE:
<223> OTHER INFORMATION: Synthetic: 2c10 rat-human IgG1 chimera

<400> SEQUENCE: 161

Glu Val Gln Leu Gln Gln Ser Gly Ala Glu Leu Val Arg Pro Gly Thr
1 5 10 15

Ser Val Lys Leu Ser Cys Lys Val Ser Gly Glu Ile Ser Thr Gly Tyr
20 25 30

Tyr Phe His Phe Val Arg Arg Arg Pro Gly Gln Gly Leu Glu Trp Ile
35 40 45

Gly Arg Ile Asp Pro Glu Asp Asp Ser Thr Lys Tyr Ala Glu Arg Phe
50 55 60

Lys Asp Arg Ala Thr Leu Thr Ala Gln Thr Ser Ser Asn Thr Ala Tyr
65 70 75 80

Leu Asn Leu Ser Ser Leu Thr Ser Glu Asp Thr Ala Thr Tyr Phe Cys
85 90 95

Thr Thr Trp Arg Ile Tyr Arg Asp Ser Ser Gly Arg Pro Phe Tyr Val
100 105 110

Met Asp Ala Trp Gly Gln Gly Thr Leu Val Thr Val Ser Ser Ala Ser
115 120 125

```
Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

<210> SEQ ID NO 162
<211> LENGTH: 1368
<212> TYPE: DNA
<213> ORGANISM: Artificial Sequence
<220> FEATURE:
<223> OTHER INFORMATION: Synthetic: 2c10 rat-human IgG1 chimera (PN)

<400> SEQUENCE: 162

```
gaggtccagc tacagcagtc tggggctgag cttgtgagac ctgggacctc tgtgaagtta     60

tcttgcaaag tttctggcga aataagtaca ggatactatt tccactttgt gaggcgaagg    120

cctggacagg gtctggaatg gataggaagg attgatcctg aggatgatag tactaaatat    180
```

```
gctgagaggt tcaaagacag ggcgacgctc actgcacaaa catcctccaa cacagcctac    240
ctgaacctca gcagcctgac ctctgaggac actgcaactt atttttgtac cacatggcgg    300
atataccgag atagttctgg ccgccccttc tatgttatgg atgcctgggg tcaaggaaca    360
ctagtcacag tctcctcagc ctccaccaag ggcccatcgg tcttccccct ggcaccctcc    420
tccaagagca cctctggggg cacagcggcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagaaag ttgagcccaa atcttgtgac aaaactcaca catgcccacc gtgcccagca    720
cctgaactcc tggggggacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgt gtggtcagcg tcctcaccgt cctgcaccag    960
gactggctga atggcaagga gtacaagtgc aaggtctcca acaaagccct cccagccccc   1020
atcgagaaaa ccatctccaa agccaaaggg cagccccgag aaccacaggt gtacaccctg   1080
cccccatccc gggatgagct gaccaagaac caggtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctacag caagctcacc   1260
gtggacaaga gcaggtggca gcaggggaac gtcttctcat gctccgtgat gcatgaggct   1320
ctgcacaacc actacacgca gaagagcctc tccctgtctc cgggtaaa                1368
```

<210> SEQ ID NO 163
<211> LENGTH: 214
<212> TYPE: PRT
<213> ORGANISM: Artificial Sequence
<220> FEATURE:
<223> OTHER INFORMATION: Synthetic: 2c10 rat-human CKappa chimera

<400> SEQUENCE: 163

```
Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Asp Ile Tyr Thr Tyr
            20                  25                  30

Leu Thr Trp Tyr Gln Gln Lys Pro Gly Lys Ser Pro Gln Leu Leu Ile
        35                  40                  45

Tyr Gly Ala Asn Lys Leu Gln Asp Gly Val Pro Ser Arg Phe Ser Gly
    50                  55                  60

Ser Gly Ser Gly Thr Gln Tyr Ser Leu Lys Ile Ser Gly Ile Gln Pro
65                  70                  75                  80

Glu Asp Glu Gly Asp Tyr Phe Cys Leu Gln Gly Ser Lys Phe Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 164
<211> LENGTH: 642
<212> TYPE: DNA
<213> ORGANISM: Artificial Sequence
<220> FEATURE:
<223> OTHER INFORMATION: Synthetic: 2c10 rat-human CKappa chimera (PN)

<400> SEQUENCE: 164
gacattcaaa tgacccagtc tccagcttcc ctgtctgcat ctctgggaga aactgtctcc 60
atcgaatgtc tggcaagtga ggacatatac acttatttaa catggtatca gcagaaacca 120
gggaaatctc ctcaactcct gatctatggt gcaaataagt tgcaagatgg ggtcccatca 180
cggttcagtg gcagtggatc tggcacacag tattctctca agatcagcgg catacaacct 240
gaagatgaag ggattattt ctgtctacag ggttccaagt ttccgctcac gttcggttct 300
gggaccaagc tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gacaacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 165
<211> LENGTH: 98
<212> TYPE: PRT
<213> ORGANISM: Artificial Sequence
<220> FEATURE:
<223> OTHER INFORMATION: Synthetic: Heavy chain acceptor framework

<400> SEQUENCE: 165

Gln Val Gln Leu Val Gln Ser Gly Ala Glu Val Lys Lys Pro Gly Ala
1 5 10 15

Ser Val Lys Val Ser Cys Lys Val Ser Gly Tyr Thr Leu Thr Glu Leu
20 25 30

Ser Met His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Glu Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Thr

-continued

```
<210> SEQ ID NO 166
<211> LENGTH: 95
<212> TYPE: PRT
<213> ORGANISM: Artificial Sequence
<220> FEATURE:
<223> OTHER INFORMATION: Synthetic: Light chain acceptor framework

<400> SEQUENCE: 166

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95


<210> SEQ ID NO 167
<211> LENGTH: 11
<212> TYPE: PRT
<213> ORGANISM: Artificial Sequence
<220> FEATURE:
<223> OTHER INFORMATION: Synthetic: JH6 amino acid sequence added to
      SEQ ID NO: 37

<400> SEQUENCE: 167

Trp Gly Gln Gly Thr Leu Val Thr Val Ser Ser
1               5                   10


<210> SEQ ID NO 168
<211> LENGTH: 10
<212> TYPE: PRT
<213> ORGANISM: Artificial Sequence
<220> FEATURE:
<223> OTHER INFORMATION: Synthetic: Jkappa 2 amino acid sequence added
      to SEQ ID NO: 38

<400> SEQUENCE: 168

Phe Gly Gln Gly Thr Lys Leu Glu Ile Lys
1               5                   10
```